United States Patent
Saum et al.

(10) Patent No.: US 11,913,054 B2
(45) Date of Patent: Feb. 27, 2024

(54) FERMENTATIVE PRODUCTION OF N-BUTYLACRYLATE USING ALCOHOL ACYL TRANSFERASE ENZYMES

(71) Applicant: BASF SE, Ludwigshafen am Rhein (DE)

(72) Inventors: Stephan Saum, Lampertheim (DE); Woncheol Kim, Tarrytown, NY (US); Oskar Zelder, Ludwigshafen (DE); Jennifer Jaitzig, Ludwigshafen (DE); Zheyuan Guo, San Diego, CA (US)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/089,642

(22) PCT Filed: Mar. 22, 2017

(86) PCT No.: PCT/EP2017/056872
§ 371 (c)(1),
(2) Date: Sep. 28, 2018

(87) PCT Pub. No.: WO2017/167623
PCT Pub. Date: Oct. 5, 2017

(65) Prior Publication Data
US 2019/0112622 A1    Apr. 18, 2019

(30) Foreign Application Priority Data

Mar. 30, 2016 (EP) ..................................... 16162887

(51) Int. Cl.
*C12P 7/62* (2022.01)
*C12N 9/10* (2006.01)

(52) U.S. Cl.
CPC .............. *C12P 7/62* (2013.01); *C12N 9/1029* (2013.01); *C12Y 203/01084* (2013.01)

(58) Field of Classification Search
CPC .................................. C12N 9/1029; C12P 7/62
See application file for complete search history.

(56) References Cited

U.S. PATENT DOCUMENTS

| | | | | |
|---|---|---|---|---|
| 5,565,350 | A | 10/1996 | Kmiec | |
| 2009/0130729 | A1* | 5/2009 | Symes | C12P 7/62 435/135 |
| 2009/0155869 | A1* | 6/2009 | Buelter | C12N 15/52 435/160 |
| 2015/0184207 | A1* | 7/2015 | Sato | C12Y 203/01084 435/135 |
| 2019/0112622 | A1* | 4/2019 | Saum | C12N 9/1029 |

FOREIGN PATENT DOCUMENTS

| | | |
|---|---|---|
| EP | 2848694 A1 | 3/2015 |
| WO | 0015815 A1 | 3/2000 |
| WO | 0032789 A1 | 6/2000 |
| WO | 2007039415 A1 | 4/2007 |
| WO | 2008143704 A2 | 11/2008 |
| WO | 2010105194 A2 | 9/2010 |
| WO | 2014062556 A2 | 4/2014 |

OTHER PUBLICATIONS

UniProt Accession No. P93094_CUCME, published May 1, 1997 (Year: 1997).*
UniProt Accession No. B1A9J8_CUCME, published Apr. 8, 2008 (Year: 2008).*
UniProt Accession No. Q8GTM5_FRAVE, published Mar. 1, 2003 (Year: 2003).*
UniProt Accession No. Q6R311_MALDO, published Jul. 5, 2004 (Year: 2004).*
UniProt Accession No. BEBT_CLABR, published Mar. 1, 2003 (Year: 2003).*
UniProt Accession No. BEATH_CLABR, published Aug. 1, 1998 (Year: 1998).*
Chu, et al., "Direct fermentation route for the production of acrylic acid", Metabolic Engineering, vol. 32, Nov. 2015, pp. 23-29.
Krivoruchko, et al., "Improving biobutanol production in engineered *Saccharomyces cerevisiae* by manipulation of acetyl-CoA metabolism", Journal of Industrial Microbiology & Biotechnology, vol. 40, Issue 9, Sep. 2013, pp. 1051-1056.
Tang, et al., "Metabolic engineering for enhanced fatty acids synthesis in *Saccharomyces cerevisiae*", Metabolic Engineering, vol. 16, Mar. 2013, pp. 95-102.
Zhou, et al., "Erlotinib versus chemotherapy as first-line treatment for patients with advanced EGFR mutation-positive non-small-cell lung cancer (Optimal, CTONG-0802): a multicentre, open-label, randomised, phase 3 study", The Lancet Oncology, vol. 12, Issue 8, Jul. 22, 2011, pp. 735-742.
Kandasamy et al., Engineering *Escherichia coli* with acrylate pathway genes for propionic acid synthesis and its impact on mixed-acid fermentation, Appl Microbiol Biotechnol (2013) 97: 1191-1200.
Teufel et al., 3-Hydroxypropionyl-Coenzyme A Dehydratase and Acryloyl-Coenzyme A Reductase, Enzymes of the Autotrophic 3-Hydroxypropionate/4-Hydroxybutyrate Cycle in the Sulfolobales, Journal of Bacteriology, Jul. 2009, p. 4572-4581.
El-Sharkawy et al., Functional characterization of a melon alcohol acyl-transferase gene family involved in the biosynthesis of ester volatiles, Plant Molecular Biology, Oct. 2005.
Schadeweg and Boles, Increasing n-butanol production with *Saccharomyces cerevisiae* by optimizing acetyl-CoA synthesis, NADH levels and trans-2-enoyl-CoA reductase expression. Biotechnol Biofuels (2016) 9:257.
Yahyaoui et al. Molecular and biochemical characteristics of a gene encoding an alcohol acyl-transferase involved in the generation of aroma volatile esters during melon ripening, Eur J Biochem (2002) 269, 2359-2366.

(Continued)

*Primary Examiner* — Tekchand Saidha
(74) *Attorney, Agent, or Firm* — Armstrong Teasdale LLP

(57) ABSTRACT

Provided herein is a recombinant nucleic acid molecule, a recombinant microorganism, and a method for fermentative production of n-butylacrylate and other esters from alcohols and acyl-CoA units using alcohol acyl transferase enzymes.

4 Claims, 4 Drawing Sheets

Specification includes a Sequence Listing.

(56) References Cited

OTHER PUBLICATIONS

Steen et al., Metabolic engineering of *Saccharomyces cerevisiae* for the production of n-butanol, Microbial Cell Factories 2008, 7:36.
Nevoigt, Progress in Metabolic Engineering of *Saccharomyces cerevisiae*, Microbiol Mol Biol Rev, Sep. 2008 72(3), p. 379-412.
Oeser et al., Metabolic engineering of yeast for increased efficiency and yield in industrial fuel ethanol production, Yeast 32(1), S88.
Lowry et al., Protein measurement with the folin phenol reagent, J Biol Chem (1951) 193: 265-275.
Bradford. A Rapid and Sensitive Method for the Quantitation of Microgram Quantities of Protein Utilizing the Principle of Protein-Dye Binding, Analyt Biochem (1976) 72: 248-254.
Wang and De Luca, The biosynthesis and regulation of biosynthesis of Concord grape fruit esters, including 'foxy' methylanthranilate, The Plant Journal (2005) 44, 606-619.
Stewart et al., The Pun1 gene for pungency in pepper encodes a putative acyltransferase, The Plant Journal (2005) 42, 675-688.
Cregg et al., Pichia pastoris as a Host System for Transformations, Molecular and Cellular Biology (Dec. 1985) 5(12), p. 3376-3385.
Prabhu et al., Effect of ethanolic and ethylacetate extract of Merremia emarginata (BURM.F) in Rheumatoid Arthritis, IRJP 2012, 3(9).
Altschul et al., Gapped Blast and PSI-Blast: a new generation of protein database search programs, Nucleic Acids Research, 1997, vol. 25, No. 17, 3389-3402.
Smith and Waterman, Comparison of Biosequences, Adv Appl Math 2 (1981), 482-489.
Pearson and Lipman, Improved tools for biological sequence comparison, Proc Natl Acad Sci USA, Apr. 1988, vol. 85, pp. 2444-2448.
International Search Report and Written Opinion for International Application No. PCT/EP2017/056872, dated May 12, 2017, 10 pages.

* cited by examiner

SEQUENCE LISTING

```
<160> NUMBER OF SEQ ID NOS: 71

<210> SEQ ID NO 1
<211> LENGTH: 1407
<212> TYPE: DNA
<213> ORGANISM: Cucumis melo
<220> FEATURE:
<223> OTHER INFORMATION: CM-AAT1

<400> SEQUENCE: 1
atgcatcatc accaccacca cgagactatg cagactatcg atttctcatt ccacgttaga      60
aagtgtcagc cagagttgat cgctccagct aacccaactc catacgagtt caagcaattg     120
tccgacgttg acgaccaaca gtccttgaga ttgcagttgc cattcgttaa catctaccca     180 cacaaccat ccttggaggg tagagatcca gttaaggtta tcaaagaggc tatcggtaag     240
gctttggttt tctactaccc attggctggt agattgagag agggtccagg tagaaagttg     300
ttcgttgagt gtactggtga gggtatcttg ttcattgaag ctgacgctga cgtttccttg     360
gaagagttct gggatacttt gccatactcc ttgtcctcca tgcagaacaa catcatccac     420
aacgctttga actccgacga ggttttgaac tccccctttgt tgttgatcca ggttactaga     480
ttgaagtgtg gtggtttcat cttcggtttg tgtttcaacc acactatggc tgacggtttc     540
ggtatcgttc agttcatgaa ggctactgct gagatcgcta gaggtgcttt cgctccatct     600
attttgccag tttggcagag agctttgttg actgctagag atccaccaag aatcactttc     660
agacactacg agtacgacca ggttgttgac atgaagtccg gtttgatccc agttaactcc     720
aagatcgacc agttgttctt cttctcccaa ttgcaaatct ccactttgag acagactttg     780
ccagctcact gcacgactg tccatctttc gaagttttga ctgcttacgt ttggagattg     840
agaactatcg ctttgcagtt caagccagag gaagaggtta gattcctttg tgttatgaac     900
ttgagatcca agattgacat cccattgggt tactacggta acgctgttgt tgttccagct     960
gttatcacta ctgctgctaa gttgtgtggt aacccttgg gttacgctgt tgacttgatc    1020
agaaaggcta aggctaaagc tactatgaa tacatcaagt ccactgttga tttgatggtt    1080
atcaagggta gaccatactt cactgttgtt ggttccttca tgatgtccga cttgactaga    1140
atcggtgttg agaacgttga cttcggttgg ggtaaggcta ttttcggtgg tccaactact    1200
actggtgcta gaatcactag aggtttggtt tcttttctgtg ttccattcat gaacagaaac    1260
ggtgagaagg gtactgcttg gtccttgtgt ttgccaccac cagctatgga agagttccaga    1320 gctaacgttc acgcttcctt gcaggttaag caagttgttg atgctgttga ctcccacatg    1380
cagactattc aatccgcttc caagtaa                                        1407
```

<210> SEQ ID NO 2
<211> LENGTH: 468
<212> TYPE: PRT
<213> ORGANISM: Cucumis melo
<220> FEATURE:
<223> OTHER INFORMATION: CM-AAT1_AA

<400> SEQUENCE: 2

```
Met His His His His His Glu Thr Met Gln Thr Ile Asp Phe Ser
1               5                   10                  15

Phe His Val Arg Lys Cys Gln Pro Glu Leu Ile Ala Pro Ala Asn Pro
            20                  25                  30

Thr Pro Tyr Glu Phe Lys Gln Leu Ser Asp Val Asp Gln Gln Ser
            35                  40                  45

Leu Arg Leu Gln Leu Pro Phe Val Asn Ile Tyr Pro His Asn Pro Ser
50                  55                  60

Leu Glu Gly Arg Asp Pro Val Lys Val Ile Lys Glu Ala Ile Gly Lys
65                  70                  75                  80

Ala Leu Val Phe Tyr Tyr Pro Leu Ala Gly Arg Leu Arg Glu Gly Pro
                85                  90                  95

Gly Arg Lys Leu Phe Val Glu Cys Thr Gly Glu Gly Ile Leu Phe Ile
            100                 105                 110

Glu Ala Asp Ala Asp Val Ser Leu Glu Glu Phe Trp Asp Thr Leu Pro
        115                 120                 125

Tyr Ser Leu Ser Ser Met Gln Asn Asn Ile Ile His Asn Ala Leu Asn
    130                 135                 140

Ser Asp Glu Val Leu Asn Ser Pro Leu Leu Leu Ile Gln Val Thr Arg
145                 150                 155                 160

Leu Lys Cys Gly Gly Phe Ile Phe Gly Leu Cys Phe Asn His Thr Met
                165                 170                 175

Ala Asp Gly Phe Gly Ile Val Gln Phe Met Lys Ala Thr Ala Glu Ile
            180                 185                 190

Ala Arg Gly Ala Phe Ala Pro Ser Ile Leu Pro Val Trp Gln Arg Ala
        195                 200                 205

Leu Leu Thr Ala Arg Asp Pro Pro Arg Ile Thr Phe Arg His Tyr Glu
    210                 215                 220

Tyr Asp Gln Val Val Asp Met Lys Ser Gly Leu Ile Pro Val Asn Ser
225                 230                 235                 240

Lys Ile Asp Gln Leu Phe Phe Phe Ser Gln Leu Gln Ile Ser Thr Leu
                245                 250                 255

Arg Gln Thr Leu Pro Ala His Leu His Asp Cys Pro Ser Phe Glu Val
            260                 265                 270

Leu Thr Ala Tyr Val Trp Arg Leu Arg Thr Ile Ala Leu Gln Phe Lys
        275                 280                 285

Pro Glu Glu Glu Val Arg Phe Leu Cys Val Met Asn Leu Arg Ser Lys
    290                 295                 300

Ile Asp Ile Pro Leu Gly Tyr Tyr Gly Asn Ala Val Val Pro Ala
305                 310                 315                 320

Val Ile Thr Thr Ala Ala Lys Leu Cys Gly Asn Pro Leu Gly Tyr Ala
                325                 330                 335

Val Asp Leu Ile Arg Lys Ala Lys Ala Lys Ala Thr Met Glu Tyr Ile
            340                 345                 350

Lys Ser Thr Val Asp Leu Met Val Ile Lys Gly Arg Pro Tyr Phe Thr
        355                 360                 365
```

Val Val Gly Ser Phe Met Met Ser Asp Leu Thr Arg Ile Gly Val Glu
        370                 375                 380

Asn Val Asp Phe Gly Trp Gly Lys Ala Ile Phe Gly Gly Pro Thr Thr
385                 390                 395                 400

Thr Gly Ala Arg Ile Thr Arg Gly Leu Val Ser Phe Cys Val Pro Phe
                405                 410                 415

Met Asn Arg Asn Gly Glu Lys Gly Thr Ala Leu Ser Leu Cys Leu Pro
                420                 425                 430

Pro Pro Ala Met Glu Arg Phe Arg Ala Asn Val His Ala Ser Leu Gln
            435                 440                 445

Val Lys Gln Val Val Asp Ala Val Asp Ser His Met Gln Thr Ile Gln
    450                 455                 460

Ser Ala Ser Lys
465

<210> SEQ ID NO 3
<211> LENGTH: 1383
<212> TYPE: DNA
<213> ORGANISM: Malus pumila
<220> FEATURE:
<223> OTHER INFORMATION: MpAAT1

<400> SEQUENCE: 3

| | | | | | |
|---|---|---|---|---|---|
| atgcatcacc | accaccatca | ctcattctcc | gtcttgcagg | ttaagagatt | gcagccagag | 60 |
| ttgatcactc | cagctaagtc | tactccacaa | gagactaagt | tcttgtccga | catcgacgac | 120 |
| caagagtcct | tgagagttca | gatcccaatc | atcatgtgct | acaaggacaa | cccatccctg | 180 |
| aacaagaaca | gaaacccagt | caaggctatc | agagaggctt | tgtccagagc | cttggtttac | 240 |
| tactacccat | tggccggtag | attgagagag | ggtccaaaca | gaaagttggt | cgttgactgt | 300 |
| aacggtgagg | gtatcttgtt | cgttgaagct | tccgctgacg | ttaccttgga | caattgggt | 360 |
| gacaagatcc | tgccaccatg | tcctttgttg | aagagttcc | tgtacaactt | cccaggttcc | 420 |
| gacggtatta | tcgactgtcc | attgctgttg | atccaggtta | cctgtttgac | ctgcggtggt | 480 |
| ttcatcttgg | ccttgagatt | gaaccacact | atgtgtgacg | ctgccggttt | gttgttgttc | 540 |
| ttgactgcta | ttgctgagat | ggctagaggt | gctcacgctc | atctattttt | gccagtttgg | 600 |
| gagagagagt | tgttgttcgc | tagagatcca | ccaagaatca | cttgtgctca | ccacgaatac | 660 |
| gaggacgtta | ttggtcactc | tgacggttct | tacgcttctt | ccaaccagtc | caacatggtc | 720 |
| cagagatcct | tttacttcgg | tgccaaagag | atgagggtcc | tgagaaagca | aattccacca | 780 |
| cacttgatct | ccacctgttc | caccttcgac | ttgatcactg | cttgtctgtg | aagtgtaga | 840 |
| accttggcct | tgaacatcaa | cccaaaagag | gccgttagag | tctcctgtat | cgttaacgct | 900 |
| agaggtaagc | acaacaacgt | cagattgcca | ttgggttact | acggtaacgc | tttcgctttc | 960 |
| ccagctgcta | tttctaaggc | tgagccattg | tgcaagaacc | ctttgggtta | cgctttggag | 1020 |
| ttggtcaaga | aagctaaggc | caccatgaac | gaagagtact | tgagatccgt | tgccgacttg | 1080 |
| ttggtcttga | gaggtagacc | acaatactcc | tccactggtt | cctacttgat | cgtttccgac | 1140 |
| aacaccagag | ttggtttcgg | tgacgttaac | ttcggttggg | gtcaaccagt | ttttgccggt | 1200 |
| ccagttaagg | ctttggacct | gatctctttc | tacgtccaac | acaagaacaa | caccgaggac | 1260 |
| ggtattttgg | tcccaatgtg | tttgccatcc | tccgccatgg | aaagattcca | acaagagttg | 1320 |
| gagagaatca | cccaagagcc | aaaagaggac | atctgcaaca | acttgagatc | cacctctcag | 1380 |
| taa | | | | | | 1383 |

<210> SEQ ID NO 4
<211> LENGTH: 460
<212> TYPE: PRT
<213> ORGANISM: Malus pumila
<220> FEATURE:
<223> OTHER INFORMATION: MpAAT1_AA

<400> SEQUENCE: 4

```
Met His His His His His Ser Phe Ser Val Leu Gln Val Lys Arg
1               5                   10                  15

Leu Gln Pro Glu Leu Ile Thr Pro Ala Lys Ser Thr Pro Gln Glu Thr
            20                  25                  30

Lys Phe Leu Ser Asp Ile Asp Asp Gln Glu Ser Leu Arg Val Gln Ile
        35                  40                  45

Pro Ile Ile Met Cys Tyr Lys Asp Asn Pro Ser Leu Asn Lys Asn Arg
    50                  55                  60

Asn Pro Val Lys Ala Ile Arg Glu Ala Leu Ser Arg Ala Leu Val Tyr
65                  70                  75                  80

Tyr Tyr Pro Leu Ala Gly Arg Leu Arg Glu Gly Pro Asn Arg Lys Leu
                85                  90                  95

Val Val Asp Cys Asn Gly Glu Gly Ile Leu Phe Val Glu Ala Ser Ala
            100                 105                 110

Asp Val Thr Leu Glu Gln Leu Gly Asp Lys Ile Leu Pro Pro Cys Pro
        115                 120                 125

Leu Leu Glu Glu Phe Leu Tyr Asn Phe Pro Gly Ser Asp Gly Ile Ile
    130                 135                 140

Asp Cys Pro Leu Leu Leu Ile Gln Val Thr Cys Leu Thr Cys Gly Gly
145                 150                 155                 160

Phe Ile Leu Ala Leu Arg Leu Asn His Thr Met Cys Asp Ala Ala Gly
                165                 170                 175

Leu Leu Leu Phe Leu Thr Ala Ile Ala Glu Met Ala Arg Gly Ala His
            180                 185                 190

Ala Pro Ser Ile Leu Pro Val Trp Glu Arg Glu Leu Leu Phe Ala Arg
        195                 200                 205

Asp Pro Pro Arg Ile Thr Cys Ala His His Glu Tyr Glu Asp Val Ile
    210                 215                 220

Gly His Ser Asp Gly Ser Tyr Ala Ser Ser Asn Gln Ser Asn Met Val
225                 230                 235                 240

Gln Arg Ser Phe Tyr Phe Gly Ala Lys Glu Met Arg Val Leu Arg Lys
                245                 250                 255

Gln Ile Pro Pro His Leu Ile Ser Thr Cys Ser Thr Phe Asp Leu Ile
            260                 265                 270

Thr Ala Cys Leu Trp Lys Cys Arg Thr Leu Ala Leu Asn Ile Asn Pro
        275                 280                 285

Lys Glu Ala Val Arg Val Ser Cys Ile Val Asn Ala Arg Gly Lys His
    290                 295                 300

Asn Asn Val Arg Leu Pro Leu Gly Tyr Tyr Gly Asn Ala Phe Ala Phe
305                 310                 315                 320

Pro Ala Ala Ile Ser Lys Ala Glu Pro Leu Cys Lys Asn Pro Leu Gly
                325                 330                 335

Tyr Ala Leu Glu Leu Val Lys Lys Ala Lys Ala Thr Met Asn Glu Glu
            340                 345                 350

Tyr Leu Arg Ser Val Ala Asp Leu Leu Val Leu Arg Gly Arg Pro Gln
        355                 360                 365
```

```
Tyr Ser Ser Thr Gly Ser Tyr Leu Ile Val Ser Asp Asn Thr Arg Val
        370                 375                 380

Gly Phe Gly Asp Val Asn Phe Gly Trp Gly Gln Pro Val Phe Ala Gly
385                 390                 395                 400

Pro Val Lys Ala Leu Asp Leu Ile Ser Phe Tyr Val Gln His Lys Asn
            405                 410                 415

Asn Thr Glu Asp Gly Ile Leu Val Pro Met Cys Leu Pro Ser Ser Ala
        420                 425                 430

Met Glu Arg Phe Gln Gln Glu Leu Glu Arg Ile Thr Gln Glu Pro Lys
        435                 440                 445

Glu Asp Ile Cys Asn Asn Leu Arg Ser Thr Ser Gln
        450                 455                 460

<210> SEQ ID NO 5
<211> LENGTH: 1386
<212> TYPE: DNA
<213> ORGANISM: Fragaria vesca
<220> FEATURE:
<223> OTHER INFORMATION: VAAT

<400> SEQUENCE: 5
atgcaccatc accatcacca tgagaagatt gaggtttcaa tcatatccaa acacacaatc      60
aaacccagca cgagcagttc tcctttgcaa ccatacaagc taaccttatt ggatcagtta     120
actccaccgt cctacgtccc tatggtgttt ttctacccta ttacgggtcc agccgtgttc     180
aatttgcaaa cattggcaga tctgagacac gcattgtctg agactttgac actgtactat     240
ccattatcgg gtcgtgtgaa aaacaatctg tatattgatg atttgaaga gggtgttccc      300 tacttggaag cgagagtgaa ctgcgacatg aatgactttt tgaggcttcc aaaaatcgaa     360
tgtttgaatg aatttgttcc aatcaagcct tttttctatg gaggctatatc cgatgaaaga    420 tatcctttac ttggtgtgca agtcaacatt ttcaattccg ggatcgcaat tggagttagc     480
gtatcccata agttgatcga cggtcgtaca tctgactgct tcctgaagtc atggtgtgct    540
gtattccgag atcacgtgca aaaatcatc catcccaatc tttcgcaggc agctttgttg     600
tttcctccgc gtgacgatct cccagagaaa tatgctagac aaatggaggg cttgtggttt    660
gttggtaaaa aggttgctac tagaagattc gtgttcggag caaaggctat ctctgttatt    720
caagacgagg ctaagtcaga gtccgttcca aaaccatcaa gagttcaagc tgtcacatcc    780
ttcttatgga acaccttatt gcaacttct agagctttaa cttcgggtac aactagtact   840
agactatcca ttgctaccca ggtcgtcaac attagaagta ggagaaatat ggaaacggtg     900
tgggataatg ccattggtaa tcttatctgg tttgctcctg caatcttgga actgtctcat    960
acaaccttgg gatctccga tttgaaactg tgtgatctgg ttaacctact caatggttcc    1020
gtcaaacaat gtaatggcga ttacttcgag actttatgg gtaaggaagg ttatggatca    1080
atgtgtgagt acttggactt ccaacgtaca atgtccagca tggaaccagc tccagaaatc    1140
taccttttca cttcatggac caatttcttc aaccagctag actttggatg gggtagaacc    1200
agctggattg gtgtagctgg aaagatagaa agtgcttttt gtaacctgac tacattggta    1260
cccactcctt gcgatacagg aattgaggca tgggttaacc ttgaagagga aaagatggcc    1320
atgttggaac aagaccctca gtttctggcc ttagcctctc caaaaacttt gatatctagg    1380
tattaa                                                                1386

<210> SEQ ID NO 6
```

<211> LENGTH: 461
<212> TYPE: PRT
<213> ORGANISM: Fragaria vesca
<220> FEATURE:
<223> OTHER INFORMATION: VAAT_AA

<400> SEQUENCE: 6

```
Met His His His His His Glu Lys Ile Glu Val Ser Ile Ile Ser
1               5                   10                  15

Lys His Thr Ile Lys Pro Ser Thr Ser Ser Pro Leu Gln Pro Tyr
            20                  25                  30

Lys Leu Thr Leu Leu Asp Gln Leu Thr Pro Pro Ser Tyr Val Pro Met
            35                  40                  45

Val Phe Phe Tyr Pro Ile Thr Gly Pro Ala Val Phe Asn Leu Gln Thr
50                  55                  60

Leu Ala Asp Leu Arg His Ala Leu Ser Glu Thr Leu Thr Leu Tyr Tyr
65                  70                  75                  80

Pro Leu Ser Gly Arg Val Lys Asn Asn Leu Tyr Ile Asp Asp Phe Glu
                85                  90                  95

Glu Gly Val Pro Tyr Leu Glu Ala Arg Val Asn Cys Asp Met Asn Asp
            100                 105                 110

Phe Leu Arg Leu Pro Lys Ile Glu Cys Leu Asn Glu Phe Val Pro Ile
        115                 120                 125

Lys Pro Phe Ser Met Glu Ala Ile Ser Asp Gly Arg Tyr Pro Leu Leu
130                 135                 140

Gly Val Gln Val Asn Ile Phe Asn Ser Gly Ile Ala Ile Gly Val Ser
145                 150                 155                 160

Val Ser His Lys Leu Ile Asp Gly Arg Thr Ser Asp Cys Phe Leu Lys
                165                 170                 175

Ser Trp Cys Ala Val Phe Arg Gly Ser Arg Asp Lys Ile Ile His Pro
            180                 185                 190

Asn Leu Ser Gln Ala Ala Leu Leu Phe Pro Pro Arg Asp Asp Leu Pro
        195                 200                 205

Glu Lys Tyr Ala Arg Gln Met Glu Gly Leu Trp Phe Val Gly Lys Lys
210                 215                 220

Val Ala Thr Arg Arg Phe Val Phe Gly Ala Lys Ala Ile Ser Val Ile
225                 230                 235                 240

Gln Asp Glu Ala Lys Ser Glu Ser Val Pro Lys Pro Ser Arg Val Gln
                245                 250                 255

Ala Val Thr Ser Phe Leu Trp Lys His Leu Ile Ala Thr Ser Arg Ala
            260                 265                 270

Leu Thr Ser Gly Thr Thr Ser Thr Arg Leu Ser Ile Ala Thr Gln Val
        275                 280                 285

Val Asn Ile Arg Ser Arg Arg Asn Met Glu Thr Val Trp Asp Asn Ala
290                 295                 300

Ile Gly Asn Leu Ile Trp Phe Ala Pro Ala Ile Leu Glu Leu Ser His
305                 310                 315                 320

Thr Thr Leu Glu Ile Ser Asp Leu Lys Leu Cys Asp Leu Val Asn Leu
                325                 330                 335

Leu Asn Gly Ser Val Lys Gln Cys Asn Gly Asp Tyr Phe Glu Thr Phe
            340                 345                 350

Met Gly Lys Glu Gly Tyr Gly Ser Met Cys Glu Tyr Leu Asp Phe Gln
        355                 360                 365

Arg Thr Met Ser Ser Met Glu Pro Ala Pro Glu Ile Tyr Leu Phe Thr
370                 375                 380
```

Ser Trp Thr Asn Phe Phe Asn Gln Leu Asp Phe Gly Trp Gly Arg Thr
385                 390                 395                 400

Ser Trp Ile Gly Val Ala Gly Lys Ile Glu Ser Ala Phe Cys Asn Leu
            405                 410                 415

Thr Thr Leu Val Pro Thr Pro Cys Asp Thr Gly Ile Glu Ala Trp Val
                420                 425                 430

Asn Leu Glu Glu Glu Lys Met Ala Met Leu Glu Gln Asp Pro Gln Phe
        435                 440                 445

Leu Ala Leu Ala Ser Pro Lys Thr Leu Ile Ser Arg Tyr
    450                 455                 460

<210> SEQ ID NO 7
<211> LENGTH: 1404
<212> TYPE: DNA
<213> ORGANISM: Cucumis melo
<220> FEATURE:
<223> OTHER INFORMATION: CM-AAT2

<400> SEQUENCE: 7
atgcatcacc atcaccacca cgagactatg cagactatcg acttctcatt ccaggttaga      60
aagtgtcagc cagagttgat cgctccagct aacccaactc catacgagtt caagcaattg     120
tccgacgttg acgaccaaca gtccttgaga ttccagttgc cattggttaa catctaccac     180
cacaacccat ccttggaggg tagagatcca gttaaggtta tcaaagaggc tatcgctaag     240
gctttggttt tctactaccc attggctggt agattgagag agggtcctgg tagaaagttg     300
ttcgttgagt gtactggtga gggtatcttg ttcattgaag ctgacgctga cgtttccttg     360
gagcagttca gagatacttt gccatactcc ttgtcctcca tggaaaacaa catcatccac     420
aactcattga actccgacgg tgttttgaac tccccttttgt tgttgatcca ggttactaga     480
ttgaagtgtg gtggtttcat cttcggtatc cacttcgacc acactatggc tgacggtttt     540
ggtatcgctc agttcatgaa ggctattgct gagatcgcta gaggtgcttt cgctccatct     600
attttgccag tttggcagag agctttgttg actgctagag atcctccaag aatcactgtt     660
agacactacg agtacgacca ggttgttgac actaagtcca ctttgatccc agctaacaac     720
atgatcgaca gattgttctt cttcactcag agacagatct ccacattgag acagactttg     780
ccagctcact gcacgactg ttcttcattc gaggttttga ctgcttacgt ttggagattg     840
agaactatcg ctttccagtt gaagccagag gaagaggtta gattcttgtg tgttgttaac     900
ttgagatcca agatcgacat cccattgggt ttctacggta acgctatcgt tttcccagct     960
gttatcacta ctgttgctaa gttgtgtggt aacccttgg gttacgctgt tgacttgatc    1020
agaaaggcta aggctaaagc tacaaaagag tacatcaagt ccatggttga cttcatggtt    1080
atcaagggta gaccaagatt cactgagatc ggtccattca tgatgtccga cattactaga    1140
atcggtttcg agaacgttga cttcggttgg ggtaaggcta ttttcggtgg tccaattatc    1200
ggtggttgtg gtatcatcag aggtatgatc tcttactcca ttgctttcat gaacagaaac    1260
ggtgagaagg gaatcgttgt tccattgtgt ttgccaccac cagctatgga agattcaga    1320
gctaacgttc acgcttcctt gcaggttatc caggttttgg acaaggttga cagagacatg    1380
caaacaatct tgtccgcttt gtaa                                            1404

<210> SEQ ID NO 8
<211> LENGTH: 467
<212> TYPE: PRT
<213> ORGANISM: Cucumis melo

<220> FEATURE:
<223> OTHER INFORMATION: CM-AAT2_AA

<400> SEQUENCE: 8

```
Met His His His His His Glu Thr Met Gln Thr Ile Asp Phe Ser
1               5                   10                  15

Phe Gln Val Arg Lys Cys Gln Pro Glu Leu Ile Ala Pro Ala Asn Pro
            20                  25                  30

Thr Pro Tyr Glu Phe Lys Gln Leu Ser Asp Val Asp Asp Gln Gln Ser
        35                  40                  45

Leu Arg Phe Gln Leu Pro Leu Val Asn Ile Tyr His His Asn Pro Ser
    50                  55                  60

Leu Glu Gly Arg Asp Pro Val Lys Val Ile Lys Glu Ala Ile Ala Lys
65                  70                  75                  80

Ala Leu Val Phe Tyr Tyr Pro Leu Ala Gly Arg Leu Arg Glu Gly Pro
                85                  90                  95

Gly Arg Lys Leu Phe Val Glu Cys Thr Gly Glu Gly Ile Leu Phe Ile
            100                 105                 110

Glu Ala Asp Ala Asp Val Ser Leu Glu Gln Phe Arg Asp Thr Leu Pro
        115                 120                 125

Tyr Ser Leu Ser Ser Met Glu Asn Asn Ile Ile His Asn Ser Leu Asn
    130                 135                 140

Ser Asp Gly Val Leu Asn Ser Pro Leu Leu Ile Gln Val Thr Arg
145                 150                 155                 160

Leu Lys Cys Gly Gly Phe Ile Phe Gly Ile His Phe Asp His Thr Met
                165                 170                 175

Ala Asp Gly Phe Gly Ile Ala Gln Phe Met Lys Ala Ile Ala Glu Ile
            180                 185                 190

Ala Arg Gly Ala Phe Ala Pro Ser Ile Leu Pro Val Trp Gln Arg Ala
        195                 200                 205

Leu Leu Thr Ala Arg Asp Pro Arg Ile Thr Val Arg His Tyr Glu
    210                 215                 220

Tyr Asp Gln Val Val Asp Thr Lys Ser Thr Leu Ile Pro Ala Asn Asn
225                 230                 235                 240

Met Ile Asp Arg Leu Phe Phe Phe Thr Gln Arg Gln Ile Ser Thr Leu
                245                 250                 255

Arg Gln Thr Leu Pro Ala His Leu His Asp Cys Ser Ser Phe Glu Val
            260                 265                 270

Leu Thr Ala Tyr Val Trp Arg Leu Arg Thr Ile Ala Phe Gln Leu Lys
        275                 280                 285

Pro Glu Glu Glu Val Arg Phe Leu Cys Val Val Asn Leu Arg Ser Lys
    290                 295                 300

Ile Asp Ile Pro Leu Gly Phe Tyr Gly Asn Ala Ile Val Phe Pro Ala
305                 310                 315                 320

Val Ile Thr Thr Val Ala Lys Leu Cys Gly Asn Pro Leu Gly Tyr Ala
                325                 330                 335

Val Asp Leu Ile Arg Lys Ala Lys Ala Thr Lys Glu Tyr Ile
            340                 345                 350

Lys Ser Met Val Asp Phe Met Val Ile Lys Gly Arg Pro Arg Phe Thr
        355                 360                 365

Glu Ile Gly Pro Phe Met Met Ser Asp Ile Thr Arg Ile Gly Phe Glu
    370                 375                 380

Asn Val Asp Phe Gly Trp Gly Lys Ala Ile Phe Gly Gly Pro Ile Ile
385                 390                 395                 400
```

Gly Gly Cys Gly Ile Ile Arg Gly Met Ile Ser Tyr Ser Ile Ala Phe
            405                 410                 415

Met Asn Arg Asn Gly Glu Lys Gly Ile Val Val Pro Leu Cys Leu Pro
        420                 425                 430

Pro Pro Ala Met Glu Arg Phe Arg Ala Asn Val His Ala Ser Leu Gln
    435                 440                 445

Val Ile Gln Val Leu Asp Lys Val Asp Arg Asp Met Gln Thr Ile Leu
    450                 455                 460

Ser Ala Leu
465

<210> SEQ ID NO 9
<211> LENGTH: 1398
<212> TYPE: DNA
<213> ORGANISM: Malus domestica
<220> FEATURE:
<223> OTHER INFORMATION: Md-AAT2

<400> SEQUENCE: 9

| | | |
|---|---|---|
| atgcatcacc atcaccacca catgccattc tccgttttgc aggttaagag attgcagttg | 60 |
| gagttgatca ctcctgctaa gccaacattg caagaggcta gttcttgtc cgacatcgac | 120 |
| gaccaagagg gtttgagatt ccaggttcca gttatcatgt gttacaagga caacccatcc | 180 |
| ttgaacaaga actgtaaccc agttaaggtt atcagagagg ctttgtccag agctttggtt | 240 |
| tactactacc cattggctgg tagattgaaa gagggtccaa acagaaagtt gatggttgac | 300 |
| tgtaacggtg agggtatctt gttcgttgaa gcttccgctg acgttacttt ggagcaattg | 360 |
| ggtgacaaga ttttgccacc atgtcctttg ttggaagagt ttttgttcaa cttcccaggt | 420 |
| tccgacggta tcatcggatg tccttttgttg ttggttcagg ttacttgttt gacttgtggt | 480 |
| ggtttcatct tggctttgag agttaaccac actatgtgtg acgctccagg tttgttgttg | 540 |
| ttcttgactg ctatcgctga gatggctaga ggtgctcatg ctccatctat tttgccagtt | 600 |
| tgggagagag agttgttgtt ttccagagat ccaccaagaa tcacttgtgc tcaccacgaa | 660 |
| tacgaggacg ttattgacca ctctgacggt ttgtacgctt cttccaacca gtccaacatg | 720 |
| gttcagagat ccttctactt cggtgctaaa gagatgagag ttttgagaaa gcagatccca | 780 |
| ccacacttga tctccacttg ttccactttc gacttgatca ctgcttgttt gtggaagtgt | 840 |
| agaactttgg ctttgaacat caacccaaaa gaggctgtta gagtttcctg tatcgttaac | 900 |
| gctagaggta agcacaacaa cgttagattg ccattgggtt actacggtaa cgcttcgct | 960 |
| ttcccagctg ctatttctaa ggctgagcca ttgtgtaaga acccttggg ttacgctttg | 1020 |
| gagttggtta agaaagctaa ggctactatg aacgaagagt acttgagatc cgttgctgac | 1080 |
| ttgttggttt tgagaggtag acctcagtac tcctccactg gatcctactt gatcgtttcc | 1140 |
| gacaacacta gagctggttt cggtgacgtt aacttcggtt ggggtcaacc agttttttgct | 1200 |
| ggtccagcta agctttgga cttgatttcc ttctacgttc aacacaagaa caatactgag | 1260 |
| gacggaattt tggttccaat gtgtttgcca tcctccgcta tggaaagatt ccagcaagag | 1320 |
| ttggagagaa tcactcaaga gcctaaagag gacatctgta caatttgag atccactaga | 1380 |
| attatgtcca tgatgtaa | 1398 |

<210> SEQ ID NO 10
<211> LENGTH: 465
<212> TYPE: PRT
<213> ORGANISM: Malus domestica
<220> FEATURE:
<223> OTHER INFORMATION: Md-AAT2_AA

<400> SEQUENCE: 10

```
Met His His His His His Met Pro Phe Ser Val Leu Gln Val Lys
1               5                   10                  15

Arg Leu Gln Leu Glu Leu Ile Thr Pro Ala Lys Pro Thr Leu Gln Glu
            20                  25                  30

Ala Lys Phe Leu Ser Asp Ile Asp Asp Gln Glu Gly Leu Arg Phe Gln
        35                  40                  45

Val Pro Val Ile Met Cys Tyr Lys Asp Asn Pro Ser Leu Asn Lys Asn
    50                  55                  60

Cys Asn Pro Val Lys Val Ile Arg Glu Ala Leu Ser Arg Ala Leu Val
65                  70                  75                  80

Tyr Tyr Tyr Pro Leu Ala Gly Arg Leu Lys Glu Gly Pro Asn Arg Lys
                85                  90                  95

Leu Met Val Asp Cys Asn Gly Glu Gly Ile Leu Phe Val Glu Ala Ser
            100                 105                 110

Ala Asp Val Thr Leu Glu Gln Leu Gly Asp Lys Ile Leu Pro Pro Cys
        115                 120                 125

Pro Leu Leu Glu Glu Phe Leu Phe Asn Phe Pro Gly Ser Asp Gly Ile
    130                 135                 140

Ile Gly Cys Pro Leu Leu Leu Val Gln Val Thr Cys Leu Thr Cys Gly
145                 150                 155                 160

Gly Phe Ile Leu Ala Leu Arg Val Asn His Thr Met Cys Asp Ala Pro
                165                 170                 175

Gly Leu Leu Leu Phe Leu Thr Ala Ile Ala Glu Met Ala Arg Gly Ala
            180                 185                 190

His Ala Pro Ser Ile Leu Pro Val Trp Glu Arg Glu Leu Leu Phe Ser
        195                 200                 205

Arg Asp Pro Pro Arg Ile Thr Cys Ala His His Glu Tyr Glu Asp Val
    210                 215                 220

Ile Asp His Ser Asp Gly Leu Tyr Ala Ser Ser Asn Gln Ser Asn Met
225                 230                 235                 240

Val Gln Arg Ser Phe Tyr Phe Gly Ala Lys Glu Met Arg Val Leu Arg
                245                 250                 255

Lys Gln Ile Pro Pro His Leu Ile Ser Thr Cys Ser Thr Phe Asp Leu
            260                 265                 270

Ile Thr Ala Cys Leu Trp Lys Cys Arg Thr Leu Ala Leu Asn Ile Asn
        275                 280                 285

Pro Lys Glu Ala Val Arg Val Ser Cys Ile Val Asn Ala Arg Gly Lys
    290                 295                 300

His Asn Asn Val Arg Leu Pro Leu Gly Tyr Tyr Gly Asn Ala Phe Ala
305                 310                 315                 320

Phe Pro Ala Ala Ile Ser Lys Ala Glu Pro Leu Cys Lys Asn Pro Leu
                325                 330                 335

Gly Tyr Ala Leu Glu Leu Val Lys Lys Ala Lys Ala Thr Met Asn Glu
            340                 345                 350

Glu Tyr Leu Arg Ser Val Ala Asp Leu Leu Val Leu Arg Gly Arg Pro
        355                 360                 365

Gln Tyr Ser Ser Thr Gly Ser Tyr Leu Ile Val Ser Asp Asn Thr Arg
    370                 375                 380

Ala Gly Phe Gly Asp Val Asn Phe Gly Trp Gly Gln Pro Val Phe Ala
385                 390                 395                 400
```

Gly Pro Ala Lys Ala Leu Asp Leu Ile Ser Phe Tyr Val Gln His Lys
            405                 410                 415

Asn Asn Thr Glu Asp Gly Ile Leu Val Pro Met Cys Leu Pro Ser Ser
        420                 425                 430

Ala Met Glu Arg Phe Gln Gln Glu Leu Glu Arg Ile Thr Gln Glu Pro
    435                 440                 445

Lys Glu Asp Ile Cys Asn Asn Leu Arg Ser Thr Arg Ile Met Ser Met
450                 455                 460

Met
465

<210> SEQ ID NO 11
<211> LENGTH: 1389
<212> TYPE: DNA
<213> ORGANISM: Clarkia breweri
<220> FEATURE:
<223> OTHER INFORMATION: BEBT

<400> SEQUENCE: 11

| | | | | | |
|---|---|---|---|---|---|
| atgcatcatc | accatcacca | cgctcacgac | caatctttgt | ctttcgaggt | ctgcagaaga | 60 |
| aagcccgagt | tgattagacc | agctaagcaa | actccacacg | agttcaagaa | gttgtccgac | 120 |
| gttgaagatc | aagagggtct | gagattccag | atcccagtca | tccaattcta | caagcacaac | 180 |
| aacgagtcca | tgcaagagag | agatccagtc | caggttatca | gagagggtat | cgctagagcc | 240 |
| ttggtctact | actacccatt | cgctggtaga | ttgagagagg | tcgacggtag | aaagttggtt | 300 |
| gttgagtgta | ctggtgaggg | tgtcatgttc | attgaagctg | acgctgacgt | taccttggag | 360 |
| caatttggtg | atgcattgca | gccaccattc | ccatgtttcg | accagttgtt | gttcgacgtt | 420 |
| ccaggttccg | gtggtatttt | ggactctcca | ttgctgttga | tccaggtcac | cagattgaag | 480 |
| tgcggttcct | tcatcttcgc | cttgagattg | aaccacacta | tggctgatgc | tgccggtatc | 540 |
| gtcttgttca | tgaaggctgt | tggtgagatg | gctagaggtg | ctgctactcc | atctactttg | 600 |
| ccagtttggg | acagacacat | cttgaacgct | agagttccac | acaggttac | cttcaaccac | 660 |
| agagagtacg | aagaggtcaa | gggaactatc | ttcactccat | cgatgacttt | ggcccacaga | 720 |
| tcctttttct | tcggttccac | tgaaatctcc | gccatgagaa | agcaaatccc | accacacttg | 780 |
| agatcctgtt | ccactaccat | cgaggttttg | actgcttgtt | gtggcgttg | tagaaccttg | 840 |
| gccattaagc | aaacccaga | cgaagaggtg | agaatgatct | gtatcgttaa | cgccagatcc | 900 |
| aagttcaacc | caccattgcc | agatggttac | tacggtaacg | cttcgctat | tccagctgct | 960 |
| gttactactg | ccggtaagtt | gtgtaacaac | ccattgggtt | tcgccttgga | gttgatcaga | 1020 |
| aaggccaaga | gagaggtcac | cgaagagtac | atgcattccg | ttgctgactt | gatggttgct | 1080 |
| actggtagac | acacttcac | cgttgtcaac | acctacttgg | tttccgacgt | tactagagct | 1140 |
| ggtttcggtg | aagttgattt | cggttggggt | gaagctgttt | acggtggtcc | agctaaaggt | 1200 |
| ggtgttggtg | ttattccagg | tgtcacctcc | ttctacatcc | cactgagaaa | cagacaaggt | 1260 |
| gagaagggta | tcgttctgcc | aatctgtttg | ccatccgctg | ccatggaaat | tttcgctgag | 1320 |
| gctttgaaca | cacccctgaa | cggtaaagag | atcgagatcg | ctaagcactt | cactcagtcc | 1380 |
| tccctgtaa | | | | | | 1389 |

<210> SEQ ID NO 12
<211> LENGTH: 462
<212> TYPE: PRT
<213> ORGANISM: Clarkia breweri

<220> FEATURE:
<223> OTHER INFORMATION: BEBT_AA

<400> SEQUENCE: 12

```
Met His His His His His Ala His Asp Gln Ser Leu Ser Phe Glu
1               5                   10                  15

Val Cys Arg Arg Lys Pro Glu Leu Ile Arg Pro Ala Lys Gln Thr Pro
            20                  25                  30

His Glu Phe Lys Lys Leu Ser Asp Val Glu Asp Gln Glu Gly Leu Arg
        35                  40                  45

Phe Gln Ile Pro Val Ile Gln Phe Tyr Lys His Asn Asn Glu Ser Met
    50                  55                  60

Gln Glu Arg Asp Pro Val Gln Val Ile Arg Glu Gly Ile Ala Arg Ala
65                  70                  75                  80

Leu Val Tyr Tyr Tyr Pro Phe Ala Gly Arg Leu Arg Glu Val Asp Gly
                85                  90                  95

Arg Lys Leu Val Val Glu Cys Thr Gly Glu Gly Val Met Phe Ile Glu
            100                 105                 110

Ala Asp Ala Asp Val Thr Leu Glu Gln Phe Gly Asp Ala Leu Gln Pro
        115                 120                 125

Pro Phe Pro Cys Phe Asp Gln Leu Leu Phe Asp Val Pro Gly Ser Gly
    130                 135                 140

Gly Ile Leu Asp Ser Pro Leu Leu Leu Ile Gln Val Thr Arg Leu Lys
145                 150                 155                 160

Cys Gly Ser Phe Ile Phe Ala Leu Arg Leu Asn His Thr Met Ala Asp
                165                 170                 175

Ala Ala Gly Ile Val Leu Phe Met Lys Ala Val Gly Glu Met Ala Arg
            180                 185                 190

Gly Ala Ala Thr Pro Ser Thr Leu Pro Val Trp Asp Arg His Ile Leu
        195                 200                 205

Asn Ala Arg Val Pro Pro Gln Val Thr Phe Asn His Arg Glu Tyr Glu
    210                 215                 220

Glu Val Lys Gly Thr Ile Phe Thr Pro Phe Asp Asp Leu Ala His Arg
225                 230                 235                 240

Ser Phe Phe Phe Gly Ser Thr Glu Ile Ser Ala Met Arg Lys Gln Ile
                245                 250                 255

Pro Pro His Leu Arg Ser Cys Ser Thr Thr Ile Glu Val Leu Thr Ala
            260                 265                 270

Cys Leu Trp Arg Cys Arg Thr Leu Ala Ile Lys Pro Asn Pro Asp Glu
        275                 280                 285

Glu Val Arg Met Ile Cys Ile Val Asn Ala Arg Ser Lys Phe Asn Pro
    290                 295                 300

Pro Leu Pro Asp Gly Tyr Tyr Gly Asn Ala Phe Ala Ile Pro Ala Ala
305                 310                 315                 320

Val Thr Thr Ala Gly Lys Leu Cys Asn Asn Pro Leu Gly Phe Ala Leu
                325                 330                 335

Glu Leu Ile Arg Lys Ala Lys Arg Glu Val Thr Glu Glu Tyr Met His
            340                 345                 350

Ser Val Ala Asp Leu Met Val Ala Thr Gly Arg Pro His Phe Thr Val
        355                 360                 365

Val Asn Thr Tyr Leu Val Ser Asp Val Thr Arg Ala Gly Phe Gly Glu
    370                 375                 380

Val Asp Phe Gly Trp Gly Glu Ala Val Tyr Gly Gly Pro Ala Lys Gly
385                 390                 395                 400
```

```
Gly Val Gly Val Ile Pro Gly Val Thr Ser Phe Tyr Ile Pro Leu Arg
            405                 410                 415

Asn Arg Gln Gly Glu Lys Gly Ile Val Leu Pro Ile Cys Leu Pro Ser
            420                 425                 430

Ala Ala Met Glu Ile Phe Ala Glu Ala Leu Asn Asn Thr Leu Asn Gly
            435                 440                 445

Lys Glu Ile Glu Ile Ala Lys His Phe Thr Gln Ser Ser Leu
    450                 455                 460

<210> SEQ ID NO 13
<211> LENGTH: 1320
<212> TYPE: DNA
<213> ORGANISM: Clarkia breweri
<220> FEATURE:
<223> OTHER INFORMATION: CbBEAT

<400> SEQUENCE: 13
atgcatcatc accaccacca caacgttact atgcactcca agaagttgct gaagccatcc      60
atcccaactc caaaccactt gcagaagttg aacttgtcct gctggaccaa gatccagatc     120
ccattctacg tcggtttgat cttccactac gagactttgt ctgacaactc cgacatcacc     180
ttgtccaagt tggaatcttc cttgtccgag actctgacct tgtactacca tgttgccggt     240
agatacaacg gtactgactg tgttatcgag tgcaacgacc agggtattgg ttacgttgaa     300
actgccttcg acgttgagtt gcaccagttc ttgttgggtg aagagtccaa caacttggac     360
ttgttggttg gtttgtccgg tttcttgtcc gaaactgaga ctccaccatt ggctgctatc     420
cagctgaaca tgtttaagtg cggtggtttg gttatcggtg cccagttcaa ccacattatc     480
ggtgacatgt tcaccatgtc caccttcatg aactcttggg ctaaggcctg tagagtcggt     540
atcaaagaag ttgctcaccc aactttcggt ttggccccat gatgccatc tgccaaggtt     600
ttgaacattc caccaccacc atctttcgag ggtgtcaagt tcgtttccaa gaggttcgtg     660
ttcaacgaga acgccatcac cagattgaga aagaggcta ctgaagagga cggtgatggt     720
gatgacgacc aaaagaagaa gaggccatcc agagttgact tggttactgc cttcttgtcc     780
aagtccttga tcgagatgga ctgcgctaag aaagagcaga ctaagtccag accatccctg     840
atggttcaca tgatgaacct gagaaagaga actaagctgg ccttggagaa cgacgtttcc     900
ggtaacttct tcatcgttgt taacgccgag tccaagatca ctgttgctcc aaagatcact     960
gacttgaccg aatctttggg ttccgcttgt ggtgagatta tctccgaggt tgctaaggtt    1020
gacgacgctg aagttgtttc ctccatggtt ttgaactccg tccgtgagtt ctactacgaa    1080
tggggtaagg gtgagaagaa cgtgttcttg tacacctcct ggtgtagatt cccactgtac    1140
gaagttgatt tcggttgggg tatcccatcc ttggttgaca ctactgctgt tccattcggt    1200
ctgatcgttt tgatggatga agctccagct ggtgacggta ttgctgttag agcttgtttg    1260
tctgagcacg acatgatcca attccaacag caccaccagt gctgtcccta cgtttcttaa    1320

<210> SEQ ID NO 14
<211> LENGTH: 439
<212> TYPE: PRT
<213> ORGANISM: Clarkia breweri
<220> FEATURE:
<223> OTHER INFORMATION: CbBEAT_AA

<400> SEQUENCE: 14

Met His His His His His His Asn Val Thr Met His Ser Lys Lys Leu
1               5                   10                  15
```

-continued

```
Leu Lys Pro Ser Ile Pro Thr Pro Asn His Leu Gln Lys Leu Asn Leu
         20                  25                  30

Ser Leu Leu Asp Gln Ile Gln Ile Pro Phe Tyr Val Gly Leu Ile Phe
         35                  40                  45

His Tyr Glu Thr Leu Ser Asp Asn Ser Asp Ile Thr Leu Ser Lys Leu
 50                  55                  60

Glu Ser Ser Leu Ser Glu Thr Leu Thr Leu Tyr Tyr His Val Ala Gly
 65                  70                  75                  80

Arg Tyr Asn Gly Thr Asp Cys Val Ile Glu Cys Asn Asp Gln Gly Ile
             85                  90                  95

Gly Tyr Val Glu Thr Ala Phe Asp Val Glu Leu His Gln Phe Leu Leu
                100                 105                 110

Gly Glu Glu Ser Asn Asn Leu Asp Leu Leu Val Gly Leu Ser Gly Phe
            115                 120                 125

Leu Ser Glu Thr Glu Thr Pro Pro Leu Ala Ala Ile Gln Leu Asn Met
        130                 135                 140

Phe Lys Cys Gly Gly Leu Val Ile Gly Ala Gln Phe Asn His Ile Ile
145                 150                 155                 160

Gly Asp Met Phe Thr Met Ser Thr Phe Met Asn Ser Trp Ala Lys Ala
                165                 170                 175

Cys Arg Val Gly Ile Lys Glu Val Ala His Pro Thr Phe Gly Leu Ala
            180                 185                 190

Pro Leu Met Pro Ser Ala Lys Val Leu Asn Ile Pro Pro Pro Pro Ser
        195                 200                 205

Phe Glu Gly Val Lys Phe Val Ser Lys Arg Phe Val Phe Asn Glu Asn
    210                 215                 220

Ala Ile Thr Arg Leu Arg Lys Glu Ala Thr Glu Glu Asp Gly Asp Gly
225                 230                 235                 240

Asp Asp Asp Gln Lys Lys Lys Arg Pro Ser Arg Val Asp Leu Val Thr
                245                 250                 255

Ala Phe Leu Ser Lys Ser Leu Ile Glu Met Asp Cys Ala Lys Lys Glu
            260                 265                 270

Gln Thr Lys Ser Arg Pro Ser Leu Met Val His Met Met Asn Leu Arg
        275                 280                 285

Lys Arg Thr Lys Leu Ala Leu Glu Asn Asp Val Ser Gly Asn Phe Phe
290                 295                 300

Ile Val Val Asn Ala Glu Ser Lys Ile Thr Val Ala Pro Lys Ile Thr
305                 310                 315                 320

Asp Leu Thr Glu Ser Leu Gly Ser Ala Cys Gly Glu Ile Ile Ser Glu
                325                 330                 335

Val Ala Lys Val Asp Asp Ala Gly Val Val Ser Ser Met Val Leu Asn
            340                 345                 350

Ser Val Arg Glu Phe Tyr Tyr Glu Trp Gly Lys Gly Glu Lys Asn Val
        355                 360                 365

Phe Leu Tyr Thr Ser Trp Cys Arg Phe Pro Leu Tyr Glu Val Asp Phe
370                 375                 380

Gly Trp Gly Ile Pro Ser Leu Val Asp Thr Thr Ala Val Pro Phe Gly
385                 390                 395                 400

Leu Ile Val Leu Met Asp Glu Ala Pro Ala Gly Asp Gly Ile Ala Val
                405                 410                 415

Arg Ala Cys Leu Ser Glu His Asp Met Ile Gln Phe Gln Gln His His
            420                 425                 430
```

Gln Leu Leu Ser Tyr Val Ser
        435

<210> SEQ ID NO 15
<211> LENGTH: 1377
<212> TYPE: DNA
<213> ORGANISM: Fragaria x ananassa
<220> FEATURE:
<223> OTHER INFORMATION: SAAT

<400> SEQUENCE: 15

```
atgcatcatc accaccacca cgagaagatc gaggtttcca ttaactccaa gcacactatc      60
aagccttcca cttcctccac tccattgcag ccatacaagt tgactttgtt ggaccagttg     120
actccaccag cttacgttcc aatcgttttc ttctacccaa tcactgacca cgacttcaac     180
ttgccacaaa ctttggctga cttgagacag gctttgtccg agactttgac tttgtactac     240
ccattgtccg gtagagttaa gaacaacttg tacatcgacg acttcgaaga gggtgttcca     300
tacttggagg ctagagttaa ctgtgatatg actgacttct tgagattgag aaagatcgag     360
tgtttgaacg agttcgttcc aatcaagcca ttctccatgg aagctatctc cgacgagaga     420
taccctttgt gggtgttcca ggttaacgtt ttcgactccg gtatcgctat cggtgtttct     480
gtttcccaca gttgatcga cggtggtact gctgactgtt tcttgaagtc ttggggtgct     540
gttttcagag gttgtagaga gaacatcatc acccatcttt gtccgaggc tgctttgttg     600
tttccaccaa gagatgactt gccagagaag tacgttgacc agatggaagc tttgtggttc     660
gctggtaaga aggttgctac tagaagattc gttttcggtg ttaaggctat ctcctccatt     720
caggacgaag ctaagtctga gtctgttcca aagccatcca gagttcacgc tgttactggt     780
ttcttgtgga gcacttgat cgctgcttcc agagctttga cttctggtac tacttccact     840
agattgtcca ttgctgctca ggctgttaac ttgagaacta gaatgaacat ggaaactgtt     900
ttggacaacg ctactggtaa cttgttctgg tgggctcagg ctatttttgga gttgtctcac     960
actactccag agatctccga cttgaagttg tgtgacttgg ttaacttgtt gaacggttcc    1020
gttaagcagt gtaacggtga ctacttcgag actttcaagg gtaaagaggg ttacggtaga    1080
atgtgtgagt acttggactt ccagagaact atgtcctcca tggaaccagc tccagatatc    1140
tacttgttct cctcctggac taacttcttc aacccattgg atttcggttg gggtagaact    1200
tcctggattg tgttgctgg taagattgag tccgcttcct gtaagttcat cattttggtt    1260
ccaactcagt gtggttccgg tatcgaagct tgggttaact tggaagaaga gaagatggct    1320
atgttggagc aagacccaca cttcttggct ttggcttctc caaagacttt gatctaa       1377
```

<210> SEQ ID NO 16
<211> LENGTH: 458
<212> TYPE: PRT
<213> ORGANISM: Fragaria x ananassa
<220> FEATURE:
<223> OTHER INFORMATION: SAAT_AA

<400> SEQUENCE: 16

Met His His His His His Glu Lys Ile Glu Val Ser Ile Asn Ser
1               5                   10                  15

Lys His Thr Ile Lys Pro Ser Thr Ser Ser Thr Pro Leu Gln Pro Tyr
            20                  25                  30

Lys Leu Thr Leu Leu Asp Gln Leu Thr Pro Pro Ala Tyr Val Pro Ile
        35                  40                  45

Val Phe Phe Tyr Pro Ile Thr Asp His Asp Phe Asn Leu Pro Gln Thr

```
                  50                  55                  60
Leu Ala Asp Leu Arg Gln Ala Leu Ser Glu Thr Leu Thr Leu Tyr Tyr
 65                  70                  75                  80

Pro Leu Ser Gly Arg Val Lys Asn Asn Leu Tyr Ile Asp Asp Phe Glu
                 85                  90                  95

Glu Gly Val Pro Tyr Leu Glu Ala Arg Val Asn Cys Asp Met Thr Asp
                100                 105                 110

Phe Leu Arg Leu Arg Lys Ile Glu Cys Leu Asn Glu Phe Val Pro Ile
                115                 120                 125

Lys Pro Phe Ser Met Glu Ala Ile Ser Asp Glu Arg Tyr Pro Leu Leu
                130                 135                 140

Gly Val Gln Val Asn Val Phe Asp Ser Gly Ile Ala Ile Gly Val Ser
145                 150                 155                 160

Val Ser His Lys Leu Ile Asp Gly Gly Thr Ala Asp Cys Phe Leu Lys
                165                 170                 175

Ser Trp Gly Ala Val Phe Arg Gly Cys Arg Glu Asn Ile Ile His Pro
                180                 185                 190

Ser Leu Ser Glu Ala Ala Leu Leu Phe Pro Pro Arg Asp Asp Leu Pro
                195                 200                 205

Glu Lys Tyr Val Asp Gln Met Glu Ala Leu Trp Phe Ala Gly Lys Lys
                210                 215                 220

Val Ala Thr Arg Arg Phe Val Phe Gly Val Lys Ala Ile Ser Ser Ile
225                 230                 235                 240

Gln Asp Glu Ala Lys Ser Glu Ser Val Pro Lys Pro Ser Arg Val His
                245                 250                 255

Ala Val Thr Gly Phe Leu Trp Lys His Leu Ile Ala Ala Ser Arg Ala
                260                 265                 270

Leu Thr Ser Gly Thr Thr Ser Thr Arg Leu Ser Ile Ala Ala Gln Ala
                275                 280                 285

Val Asn Leu Arg Thr Arg Met Asn Met Glu Thr Val Leu Asp Asn Ala
                290                 295                 300

Thr Gly Asn Leu Phe Trp Trp Ala Gln Ala Ile Leu Glu Leu Ser His
305                 310                 315                 320

Thr Thr Pro Glu Ile Ser Asp Leu Lys Leu Cys Asp Leu Val Asn Leu
                325                 330                 335

Leu Asn Gly Ser Val Lys Gln Cys Asn Gly Asp Tyr Phe Glu Thr Phe
                340                 345                 350

Lys Gly Lys Glu Gly Tyr Gly Arg Met Cys Glu Tyr Leu Asp Phe Gln
                355                 360                 365

Arg Thr Met Ser Ser Met Glu Pro Ala Pro Asp Ile Tyr Leu Phe Ser
                370                 375                 380

Ser Trp Thr Asn Phe Phe Asn Pro Leu Asp Phe Gly Trp Gly Arg Thr
385                 390                 395                 400

Ser Trp Ile Gly Val Ala Gly Lys Ile Glu Ser Ala Ser Cys Lys Phe
                405                 410                 415

Ile Ile Leu Val Pro Thr Gln Cys Gly Ser Gly Ile Glu Ala Trp Val
                420                 425                 430

Asn Leu Glu Glu Glu Lys Met Ala Met Leu Glu Gln Asp Pro His Phe
                435                 440                 445

Leu Ala Leu Ala Ser Pro Lys Thr Leu Ile
450                 455

<210> SEQ ID NO 17
```

<211> LENGTH: 1194
<212> TYPE: DNA
<213> ORGANISM: Fragaria x ananassa
<220> FEATURE:
<223> OTHER INFORMATION: Fa-AAT2

<400> SEQUENCE: 17

```
atgcatcatc accaccacca ctcctacaag aacaaccact ccattttgtc caagccaaac    60
gacccagttg aggttatcag agatgctttg tccaaggctt tgcagttcta ctacccattg   120
gctggtagat tgagagaggg tccaaacaag aaattgatgg ttgactgtac tggtgagggt   180
atcttgttcg ttgaagctaa cgctgaggtt actttggacg aattgggtga cgctatcttg   240
ccaccatgtc cattcttgga cggtttcttg ttcaacgttc caggttccga cggtattttg   300
ggttccccat tgtgtttgat ccaggttact agattgtcct gtggtggttt catcttcgct   360
ttgagattga accacactat ctgtgacgct ttgggtttgg ttcagttctt gaacgctgtt   420
ggtgagatcg ctcagggtaa atacgctcca tccattactc cagtttggga gagagagttg   480
ttgtccgcta gagatccacc aagaatctct tgtactcacg aagagttcga cgactccatt   540
gaccactctt acccaaacta cggtgctact gttcagcagt gttactgttt cggtccaaaa   600
gagatcaagt ccttgagaga gcatttgcca ccacacttgt ctacttgttc ctccactttc   660
gagttgatca ctgcttgtgt ttggaagtgt agaactatct ccttggacat ggacccagag   720
cagatcgtta gattgtcttg tgttgttact gctttgggta agcacaacaa cgtttgtttg   780
ccattgggtt actacggtaa cactttcact tacccagctg ttgtttccac tgctgagaga   840
ttgtgtaact cccctttggg ttacgctgtt gagtggttag agaaatccaa ggctaagatg   900
tccgaagagt acttgagatc cgctatcgac ttcgttgagg ttagaggtag accaccattc   960
gctttggaag gtatgtccga cttcttggtt tccgacaaca ctagaactgg tttgggtgag  1020
atcgacttcg gtttcggtaa gccagtttac gctggtgttg ctaagtccac tgacttgatc  1080
tcattctacg ttagatccac taacaaagaa gagagagaga ttttggttcc agtttgtttg  1140
cctatcttgt ccatggaaat cttccagcaa gagttgaaga agatgatcgg ttag        1194
```

<210> SEQ ID NO 18
<211> LENGTH: 397
<212> TYPE: PRT
<213> ORGANISM: Fragaria x ananassa
<220> FEATURE:
<223> OTHER INFORMATION: Fa-AAT2_AA

<400> SEQUENCE: 18

```
Met His His His His His His Ser Tyr Lys Asn Asn His Ser Ile Leu
1               5                   10                  15

Ser Lys Pro Asn Asp Pro Val Glu Val Ile Arg Asp Ala Leu Ser Lys
            20                  25                  30

Ala Leu Gln Phe Tyr Tyr Pro Leu Ala Gly Arg Leu Arg Glu Gly Pro
        35                  40                  45

Asn Lys Lys Leu Met Val Asp Cys Thr Gly Glu Gly Ile Leu Phe Val
    50                  55                  60

Glu Ala Asn Ala Glu Val Thr Leu Asp Glu Leu Gly Asp Ala Ile Leu
65                  70                  75                  80

Pro Pro Cys Pro Phe Leu Asp Gly Phe Leu Phe Asn Val Pro Gly Ser
                85                  90                  95

Asp Gly Ile Leu Gly Ser Pro Leu Cys Leu Ile Gln Val Thr Arg Leu
            100                 105                 110
```

```
Ser Cys Gly Gly Phe Ile Phe Ala Leu Arg Leu Asn His Thr Ile Cys
        115                 120                 125

Asp Ala Leu Gly Leu Val Gln Phe Leu Asn Ala Val Gly Glu Ile Ala
    130                 135                 140

Gln Gly Lys Tyr Ala Pro Ser Ile Thr Pro Val Trp Glu Arg Glu Leu
145                 150                 155                 160

Leu Ser Ala Arg Asp Pro Arg Ile Ser Cys Thr His Glu Glu Phe
                165                 170                 175

Asp Asp Ser Ile Asp His Ser Tyr Pro Asn Tyr Gly Ala Thr Val Gln
            180                 185                 190

Gln Cys Tyr Cys Phe Gly Pro Lys Glu Ile Lys Ser Leu Arg Glu His
        195                 200                 205

Leu Pro Pro His Leu Ser Thr Cys Ser Ser Thr Phe Glu Leu Ile Thr
    210                 215                 220

Ala Cys Val Trp Lys Cys Arg Thr Ile Ser Leu Asp Met Asp Pro Glu
225                 230                 235                 240

Gln Ile Val Arg Leu Ser Cys Val Val Thr Ala Leu Gly Lys His Asn
                245                 250                 255

Asn Val Cys Leu Pro Leu Gly Tyr Tyr Gly Asn Thr Phe Thr Tyr Pro
            260                 265                 270

Ala Val Val Ser Thr Ala Glu Arg Leu Cys Asn Ser Pro Leu Gly Tyr
        275                 280                 285

Ala Val Glu Leu Val Lys Lys Ser Lys Ala Lys Met Ser Glu Glu Tyr
    290                 295                 300

Leu Arg Ser Ala Ile Asp Phe Val Glu Val Arg Gly Arg Pro Pro Phe
305                 310                 315                 320

Ala Leu Glu Gly Met Ser Asp Phe Leu Val Ser Asp Asn Thr Arg Thr
                325                 330                 335

Gly Leu Gly Glu Ile Asp Phe Gly Phe Gly Lys Pro Val Tyr Ala Gly
            340                 345                 350

Val Ala Lys Ser Thr Asp Leu Ile Ser Phe Tyr Val Arg Ser Thr Asn
        355                 360                 365

Lys Glu Glu Arg Glu Ile Leu Val Pro Val Cys Leu Pro Ile Leu Ser
    370                 375                 380

Met Glu Ile Phe Gln Gln Glu Leu Lys Lys Met Ile Gly
385                 390                 395
```

<210> SEQ ID NO 19
<211> LENGTH: 1317
<212> TYPE: DNA
<213> ORGANISM: Actinidia eriantha
<220> FEATURE:
<223> OTHER INFORMATION: AeAT9

<400> SEQUENCE: 19

```
atgcaccatc accatcacca tgcctcctcc gtccgtctag tcaaaaagcc tgttttagtg      60
gcaccagttg acccaacacc atcaaccgtc ttgagccttt cctctctaga ctcgcaactg     120
ttcctccgat tccccattga gtatctgctt gtctatgctt ctccacatgg agtggatagg     180
gcagtcactg ctgcaagggt aaaagcagca ctggcaagat cattagtgcc atactatcct     240
ttggctggac gtgtgaaaac tagaccggat tctactggat tagacgttgt ctgtcaagct     300
caaggtgctg gtttgctgga ggcagttttct gactacacgg ctagtgactt tcaaagagcc     360
cccagatctg ttacagaatg gaggaagctg ctgttggtcg aagtctttaa ggttgtacct     420
ccactggtgg ttcaattaac ttggttatca gatggttgtg tagctttggg tgttggcttc     480
```

```
agtcactgtg taatcgatgg aattggttca agtgagtttt tgaaccttt tgctgagcta    540 gccacaggta gagctagatt gagcgaattt cagccaaaac ccgtttggga tagacattta    600
ctcaatagcg ctggtagaac aaatcttggt actcaccccg agttcggacg tgtgcctgat    660
ttgtcagggt tcgttacccg tttcactcag gaaagacttt cccctacctc gatcacattt    720
gataagacat ggttgaaaga gttgaaaaat attgcaatgt ccacttcaca acctggcgag    780
ttcccataca catcctttga ggtattgagc ggacatatct ggcgtagttg ggcccgttcg    840
ttgaatttgc cagctaaaca ggtattgaaa ctactcttct ccataaacat cagaaacaga    900
gttaagcctt ctttgcctgc gggatactat ggtaatgcat tgttctggg ttgtgctcaa     960 acatccgtta aggatcttac tgagaaagga ttgggttact gtgctgactt ggtcagaggt   1020
gctaaggaaa gagtgggtga tgaatatgcc agggaagtcg ttgagtcagt gagttggcca   1080
cgtagagcat ccccggactc cgtgggtgtg ttgatcatta gccaatggtc tagattagga   1140
ctggaccgtg ttgactttgg tttgggccgt cctgtacagg tgggtccaat tgttgcgat   1200 agatattgcc ttttcttgcc tgttagggaa tccacggaat ctgtgaaggt tatggttgct   1260
gttccaactt ctgctgttga cagatacgaa tacttcatca gatcaccata ctcctag       1317
```

```
<210> SEQ ID NO 20
<211> LENGTH: 438
<212> TYPE: PRT
<213> ORGANISM: Actinidia eriantha
<220> FEATURE:
<223> OTHER INFORMATION: AeAT9_AA

<400> SEQUENCE: 20
```

Met His His His His His Ala Ser Ser Val Arg Leu Val Lys Lys
1               5                   10                  15

Pro Val Leu Val Ala Pro Val Asp Pro Thr Pro Ser Thr Val Leu Ser
            20                  25                  30

Leu Ser Ser Leu Asp Ser Gln Leu Phe Leu Arg Phe Pro Ile Glu Tyr
        35                  40                  45

Leu Leu Val Tyr Ala Ser Pro His Gly Val Asp Arg Ala Val Thr Ala
    50                  55                  60

Ala Arg Val Lys Ala Ala Leu Ala Arg Ser Leu Val Pro Tyr Tyr Pro
65                  70                  75                  80

Leu Ala Gly Arg Val Lys Thr Arg Pro Asp Ser Thr Gly Leu Asp Val
                85                  90                  95

Val Cys Gln Ala Gln Gly Ala Gly Leu Leu Glu Ala Val Ser Asp Tyr
            100                 105                 110

Thr Ala Ser Asp Phe Gln Arg Ala Pro Arg Ser Val Thr Glu Trp Arg
        115                 120                 125

Lys Leu Leu Val Glu Val Phe Lys Val Val Pro Pro Leu Val Val
130                 135                 140

Gln Leu Thr Trp Leu Ser Asp Gly Cys Val Ala Leu Gly Val Gly Phe
145                 150                 155                 160

Ser His Cys Val Ile Asp Gly Ile Gly Ser Ser Glu Phe Leu Asn Leu
                165                 170                 175

Phe Ala Glu Leu Ala Thr Gly Arg Ala Arg Leu Ser Glu Phe Gln Pro
            180                 185                 190

Lys Pro Val Trp Asp Arg His Leu Leu Asn Ser Ala Gly Arg Thr Asn
        195                 200                 205

Leu Gly Thr His Pro Glu Phe Gly Arg Val Pro Asp Leu Ser Gly Phe

```
        210                 215                 220
Val Thr Arg Phe Thr Gln Glu Arg Leu Ser Pro Thr Ser Ile Thr Phe
225                 230                 235                 240

Asp Lys Thr Trp Leu Lys Glu Leu Lys Asn Ile Ala Met Ser Thr Ser
                245                 250                 255

Gln Pro Gly Glu Phe Pro Tyr Thr Ser Phe Glu Val Leu Ser Gly His
            260                 265                 270

Ile Trp Arg Ser Trp Ala Arg Ser Leu Asn Leu Pro Ala Lys Gln Val
        275                 280                 285

Leu Lys Leu Leu Phe Ser Ile Asn Ile Arg Asn Arg Val Lys Pro Ser
    290                 295                 300

Leu Pro Ala Gly Tyr Tyr Gly Asn Ala Phe Val Leu Gly Cys Ala Gln
305                 310                 315                 320

Thr Ser Val Lys Asp Leu Thr Glu Lys Gly Leu Gly Tyr Cys Ala Asp
                325                 330                 335

Leu Val Arg Gly Ala Lys Glu Arg Val Gly Asp Glu Tyr Ala Arg Glu
            340                 345                 350

Val Val Glu Ser Val Ser Trp Pro Arg Arg Ala Ser Pro Asp Ser Val
        355                 360                 365

Gly Val Leu Ile Ile Ser Gln Trp Ser Arg Leu Gly Leu Asp Arg Val
    370                 375                 380

Asp Phe Gly Leu Gly Arg Pro Val Gln Val Gly Pro Ile Cys Cys Asp
385                 390                 395                 400

Arg Tyr Cys Leu Phe Leu Pro Val Arg Glu Ser Thr Glu Ser Val Lys
                405                 410                 415

Val Met Val Ala Val Pro Thr Ser Ala Val Asp Arg Tyr Glu Tyr Phe
            420                 425                 430

Ile Arg Ser Pro Tyr Ser
            435

<210> SEQ ID NO 21
<211> LENGTH: 1392
<212> TYPE: DNA
<213> ORGANISM: Rosa hybrid cultivar
<220> FEATURE:
<223> OTHER INFORMATION: Rh-AAT1

<400> SEQUENCE: 21
atgcatcacc atcaccacca cgagaagatt gaggtttcca tcatctccag agacactatc      60
aagccttccg ctgcttcttc ttccttgcac ccatacaagt tgtccatcat cgaccagttc     120
actccaacta cttacttccc agttatcttc ttctacccaa tcactgacag agttttcaac     180
ttgccacaga ctttgactga cttgaagaac actgttcccc aggctttgac tttgtaccac     240
ccattgtccg gtagaatcaa gaacaacttg tacatcgacg acttcgaggc tggtatccca     300
tacttggaag ctagagttaa cttccacatg atcgatttct tgagattgcc aaagatcgag     360
tggttgaacg agttcgttcc aatggctcca tacagaaaag agactatctc cgagttcttg     420
cctttgttgg gtatccaggt taacatcttc gactccggta tcgctatcgg tgtttcattc     480
tcccacaaga tcaacgacgg tcagactgct tcctgtttct tgaagtcctg ggttgctatc     540
ttcagaggtt acagaaacaa gatcatccac ccaaacttgt cccaggctgc tttgttgttg     600
ccatccagag atgatttgcc agagaagtac gttgctatga tggaaagaat gtggttcggt     660
gagaagaagg ttgttactag aagattcgtt ttcgacgcta aggctatctc cgctttgcaa     720
gatgagggaa agtctgagta cgttccaaag ccttccagag ttcaagcttt gactggtttc     780
```

```
ttgtggaagc accagttggc tgcttctaga gctttgtcct ctggtacttc cactagattc    840
tccgttgctt cccagactgt taacttgaga tccaagatga acatgaagac tactttggac    900
aacgctatcg gaaatatctt cttgtgggct tccgctagat tggacttgaa cgatactgct    960
ccaggttcct ccgacttgaa gttgtgtgac ttggttaact tgttgaacga atccatcaaa   1020
gagttcaact ccgattactt ggagatcttg aagggtaaag agggttacgg tggtatgtgt   1080
gatttgttgg acttcatgga agagggttcc ttcgttgaac cagctccaga gttttactca   1140
ttctcctcat ggacaagatt cttcgaccag gttgatttcg gttggggtag accatcttgg   1200
gttggtttct ctggtagagt tgagactaga aacttcacta tcttcgttga gactcagtgt   1260
gacgacggta ttgacgcttg ggttactgtt gacgagaagc agatggctat gttggagcaa   1320
gacccacagt ttttggcttt cgcttctcca aacccaagaa tctctatcgc ttcctccgtt   1380
ggtatggact ag                                                        1392
```

<210> SEQ ID NO 22
<211> LENGTH: 463
<212> TYPE: PRT
<213> ORGANISM: Rosa hybrid cultivar
<220> FEATURE:
<223> OTHER INFORMATION: Rh-AAT1_AA

<400> SEQUENCE: 22

```
Met His His His His His Glu Lys Ile Glu Val Ser Ile Ile Ser
1               5                   10                  15

Arg Asp Thr Ile Lys Pro Ser Ala Ala Ser Ser Leu His Pro Tyr
            20                  25                  30

Lys Leu Ser Ile Ile Asp Gln Phe Thr Pro Thr Thr Tyr Phe Pro Val
        35                  40                  45

Ile Phe Phe Tyr Pro Ile Thr Asp Arg Val Phe Asn Leu Pro Gln Thr
    50                  55                  60

Leu Thr Asp Leu Lys Asn Thr Val Ser Gln Ala Leu Thr Leu Tyr His
65                  70                  75                  80

Pro Leu Ser Gly Arg Ile Lys Asn Asn Leu Tyr Ile Asp Asp Phe Glu
                85                  90                  95

Ala Gly Ile Pro Tyr Leu Glu Ala Arg Val Asn Phe His Met Ile Asp
            100                 105                 110

Phe Leu Arg Leu Pro Lys Ile Glu Trp Leu Asn Glu Phe Val Pro Met
        115                 120                 125

Ala Pro Tyr Arg Lys Glu Thr Ile Ser Glu Phe Leu Pro Leu Leu Gly
    130                 135                 140

Ile Gln Val Asn Ile Phe Asp Ser Gly Ile Ala Ile Gly Val Ser Phe
145                 150                 155                 160

Ser His Lys Ile Asn Asp Gly Gln Thr Ala Ser Cys Phe Leu Lys Ser
                165                 170                 175

Trp Val Ala Ile Phe Arg Gly Tyr Arg Asn Lys Ile Ile His Pro Asn
            180                 185                 190

Leu Ser Gln Ala Ala Leu Leu Leu Pro Ser Arg Asp Asp Leu Pro Glu
        195                 200                 205

Lys Tyr Val Ala Met Met Glu Arg Met Trp Phe Gly Glu Lys Lys Val
    210                 215                 220

Val Thr Arg Arg Phe Val Phe Asp Ala Lys Ala Ile Ser Ala Leu Gln
225                 230                 235                 240

Asp Glu Gly Lys Ser Glu Tyr Val Pro Lys Pro Ser Arg Val Gln Ala
```

-continued

```
                245                 250                 255
Leu Thr Gly Phe Leu Trp Lys His Gln Leu Ala Ala Ser Arg Ala Leu
            260                 265                 270

Ser Ser Gly Thr Ser Thr Arg Phe Ser Val Ala Ser Gln Thr Val Asn
        275                 280                 285

Leu Arg Ser Lys Met Asn Met Lys Thr Thr Leu Asp Asn Ala Ile Gly
    290                 295                 300

Asn Ile Phe Leu Trp Ala Ser Ala Arg Leu Asp Leu Asn Asp Thr Ala
305                 310                 315                 320

Pro Gly Ser Ser Asp Leu Lys Leu Cys Asp Leu Val Asn Leu Leu Asn
                325                 330                 335

Glu Ser Ile Lys Glu Phe Asn Ser Asp Tyr Leu Glu Ile Leu Lys Gly
            340                 345                 350

Lys Glu Gly Tyr Gly Gly Met Cys Asp Leu Leu Asp Phe Met Glu Glu
        355                 360                 365

Gly Ser Phe Val Glu Pro Ala Pro Glu Phe Tyr Ser Phe Ser Ser Trp
    370                 375                 380

Thr Arg Phe Phe Asp Gln Val Asp Phe Gly Trp Gly Arg Pro Ser Trp
385                 390                 395                 400

Val Gly Phe Ser Gly Arg Val Glu Thr Arg Asn Phe Thr Ile Phe Val
                405                 410                 415

Glu Thr Gln Cys Asp Asp Gly Ile Asp Ala Trp Val Thr Val Asp Glu
            420                 425                 430

Lys Gln Met Ala Met Leu Glu Gln Asp Pro Gln Phe Leu Ala Phe Ala
        435                 440                 445

Ser Pro Asn Pro Arg Ile Ser Ile Ala Ser Ser Val Gly Met Asp
    450                 455                 460
```

<210> SEQ ID NO 23
<211> LENGTH: 1458
<212> TYPE: DNA
<213> ORGANISM: Cucumis melo
<220> FEATURE:
<223> OTHER INFORMATION: CM-AAT4

<400> SEQUENCE: 23

```
atgcatcacc atcaccacca cgaggttaag gttttgtcca aagagactat catcccatcc      60
tccccaactc caccacactt gcaaccattg aacttgtcct tgttggacca gttgtcccca     120
atgttgtaca tccctttgtt gttgttctac ccaatgaaga agtcctacca gcaccaggat     180
cacaacaagg ctatcgctac tttgaaaact tccttgtcca agacttttgtc cagattctac     240
ttgttggctg gtagaatcat cggtaagtcc atccactgta acgacaaggg tgctgttttc     300
atggaagcta ctatcaactc caacatgttc gacatcttga agagccaaa caacgaggtt     360
ttgactaagt tgttgccatg ttctttgttg tgtaacacta agccaatcga agagtaccca     420
cagatcgttg ttcaggctaa catcttcgaa tgtggtggta tcgctatctc cttgtgtttg     480
ttgcacaagt tgatcgacgc tgctactttc tgttgtttct tgagatcctg ggctactaca     540
aacagagagt tgttgtcttt ggaccactct tcccccaaaca acaatatggt ttgtgttgac     600
tacaagtcct tctcctcctt gttccccacaa acaaacttgt tgcctttcca ccagtccttg     660
atcaacaacg ataaggctgt tgttccacca tcctccatct ttaacagaaa gagaagattc     720
cagagattcg ttttcagatc cgaggctatc ttggacttga aggctaaggc taagtcctgt     780
gacatcccaa acccaacttg tgttgagact ttgacttgtt tcatctggaa gtacttgatg     840
```

```
aaggttgctg acgacggtga ctctcaaaga ccatctactt tgtcccacgt tgttaacatc    900
agaaagatgt tggagccatc cttgggtgag gtttctttgg gtaacatcat gtggggtact    960
gttgctcacc acttctccac tactagaaac gaagagttcg agggtttgga gttgtccaag   1020
ttggtttcct tgttgagaca gtccttcaag aagattaaca aggactacat caaagaattg   1080
atcatgggtg gtgacaaaga aagaagaaac ggtgttatga agttggttgg tgagatcaac   1140
aagtggccaa tctccaacta ctacttcttc acttcctgga agaatttgaa gttgaacgag   1200
gttgacttcg gttgggggtaa gccattgtgg tctgctattg ctggtgaccc aaacgagatg   1260
atgggaaaca ttatcgtttt ggttgacaac gttttggacg acggttctac tgaggcttgg   1320 atttttgttgg acgagaaaga gatgcagttg ttggagcaga tcccacagtt tttggagttc   1380
gctttgttga acccatccat caacttgcca cacaaccaga aaactgctga cgagattttc   1440
tccaacaaat tgatctaa                                                 1458
```

<210> SEQ ID NO 24
<211> LENGTH: 485
<212> TYPE: PRT
<213> ORGANISM: Cucumis melo
<220> FEATURE:
<223> OTHER INFORMATION: CM-AAT4_AA

<400> SEQUENCE: 24

```
Met His His His His His Glu Val Lys Val Leu Ser Lys Glu Thr
1               5                   10                  15

Ile Ile Pro Ser Ser Pro Thr Pro His Leu Gln Pro Leu Asn Leu
                20                  25                  30

Ser Leu Leu Asp Gln Leu Ser Pro Met Leu Tyr Ile Pro Leu Leu Leu
            35                  40                  45

Phe Tyr Pro Met Lys Lys Ser Tyr Gln His Gln Asp His Asn Lys Ala
    50                  55                  60

Ile Ala Thr Leu Lys Thr Ser Leu Ser Lys Thr Leu Ser Arg Phe Tyr
65                  70                  75                  80

Leu Leu Ala Gly Arg Ile Ile Gly Lys Ser Ile His Cys Asn Asp Lys
                85                  90                  95

Gly Ala Val Phe Met Glu Ala Thr Ile Asn Ser Asn Met Phe Asp Ile
            100                 105                 110

Leu Lys Glu Pro Asn Asn Glu Val Leu Thr Lys Leu Leu Pro Cys Ser
        115                 120                 125

Leu Leu Cys Asn Thr Lys Pro Ile Glu Glu Tyr Pro Gln Ile Val Val
    130                 135                 140

Gln Ala Asn Ile Phe Glu Cys Gly Gly Ile Ala Ile Ser Leu Cys Leu
145                 150                 155                 160

Leu His Lys Leu Ile Asp Ala Ala Thr Phe Cys Cys Phe Leu Arg Ser
                165                 170                 175

Trp Ala Thr Thr Asn Arg Glu Leu Leu Ser Leu Asp His Ser Ser Pro
            180                 185                 190

Asn Asn Asn Met Val Cys Val Asp Tyr Lys Ser Phe Ser Ser Leu Phe
        195                 200                 205

Pro Gln Thr Asn Leu Leu Pro Phe His Gln Ser Leu Ile Asn Asn Asp
    210                 215                 220

Lys Ala Val Val Pro Pro Ser Ser Ile Phe Asn Arg Lys Arg Arg Phe
225                 230                 235                 240

Gln Arg Phe Val Phe Arg Ser Glu Ala Ile Leu Asp Leu Lys Ala Lys
                245                 250                 255
```

```
Ala Lys Ser Cys Asp Ile Pro Asn Pro Thr Cys Val Glu Thr Leu Thr
            260                 265                 270

Cys Phe Ile Trp Lys Tyr Leu Met Lys Val Ala Asp Gly Asp Ser
        275                 280                 285

Gln Arg Pro Ser Thr Leu Ser His Val Val Asn Ile Arg Lys Met Leu
    290                 295                 300

Glu Pro Ser Leu Gly Glu Val Ser Leu Gly Asn Ile Met Trp Gly Thr
305                 310                 315                 320

Val Ala His His Phe Ser Thr Thr Arg Asn Glu Glu Phe Glu Gly Leu
                325                 330                 335

Glu Leu Ser Lys Leu Val Ser Leu Leu Arg Gln Ser Phe Lys Lys Ile
            340                 345                 350

Asn Lys Asp Tyr Ile Lys Glu Leu Ile Met Gly Gly Asp Lys Glu Arg
        355                 360                 365

Arg Asn Gly Val Met Lys Leu Val Gly Glu Ile Asn Lys Trp Pro Ile
    370                 375                 380

Ser Asn Tyr Tyr Phe Phe Thr Ser Trp Lys Asn Leu Lys Leu Asn Glu
385                 390                 395                 400

Val Asp Phe Gly Trp Gly Lys Pro Leu Trp Ser Ala Ile Ala Gly Asp
                405                 410                 415

Pro Asn Glu Met Met Gly Asn Ile Ile Val Leu Val Asp Asn Val Leu
            420                 425                 430

Asp Asp Gly Ser Thr Glu Ala Trp Ile Leu Leu Asp Glu Lys Glu Met
        435                 440                 445

Gln Leu Leu Glu Gln Ile Pro Gln Phe Leu Glu Phe Ala Leu Leu Asn
    450                 455                 460

Pro Ser Ile Asn Leu Pro His Asn Gln Lys Thr Ala Asp Glu Ile Phe
465                 470                 475                 480

Ser Asn Lys Leu Ile
            485

<210> SEQ ID NO 25
<211> LENGTH: 669
<212> TYPE: DNA
<213> ORGANISM: Staphylococcus sciuri
<220> FEATURE:
<223> OTHER INFORMATION: ACT

<400> SEQUENCE: 25
atgcatcatc accatcacca caactttaat aaaattgatt tagacaattg gaagagaaaa      60
gagatattta atcattattt gaaccaacaa acgactttta gtataaccac agaaattgat     120
attagtgttt taccgaaa cataaaacaa gaaggatata aattttaccc tgcatttatt     180
ttcttagtga caagggtgat aaactcaaat acagctttta gaactggtta caatagcgac     240
ggagagttag gttattggga taagttagag ccacttttata caattttttga tggtgtatct     300 aaaacattct ctggtatttg gactcctgta aagaatgact tcaaagagtt ttatgattta     360
tacctttctg atgtagagaa atataatggt tcggggaaat tgtttcccaa acacctata      420 cctgaaaatg cttttttctct ttctattatt ccatggactt catttactgg gtttaactta     480
aatatcaata ataatagtaa ttaccttcta cccattatta cagcaggaaa attcattaat     540
aaaggtaatt caatatattt accgctatct ttacaggtac atcattctgt ttgtgatggt     600
tatcatgcag gattgtttat gaactctatt caggaattgt cagataggcc taatgactgg     660
cttttataa                                                             669
```

<210> SEQ ID NO 26
<211> LENGTH: 222
<212> TYPE: PRT
<213> ORGANISM: Staphylococcus sciuri
<220> FEATURE:
<223> OTHER INFORMATION: ACT_AA

<400> SEQUENCE: 26

Met His His His His His Asn Phe Asn Lys Ile Asp Leu Asp Asn
1               5                   10                  15

Trp Lys Arg Lys Glu Ile Phe Asn His Tyr Leu Asn Gln Gln Thr Thr
            20                  25                  30

Phe Ser Ile Thr Thr Glu Ile Asp Ile Ser Val Leu Tyr Arg Asn Ile
        35                  40                  45

Lys Gln Glu Gly Tyr Lys Phe Tyr Pro Ala Phe Ile Phe Leu Val Thr
    50                  55                  60

Arg Val Ile Asn Ser Asn Thr Ala Phe Arg Thr Gly Tyr Asn Ser Asp
65                  70                  75                  80

Gly Glu Leu Gly Tyr Trp Asp Lys Leu Glu Pro Leu Tyr Thr Ile Phe
                85                  90                  95

Asp Gly Val Ser Lys Thr Phe Ser Gly Ile Trp Thr Pro Val Lys Asn
            100                 105                 110

Asp Phe Lys Glu Phe Tyr Asp Leu Tyr Leu Ser Asp Val Glu Lys Tyr
        115                 120                 125

Asn Gly Ser Gly Lys Leu Phe Pro Lys Thr Pro Ile Pro Glu Asn Ala
    130                 135                 140

Phe Ser Leu Ser Ile Ile Pro Trp Thr Ser Phe Thr Gly Phe Asn Leu
145                 150                 155                 160

Asn Ile Asn Asn Asn Ser Asn Tyr Leu Leu Pro Ile Ile Thr Ala Gly
                165                 170                 175

Lys Phe Ile Asn Lys Gly Asn Ser Ile Tyr Leu Pro Leu Ser Leu Gln
            180                 185                 190

Val His His Ser Val Cys Asp Gly Tyr His Ala Gly Leu Phe Met Asn
        195                 200                 205

Ser Ile Gln Glu Leu Ser Asp Arg Pro Asn Asp Trp Leu Leu
    210                 215                 220

<210> SEQ ID NO 27
<211> LENGTH: 1278
<212> TYPE: DNA
<213> ORGANISM: Musa sapientum
<220> FEATURE:
<223> OTHER INFORMATION: BanAAT

<400> SEQUENCE: 27
atgcatcacc accaccacca ttccttcgct gttactagaa cttccagatc cttggttacc     60
ccatgtggtg ttactccaac tggttctttg ggtttgtccg ccattgatag agtcccaggt    120
ttgagacaca tggtcagatc cttgcacgtt ttcagacaag gtagagagcc agccagaatc    180
atcagagaag ctttgtccaa ggccctggtc aagtactacc catttgctgg tagattcgtt    240
gacgatcctg aaggtggtgg tgaggttaga gttgcttgta ctggtgaagg tgcctggttc    300
gttgaagcta aggctgactg ttctttggag acgtcaagt acttggacct gccattgatg    360
attccagagg acgctttgtt gccaaagcca tgtccaggtt tgaacccatt ggacttgcct    420
ttgatgttgc aggttaccga gtttgtcggt ggtggtttcg ttgttggttt gatctccgtt    480

```
cacactatcg ctgacggttt gggtgttgtc cagttcatta acgctgttgc tgagatcgct    540
agaggtttgc caaagcctac tgttgaacca gcttggtcca gagaggttat tccaaaccca    600
ccaaagttgc caccaggtgg tccaccagtt tttccatcct ttaagttgtt gcacgccacc    660
gttgatttgt ccccagatca cattgaccac gtcaagtcta gacacttgga gttgactggt    720
cagagatgtt ccactttcga cgttgctatc gctaacttgt ggcagtccag aactagagcc    780
attaacttgg atccaggtgt tgacgtccac gtctgtttct cgctaacaac agacacttg    840 ttgagacagg tcgttttgtt gccaccagag gatggttact acggtaactg tttctaccca    900
gttactgcta ctgctcccct cggtagaatt gcttctgctg agttgattga cgtcgtgtcc    960
atcatcagag atgccaagtc tagattgcca ggtgagtttg ctaaatgggc tgctggtgat   1020
ttcaaggacg acccatacga gttgtccttt acctacaact ccctgttcgt ttccgactgg   1080
actagattgg gtttcttgga cgttgattac ggttggggta agccattgca cgttatccca   1140
ttcgcttact tggacatcat ggccgttggt attattggtg ctccaccagc tccacaaaag   1200
ggtactagag ttatggctca gtgcgtcgag aaagaacaca tgcaagcttt cttggaagag   1260
atgaagggtt tcgcttaa                                                 1278
```

<210> SEQ ID NO 28
<211> LENGTH: 425
<212> TYPE: PRT
<213> ORGANISM: Musa sapientum
<220> FEATURE:
<223> OTHER INFORMATION: BanAAT_AA

<400> SEQUENCE: 28

```
Met His His His His His Ser Phe Ala Val Thr Arg Thr Ser Arg
1               5                   10                  15

Ser Leu Val Thr Pro Cys Gly Val Thr Pro Thr Gly Ser Leu Gly Leu
            20                  25                  30

Ser Ala Ile Asp Arg Val Pro Gly Leu Arg His Met Val Arg Ser Leu
        35                  40                  45

His Val Phe Arg Gln Gly Arg Glu Pro Ala Arg Ile Ile Arg Glu Ala
    50                  55                  60

Leu Ser Lys Ala Leu Val Lys Tyr Tyr Pro Phe Ala Gly Arg Phe Val
65                  70                  75                  80

Asp Asp Pro Glu Gly Gly Gly Glu Val Arg Val Ala Cys Thr Gly Glu
                85                  90                  95

Gly Ala Trp Phe Val Glu Ala Lys Ala Asp Cys Ser Leu Glu Asp Val
            100                 105                 110

Lys Tyr Leu Asp Leu Pro Leu Met Ile Pro Glu Asp Ala Leu Leu Pro
        115                 120                 125

Lys Pro Cys Pro Gly Leu Asn Pro Leu Asp Leu Pro Leu Met Leu Gln
    130                 135                 140

Val Thr Glu Phe Val Gly Gly Phe Val Gly Leu Ile Ser Val
145                 150                 155                 160

His Thr Ile Ala Asp Gly Leu Gly Val Val Gln Phe Ile Asn Ala Val
                165                 170                 175

Ala Glu Ile Ala Arg Gly Leu Pro Lys Pro Thr Val Glu Pro Ala Trp
            180                 185                 190

Ser Arg Glu Val Ile Pro Asn Pro Lys Leu Pro Pro Gly Gly Pro
        195                 200                 205

Pro Val Phe Pro Ser Phe Lys Leu Leu His Ala Thr Val Asp Leu Ser
    210                 215                 220
```

```
Pro Asp His Ile Asp His Val Lys Ser Arg His Leu Glu Leu Thr Gly
225                 230                 235                 240

Gln Arg Cys Ser Thr Phe Asp Val Ala Ile Ala Asn Leu Trp Gln Ser
                245                 250                 255

Arg Thr Arg Ala Ile Asn Leu Asp Pro Gly Val Asp Val His Val Cys
            260                 265                 270

Phe Phe Ala Asn Thr Arg His Leu Leu Arg Gln Val Val Leu Leu Pro
        275                 280                 285

Pro Glu Asp Gly Tyr Tyr Gly Asn Cys Phe Tyr Pro Val Thr Ala Thr
    290                 295                 300

Ala Pro Ser Gly Arg Ile Ala Ser Ala Glu Leu Ile Asp Val Val Ser
305                 310                 315                 320

Ile Ile Arg Asp Ala Lys Ser Arg Leu Pro Gly Glu Phe Ala Lys Trp
                325                 330                 335

Ala Ala Gly Asp Phe Lys Asp Asp Pro Tyr Glu Leu Ser Phe Thr Tyr
            340                 345                 350

Asn Ser Leu Phe Val Ser Asp Trp Thr Arg Leu Gly Phe Leu Asp Val
        355                 360                 365

Asp Tyr Gly Trp Gly Lys Pro Leu His Val Ile Pro Phe Ala Tyr Leu
    370                 375                 380

Asp Ile Met Ala Val Gly Ile Ile Gly Ala Pro Pro Ala Pro Gln Lys
385                 390                 395                 400

Gly Thr Arg Val Met Ala Gln Cys Val Glu Lys Glu His Met Gln Ala
                405                 410                 415

Phe Leu Glu Glu Met Lys Gly Phe Ala
                420                 425

<210> SEQ ID NO 29
<211> LENGTH: 1299
<212> TYPE: DNA
<213> ORGANISM: Zea mays
<220> FEATURE:
<223> OTHER INFORMATION: Glossy2

<400> SEQUENCE: 29
atgcatcatc accaccacca cgttttcgaa caacacgaag aagaggctgt tgctccaggt      60
gctgttcatg gtcatagatt gtctaccgtt gttccatcct ccgttactgg tgaagttgac     120
tacgctttgg ctgatgctga cttggctttc aagttgcact acctgagagg tgtctactac     180
tacagatctg gtgacggttt ggccaccaag gttttgaagg atccaatgtt gccatggctg     240
gatgaccact ttccagttgc tggtagagtt agaagggctg aaactgaagg tgatggtgct     300
ccaagacgtc cttacatcaa gtgtaacgac tgcggtgtta aatcgttga ggccagatgt      360 gatagagaca tggctgagtg gattagagat gctgctccag gtagaatcag acagttgtgt     420
tacgacaagg tcttgggtcc agagttgttc ttctccccat gctgtacgt tcagatcacc      480 aacttcaagt gtggtggttt ggctttgggt ttctcttggg ctcacttgat ggtgacatt      540 ccatccgctg ctacctgctt taacaagtgg gctcaaatcc tgtccggtaa gagccagaa      600 gctactgttt tgactccacc aaaccagcca ttgcaaggtc aatctccagc tgctccaaga     660
tccgttaagc aggttggtcc aattgaggac ttgtggttgg ttccagctgg tagagatatg     720
gcctgttact ctttccacgt ttccgacgcc gttttgaaga gttgcacca acaacagaac      780 ggtagacagg atgctgctgc tggtactttc gaattggttt ccgctttggt ttggcaggct     840
gttgctaaga ttagaggtga cgttgacacc gttaccgttg ttagagctga tgctgctggt     900
```

-continued

```
agatctggta agtctttggc caacgagatg aaggttggtt acgttgaatc tgctggatcc    960
tccccagcta agactgattt ggctgaattg gctgctttgc tggccaagaa cttggttgac   1020
gaaactgctg ctgttgctgc tttccaaggt gacgttttgg tttacggtgg tgccaacttg   1080
accttggttg acatggaaca ggttgacctg tacggtttgg agatcaaggg tcaaagacca   1140
gttcacgtcg aatacggtat ggatggtgtt ggtgatgagg tgctgtttt ggttcaacca    1200 gatgctgatg gtagaggtag attggttact gccgttttgc caggtgacga gattgactct   1260
ttgagagctg ctttgggttc cgccttgcag gttgcttaa                          1299
```

<210> SEQ ID NO 30
<211> LENGTH: 432
<212> TYPE: PRT
<213> ORGANISM: Zea mays
<220> FEATURE:
<223> OTHER INFORMATION: Glossy2_AA

<400> SEQUENCE: 30

```
Met His His His His His Val Phe Glu Gln His Glu Glu Glu Ala
1               5                   10                  15

Val Ala Pro Gly Ala Val His Gly His Arg Leu Ser Thr Val Val Pro
            20                  25                  30

Ser Ser Val Thr Gly Glu Val Asp Tyr Ala Leu Ala Asp Ala Asp Leu
        35                  40                  45

Ala Phe Lys Leu His Tyr Leu Arg Gly Val Tyr Tyr Arg Ser Gly
    50                  55                  60

Asp Gly Leu Ala Thr Lys Val Leu Lys Asp Pro Met Leu Pro Trp Leu
65                  70                  75                  80

Asp Asp His Phe Pro Val Ala Gly Arg Val Arg Arg Ala Glu Thr Glu
                85                  90                  95

Gly Asp Gly Ala Pro Arg Arg Pro Tyr Ile Lys Cys Asn Asp Cys Gly
            100                 105                 110

Val Arg Ile Val Glu Ala Arg Cys Asp Arg Asp Met Ala Glu Trp Ile
        115                 120                 125

Arg Asp Ala Ala Pro Gly Arg Ile Arg Gln Leu Cys Tyr Asp Lys Val
    130                 135                 140

Leu Gly Pro Glu Leu Phe Phe Ser Pro Leu Leu Tyr Val Gln Ile Thr
145                 150                 155                 160

Asn Phe Lys Cys Gly Gly Leu Ala Leu Gly Phe Ser Trp Ala His Leu
                165                 170                 175

Ile Gly Asp Ile Pro Ser Ala Ala Thr Cys Phe Asn Lys Trp Ala Gln
            180                 185                 190

Ile Leu Ser Gly Lys Lys Pro Glu Ala Thr Val Leu Thr Pro Pro Asn
        195                 200                 205

Gln Pro Leu Gln Gly Gln Ser Pro Ala Ala Pro Arg Ser Val Lys Gln
    210                 215                 220

Val Gly Pro Ile Glu Asp Leu Trp Leu Val Pro Ala Gly Arg Asp Met
225                 230                 235                 240

Ala Cys Tyr Ser Phe His Val Ser Asp Ala Val Leu Lys Lys Leu His
                245                 250                 255

Gln Gln Gln Asn Gly Arg Gln Asp Ala Ala Ala Gly Thr Phe Glu Leu
            260                 265                 270

Val Ser Ala Leu Val Trp Gln Ala Val Ala Lys Ile Arg Gly Asp Val
        275                 280                 285
```

```
Asp Thr Val Thr Val Arg Ala Asp Ala Ala Gly Arg Ser Gly Lys
    290                 295                 300

Ser Leu Ala Asn Glu Met Lys Val Gly Tyr Val Glu Ser Ala Gly Ser
305                 310                 315                 320

Ser Pro Ala Lys Thr Asp Leu Ala Glu Leu Ala Ala Leu Leu Ala Lys
                325                 330                 335

Asn Leu Val Asp Glu Thr Ala Ala Val Ala Ala Phe Gln Gly Asp Val
                340                 345                 350

Leu Val Tyr Gly Gly Ala Asn Leu Thr Leu Val Asp Met Glu Gln Val
        355                 360                 365

Asp Leu Tyr Gly Leu Glu Ile Lys Gly Gln Arg Pro Val His Val Glu
    370                 375                 380

Tyr Gly Met Asp Gly Val Gly Asp Glu Gly Ala Val Leu Val Gln Pro
385                 390                 395                 400

Asp Ala Asp Gly Arg Gly Arg Leu Val Thr Ala Val Leu Pro Gly Asp
                405                 410                 415

Glu Ile Asp Ser Leu Arg Ala Ala Leu Gly Ser Ala Leu Gln Val Ala
                420                 425                 430
```

<210> SEQ ID NO 31
<211> LENGTH: 1398
<212> TYPE: DNA
<213> ORGANISM: Cucumis melo
<220> FEATURE:
<223> OTHER INFORMATION: CM-AAT3

<400> SEQUENCE: 31

```
atgcatcatc atcaccacca cgcatcctcc ctggttttcc aagttcaaag atcccagcca      60
cagttgattc caccatctga tccaactcca cacgagttca agcagttgtc tgacattgac     120
gaccaagagg gtctgagatt ccagatccca gttatccagt ctacagaca cgacccaaga     180
atggctggta ctgatccagc cagagttatc aaagaggcta tcgctaaggc cctggttttc     240
tactacccat tcgctggtag attgagagag ggtccaggta gaaagttgtt cgttgagtgt     300
actggtgagg gtgtcatgtt cattgaagct gacgctgacg tttccttgga gcaatttggt     360
gatgcattgc agccaccatt cccatgtttg gaggaacctt tgttcgacgt tccaaactcc     420
tctggtgttt tggactgtcc attgctgttg atccaggtca ccagattgaa gtgcggtggt     480
ttcatcttcg ccttgagatt gaaccacact atgtctgacg cttccggttt ggtccaattc     540
atgatggctg ttggtgagat ggctagaggt gctactgctc catctgttag accagtttgg     600
cagagagctt gctgaacgc tagagatcca ccaaaggtta cctgtcacca gagaaatac     660
gacgaggttg ttgacaccaa gggtactatc attccattgg acgacatggc ccacagatcc     720
ttttttttcg gtccatccga aatctccgcc atcagaaagg ctttgccatc ccacttgaga     780
cagtgttcct cattcgaggt tttgaccgct gtctgtggc gtttcagaac tatttccttg     840
caaccagacc cagaggaaga ggttagagtt tgtgtatcg tcaactccag atccaagttc     900
aacccaccat tgccaactgg ttactacggt aacgctttcg ctttcccagt tgctttgact     960
actgccggta agttgtgtca gaacccattg ggttacgcct tggagttggt tagaaaggct    1020
aaggctgatg tcaccgagga ctacatgaag tctgttgccg acttgatggt catcaagggt    1080
agaccacact tcaccgttgt cagaacctac ttggtttccg acgttactag agctggtttc    1140
gaggatgttg attccggttg gggtaaggct atgtacggtg gtccagctaa ggttggtgtt    1200
ggtgctattc caggtgttgc ctctttctac atcccattca agaacaagaa gggcgagaga    1260
```

```
ggtatcttgg tcccattgtg tttaccagct ccagccatgg aaagattcgt caaagaattg    1320
gacgccttgc tgaaggctgg taagactatt gatggtgtcg acaacaagaa gcccctgttc    1380
attgcttccg ccttgtaa                                                   1398
```

<210> SEQ ID NO 32
<211> LENGTH: 465
<212> TYPE: PRT
<213> ORGANISM: Cucumis melo
<220> FEATURE:
<223> OTHER INFORMATION: CM-AAT3_AA

<400> SEQUENCE: 32

```
Met His His His His His Ala Ser Ser Leu Val Phe Gln Val Gln
1               5                   10                  15

Arg Ser Gln Pro Gln Leu Ile Pro Pro Ser Asp Pro Thr Pro His Glu
            20                  25                  30

Phe Lys Gln Leu Ser Asp Ile Asp Asp Gln Glu Gly Leu Arg Phe Gln
        35                  40                  45

Ile Pro Val Ile Gln Phe Tyr Arg His Asp Pro Arg Met Ala Gly Thr
    50                  55                  60

Asp Pro Ala Arg Val Ile Lys Glu Ala Ile Ala Lys Ala Leu Val Phe
65                  70                  75                  80

Tyr Tyr Pro Phe Ala Gly Arg Leu Arg Glu Gly Pro Gly Arg Lys Leu
                85                  90                  95

Phe Val Glu Cys Thr Gly Glu Gly Val Met Phe Ile Glu Ala Asp Ala
            100                 105                 110

Asp Val Ser Leu Glu Gln Phe Gly Asp Ala Leu Gln Pro Pro Phe Pro
        115                 120                 125

Cys Leu Glu Glu Pro Leu Phe Asp Val Pro Asn Ser Ser Gly Val Leu
    130                 135                 140

Asp Cys Pro Leu Leu Leu Ile Gln Val Thr Arg Leu Lys Cys Gly Gly
145                 150                 155                 160

Phe Ile Phe Ala Leu Arg Leu Asn His Thr Met Ser Asp Ala Ser Gly
                165                 170                 175

Leu Val Gln Phe Met Met Ala Val Gly Glu Met Ala Arg Gly Ala Thr
            180                 185                 190

Ala Pro Ser Val Arg Pro Val Trp Gln Arg Ala Leu Leu Asn Ala Arg
        195                 200                 205

Asp Pro Pro Lys Val Thr Cys His Arg Glu Tyr Asp Glu Val Val
    210                 215                 220

Asp Thr Lys Gly Thr Ile Ile Pro Leu Asp Asp Met Ala His Arg Ser
225                 230                 235                 240

Phe Phe Phe Gly Pro Ser Glu Ile Ser Ala Ile Arg Lys Ala Leu Pro
                245                 250                 255

Ser His Leu Arg Gln Cys Ser Ser Phe Glu Val Leu Thr Ala Cys Leu
            260                 265                 270

Trp Arg Phe Arg Thr Ile Ser Leu Gln Pro Asp Pro Glu Glu Val
        275                 280                 285

Arg Val Leu Cys Ile Val Asn Ser Arg Ser Lys Phe Asn Pro Pro Leu
    290                 295                 300

Pro Thr Gly Tyr Tyr Gly Asn Ala Phe Ala Phe Pro Val Ala Leu Thr
305                 310                 315                 320

Thr Ala Gly Lys Leu Cys Gln Asn Pro Leu Gly Tyr Ala Leu Glu Leu
                325                 330                 335
```

-continued

```
Val Arg Lys Ala Lys Ala Asp Val Thr Glu Asp Tyr Met Lys Ser Val
            340                 345                 350

Ala Asp Leu Met Val Ile Lys Gly Arg Pro His Phe Thr Val Val Arg
        355                 360                 365

Thr Tyr Leu Val Ser Asp Val Thr Arg Ala Gly Phe Glu Asp Val Asp
    370                 375                 380

Phe Gly Trp Gly Lys Ala Met Tyr Gly Gly Pro Ala Lys Gly Gly Val
385                 390                 395                 400

Gly Ala Ile Pro Gly Val Ala Ser Phe Tyr Ile Pro Phe Lys Asn Lys
                405                 410                 415

Lys Gly Glu Arg Gly Ile Leu Val Pro Leu Cys Leu Pro Ala Pro Ala
            420                 425                 430

Met Glu Arg Phe Val Lys Glu Leu Asp Ala Leu Leu Lys Ala Gly Lys
        435                 440                 445

Thr Ile Asp Gly Val Asp Asn Lys Lys Pro Leu Phe Ile Ala Ser Ala
    450                 455                 460

Leu
465
```

<210> SEQ ID NO 33
<211> LENGTH: 1464
<212> TYPE: DNA
<213> ORGANISM: Fusarium oxysporum
<220> FEATURE:
<223> OTHER INFORMATION: BAHDFox

<400> SEQUENCE: 33

```
atgcatcatc accatcacca cccatccact ttgaacttcc aatccgagac tccaactgtt     60
caaggtgaac aagacccatc cttggttacc ttggaacact acggattgca accaccatcc    120
gctcaacaaa agttgacccc attggacatg aacatgccaa gactgtacgg tatcagactg    180
atcttgtgct tcccaactaa cccaggtatg gacaagagac agatctacga gaacctgaag    240
aagggtttgg ctcacaccgt tacttccgtt ccatggattt ctggtcacat cggtccagaa    300
gaaggtcagg atccaaagac cagaaaggtc cagattttgg actccccata cggtttcaga    360
ttcccataca aggacttgac tgacgccttg ccaccatacg ctgaattgca agaaagaaac    420
ttcccactgg ctgagttcac tactgctcag gttggtccaa ttgacgttat gccacaaggt    480
ccaaaccagc cagtttttgc tgctcaggct aacttcgtta agggtggttt gttgttgacc    540
gttggtgttc accactctgc ttgtgatgct ttggctttgg acgctatctt gtctacttgg    600
tcccacaaca ctgctgttgc ttcaggtggt tctggttcct tctctacttt ggacggtcca    660
tctaacgaca gatccccatt gatggaaggt gacttgggta acgctgatgt tgctgctttc    720
cctgagtacg ttttgatgcc aactccacac tctactgagg gtgacttgtc ctctatgtcc    780
ggttttcaaa tgccaccatt ggcctctaga ctgttccact tctcaccaga gtccctgaga    840
aagttgaagg ctgaagctgg tgctttctct tctcacgatg ctttgtgtgc tttcatctgg    900
cagagaatga ccttggctag aatgcactcc ggtatcttca acgatccacc aggtgacttg    960
acctccagat tctgtttcgc cgtcaacatc agaaacagaa tgtccccacc attgccacca   1020
tcctacatgg gtaatgcttc catgggttgt gtcaccgaga agatttctgt tgcctccatg   1080
atctccaaca acggtttgaa gcaagcctcc gtcactatca gaagatccct gaacgatttc   1140
aactccccaa gaagggctac ttccaccatc ggtttgttga gatctagacc agacccaacc   1200
gacttcaagt tgtccttcaa cggtttcttg ggtccagacg ttgttgaatc ttcttgggct   1260
```

-continued

```
gacttgggtg tttacggtca tcaatggggt gacgctattg gtactttgga cgctgttaga    1320
atcccaggtg aaggttctga cggtactatg atgatcctgc aagattgaa ggacggtggt     1380 ttggacgttg ttgttggttt gtctactgct gccatggaaa gactgttgga ggacgaaaag    1440
ttcgtttccg ttgctcactc ttaa                                           1464
```

```
<210> SEQ ID NO 34
<211> LENGTH: 487
<212> TYPE: PRT
<213> ORGANISM: Fusarium oxysporum
<220> FEATURE:
<223> OTHER INFORMATION: BAHDFox_AA

<400> SEQUENCE: 34
```

```
Met His His His His His Pro Ser Thr Leu Asn Phe Gln Ser Glu
1               5                   10                  15

Thr Pro Thr Val Gln Gly Glu Gln Asp Pro Ser Leu Val Thr Leu Glu
            20                  25                  30

His Tyr Gly Leu Gln Pro Pro Ser Ala Gln Gln Lys Leu Thr Pro Leu
        35                  40                  45

Asp Met Asn Met Pro Arg Leu Tyr Gly Ile Arg Leu Ile Leu Cys Phe
50                  55                  60

Pro Thr Asn Pro Gly Met Asp Lys Arg Gln Ile Tyr Glu Asn Leu Lys
65                  70                  75                  80

Lys Gly Leu Ala His Thr Val Thr Ser Val Pro Trp Ile Ser Gly His
                85                  90                  95

Ile Gly Pro Glu Glu Gly Gln Asp Pro Lys Thr Arg Lys Val Gln Ile
            100                 105                 110

Leu Asp Ser Pro Tyr Gly Phe Arg Phe Pro Tyr Lys Asp Leu Thr Asp
        115                 120                 125

Ala Leu Pro Pro Tyr Ala Glu Leu Gln Glu Arg Asn Phe Pro Leu Ala
    130                 135                 140

Glu Phe Thr Thr Ala Gln Val Gly Pro Ile Asp Val Met Pro Gln Gly
145                 150                 155                 160

Pro Asn Gln Pro Val Phe Ala Ala Gln Ala Asn Phe Val Lys Gly Gly
                165                 170                 175

Leu Leu Leu Thr Val Gly Val His Ser Ala Cys Asp Ala Leu Ala
            180                 185                 190

Leu Asp Ala Ile Leu Ser Thr Trp Ser His Asn Thr Ala Val Ala Ser
        195                 200                 205

Gly Gly Ser Gly Ser Phe Ser Thr Leu Asp Gly Pro Ser Asn Asp Arg
    210                 215                 220

Ser Pro Leu Met Glu Gly Asp Leu Gly Asn Ala Asp Val Ala Ala Phe
225                 230                 235                 240

Pro Glu Tyr Val Leu Met Pro Thr Pro His Ser Thr Glu Gly Asp Leu
                245                 250                 255

Ser Ser Met Ser Gly Phe Gln Met Pro Pro Leu Ala Ser Arg Leu Phe
            260                 265                 270

His Phe Ser Pro Glu Ser Leu Arg Lys Leu Lys Ala Glu Ala Gly Ala
        275                 280                 285

Phe Ser Ser His Asp Ala Leu Cys Ala Phe Ile Trp Gln Arg Met Thr
    290                 295                 300

Leu Ala Arg Met His Ser Gly Ile Phe Asn Asp Pro Pro Gly Asp Leu
305                 310                 315                 320

Thr Ser Arg Phe Cys Phe Ala Val Asn Ile Arg Asn Arg Met Ser Pro
```

```
                    325                 330                 335
Pro Leu Pro Pro Ser Tyr Met Gly Asn Ala Ser Met Gly Cys Val Thr
            340                 345                 350

Glu Lys Ile Ser Val Ala Ser Met Ile Ser Asn Asn Gly Leu Lys Gln
            355                 360                 365

Ala Ser Val Thr Ile Arg Arg Ser Leu Asn Asp Phe Asn Ser Pro Arg
370                 375                 380

Arg Ala Thr Ser Thr Ile Gly Leu Leu Arg Ser Arg Pro Asp Pro Thr
385                 390                 395                 400

Asp Phe Lys Leu Ser Phe Asn Gly Phe Leu Gly Pro Asp Val Val Glu
            405                 410                 415

Ser Ser Trp Ala Asp Leu Gly Val Tyr Gly His Gln Trp Gly Asp Ala
            420                 425                 430

Ile Gly Thr Leu Asp Ala Val Arg Ile Pro Gly Glu Gly Ser Asp Gly
            435                 440                 445

Thr Met Met Ile Leu Pro Arg Leu Lys Asp Gly Leu Asp Val Val
            450                 455                 460

Val Gly Leu Ser Thr Ala Ala Met Glu Arg Leu Leu Glu Asp Glu Lys
465                 470                 475                 480

Phe Val Ser Val Ala His Ser
            485

<210> SEQ ID NO 35
<211> LENGTH: 1410
<212> TYPE: DNA
<213> ORGANISM: Vasconcellea pubescens
<220> FEATURE:
<223> OTHER INFORMATION: VpAAT1

<400> SEQUENCE: 35
atgcatcatc accaccacca tgctgaaaag gcctcttctc tgatgttcaa cgttagaagg      60
cacgagccag agttgatcac tccagctaaa cctactccaa gagagatcaa gttgctgtcc     120
gacattgatg accaggacgg tttgagattc caggtcccaa ttatccagtt ctacaagaac     180
aactcctcca tgcagggtaa gaacccagcc aagattatca gtctgctttt ggccgagact     240
ctggtccatt actatccatt ggctggtaga ctgagagagg gtttcggtag aaagttgatg     300
gttgagtgta ccggtgaggg tatcttgttc attgaagctg atgccgacgt taccttgcac     360
gaatttggtg atgatctgcc accaccattc ccatgtttgg tcgagttgtt gtacgacgtt     420
ccaggttcct ccggtattat cgacactcca ttgctgttga tccaggtcac cagattgaag     480
tgcggtggtt tcatcttcgc cttgagattg aaccacacta tgtctgacgc ttccggtttg     540
gttcagttca tgactgctgt tggtgagatg gctagaggtc aaagatcctt gtccattcag     600
ccagtttggg agagacactt gttgaacgct agagatccac caagagttac ccacattcac     660
cacgaatacg atgacttgga ggacaccaag ggtactatca ttccattgga cgacatggtc     720
cacaggtcct ttttttccgg tccatccgaa atggccgcca tcagaagatt ggttccagct     780
cactttcaca gatccactac ctccgaagtt ttgaccgctt acttgtggcg ttgttacact     840
attgccttgc aaccagaccc agaggaagag atgagagtta tctgtgtcgt caactccagg     900
accaagttga acccaccatt gccaactggt ttctacggta acggtattgc ttccccagct     960
gctatctccc aggctaagaa gatttgcgaa aacccattcg ttacaccct gcagttggtt    1020 aagcagacca aggttgacgt taccgaagag tacatgagat ccgctgctga cttgatggct    1080
atgaagggta gaccacactt taccgtcgtt agaaggtaca tggtttccga cgttactaga    1140
```
gccggtttcg gtttggttga tttcggttgg ggtagaccag aaccagttta tggtggtcca    1200
gctaagggtg gtgttggtcc aattccaggt gttacctcat tcttcgtccc attcaagaac    1260
agaaagggtg agaagggtat cgttgtccca acttgtttgc caactccagc catggaaaga    1320
ttcgccaagt tgatgaacga gatcctgcag aaccagttgt tggtttccgc tgaagagaac    1380
aagtccgtgt tcatcgtttc cgctatctaa    1410

<210> SEQ ID NO 36
<211> LENGTH: 469
<212> TYPE: PRT
<213> ORGANISM: Vasconcellea pubescens
<220> FEATURE:
<223> OTHER INFORMATION: VpAAT1_AA

<400> SEQUENCE: 36

Met His His His His His Ala Glu Lys Ala Ser Ser Leu Met Phe
1               5                   10                  15

Asn Val Arg Arg His Glu Pro Glu Leu Ile Thr Pro Ala Lys Pro Thr
            20                  25                  30

Pro Arg Glu Ile Lys Leu Leu Ser Asp Ile Asp Asp Gln Asp Gly Leu
        35                  40                  45

Arg Phe Gln Val Pro Ile Ile Gln Phe Tyr Lys Asn Asn Ser Ser Met
    50                  55                  60

Gln Gly Lys Asn Pro Ala Lys Ile Ile Lys Ser Ala Leu Ala Glu Thr
65                  70                  75                  80

Leu Val His Tyr Tyr Pro Leu Ala Gly Arg Leu Arg Glu Gly Phe Gly
                85                  90                  95

Arg Lys Leu Met Val Glu Cys Thr Gly Glu Gly Ile Leu Phe Ile Glu
            100                 105                 110

Ala Asp Ala Asp Val Thr Leu His Glu Phe Gly Asp Asp Leu Pro Pro
        115                 120                 125

Pro Phe Pro Cys Leu Val Glu Leu Leu Tyr Asp Val Pro Gly Ser Ser
    130                 135                 140

Gly Ile Ile Asp Thr Pro Leu Leu Leu Ile Gln Val Thr Arg Leu Lys
145                 150                 155                 160

Cys Gly Gly Phe Ile Phe Ala Leu Arg Leu Asn His Thr Met Ser Asp
                165                 170                 175

Ala Ser Gly Leu Val Gln Phe Met Thr Ala Val Gly Glu Met Ala Arg
            180                 185                 190

Gly Gln Arg Ser Leu Ser Ile Gln Pro Val Trp Glu Arg His Leu Leu
        195                 200                 205

Asn Ala Arg Asp Pro Pro Arg Val Thr His Ile His His Glu Tyr Asp
    210                 215                 220

Asp Leu Glu Asp Thr Lys Gly Thr Ile Ile Pro Leu Asp Asp Met Val
225                 230                 235                 240

His Arg Ser Phe Phe Gly Pro Ser Glu Met Ala Ala Ile Arg Arg
                245                 250                 255

Leu Val Pro Ala His Phe His Arg Ser Thr Thr Ser Glu Val Leu Thr
            260                 265                 270

Ala Tyr Leu Trp Arg Cys Tyr Thr Ile Ala Leu Gln Pro Asp Pro Glu
        275                 280                 285

Glu Glu Met Arg Val Ile Cys Val Val Asn Ser Arg Thr Lys Leu Asn
    290                 295                 300

Pro Pro Leu Pro Thr Gly Phe Tyr Gly Asn Gly Ile Ala Phe Pro Ala

```
                305                 310                 315                 320
Ala Ile Ser Gln Ala Lys Lys Ile Cys Glu Asn Pro Phe Gly Tyr Thr
                    325                 330                 335

Leu Gln Leu Val Lys Gln Thr Lys Val Asp Val Thr Glu Glu Tyr Met
                340                 345                 350

Arg Ser Ala Ala Asp Leu Met Ala Met Lys Gly Arg Pro His Phe Thr
            355                 360                 365

Val Val Arg Arg Tyr Met Val Ser Asp Val Thr Arg Ala Gly Phe Gly
        370                 375                 380

Leu Val Asp Phe Gly Trp Gly Arg Pro Glu Pro Val Tyr Gly Gly Pro
385                 390                 395                 400

Ala Lys Gly Gly Val Gly Pro Ile Pro Gly Val Thr Ser Phe Phe Val
                405                 410                 415

Pro Phe Lys Asn Arg Lys Gly Glu Lys Gly Ile Val Val Pro Thr Cys
            420                 425                 430

Leu Pro Thr Pro Ala Met Glu Arg Phe Ala Lys Leu Met Asn Glu Ile
        435                 440                 445

Leu Gln Asn Gln Leu Leu Val Ser Ala Glu Glu Asn Lys Ser Val Phe
    450                 455                 460

Ile Val Ser Ala Ile
465

<210> SEQ ID NO 37
<211> LENGTH: 1368
<212> TYPE: DNA
<213> ORGANISM: Vitis labrusca
<220> FEATURE:
<223> OTHER INFORMATION: AMAT

<400> SEQUENCE: 37
atgcatcatc accaccatca cgcttctcca tcttccccat tggtttttctc cgttaacaga       60 tgcgttcccc agatcgttag accagctaac ccaactccaa gagaggttaa gcagttgtcc      120
gacattgacg accaagaggg tagaagattc cagatcccag tcatcatgtt ctacagaaac      180
aaccccctga tggaaggtaa ggacccagtt aaggttatca gagaggcttt gggtaaggcc      240
ctggtttact actacccatt cgctggtaga ttgatcgagg gtgacaacag aaagttgatg      300
gttgactgta ccggtgaggg tgtcttgttc attgaagctg atgctgacac cacccttggag      360 aacttgggtg atgctattca gccaatgtgt ccatgcttcg aggaattgct gtacgacgtt      420
ccaggttcca ctactatttt gggttcccca ttgatcctga tccaggtcac cagattgaga      480
tgcggtggtt tcatcttcgc cttgagattg aaccacacta tgtctgacgc tgccggtttg      540
attcagttct tggacactat tggtgagatg gcccaaggtt tgtctgtccc atctttgttg      600
ccaatctggc agagagagtt gctgaacgct agaaacccac aagaatcac cagaatccac      660 cacgaatacg agaaggtcac taacaccaag ggtactctga tggctatgga cgaaaactcc      720
ttggtccaca ggtcattttt cttcggtaga aagagagatca gggccctgcg taatagattg      780
ccagcttctt gggtgcttg ttccaccttc gaagttttga tggcctgtgt ttggagatgc      840
agaactatcg ctttcgctgt tgacccagac gaggttgtta gaatctcctg catcatcaac      900
atgagaggta agcacggttt cgagttgcca ccaggttact acggtaacgc ttttgttact      960
ccagcctcca tcactaaggc cggtatgttg tgtaagaacc cattggagtt cgccatcaga     1020
ctggtcaaga aagctaaggc tgaaatgtcc caagagtaca tcaagtccgt tgccgacttg     1080
atggtcatca agggtagacc tttgttcacc cagccaggta acttcactgt ttccgacgtt     1140
```

```
actagagctg gtttgggtga agttgatttc ggttggggta agccagttta cggtggtgtt    1200
gctagagctt gtccaatcat ctccttcaga atgctgttca gaaactccaa gggtgaagag    1260
ggttccgtta tcccaatttg gttgccacca ccagtcatgg aaagattcga gcaagagctg    1320
aagagaatga ccaagaaggc cgagttgttg atcacctcca tgttgtaa                 1368
```

<210> SEQ ID NO 38
<211> LENGTH: 455
<212> TYPE: PRT
<213> ORGANISM: Vitis labrusca
<220> FEATURE:
<223> OTHER INFORMATION: AMAT_AA

<400> SEQUENCE: 38

```
Met His His His His His Ala Ser Pro Ser Pro Leu Val Phe
1               5                   10                  15

Ser Val Asn Arg Cys Val Pro Gln Ile Val Arg Pro Ala Asn Pro Thr
            20                  25                  30

Pro Arg Glu Val Lys Gln Leu Ser Asp Ile Asp Asp Gln Glu Gly Arg
        35                  40                  45

Arg Phe Gln Ile Pro Val Ile Met Phe Tyr Arg Asn Asn Pro Leu Met
    50                  55                  60

Glu Gly Lys Asp Pro Val Lys Val Ile Arg Glu Ala Leu Gly Lys Ala
65                  70                  75                  80

Leu Val Tyr Tyr Tyr Pro Phe Ala Gly Arg Leu Ile Glu Gly Asp Asn
                85                  90                  95

Arg Lys Leu Met Val Asp Cys Thr Gly Glu Gly Val Leu Phe Ile Glu
            100                 105                 110

Ala Asp Ala Asp Thr Thr Leu Glu Asn Leu Gly Asp Ala Ile Gln Pro
        115                 120                 125

Met Cys Pro Cys Phe Glu Glu Leu Leu Tyr Asp Val Pro Gly Ser Thr
    130                 135                 140

Thr Ile Leu Gly Ser Pro Leu Ile Leu Ile Gln Val Thr Arg Leu Arg
145                 150                 155                 160

Cys Gly Gly Phe Ile Phe Ala Leu Arg Leu Asn His Thr Met Ser Asp
                165                 170                 175

Ala Ala Gly Leu Ile Gln Phe Leu Asp Thr Ile Gly Glu Met Ala Gln
            180                 185                 190

Gly Leu Ser Val Pro Ser Leu Leu Pro Ile Trp Gln Arg Glu Leu Leu
        195                 200                 205

Asn Ala Arg Asn Pro Pro Arg Ile Thr Arg Ile His His Glu Tyr Glu
    210                 215                 220

Lys Val Thr Asn Thr Lys Gly Thr Leu Met Ala Met Asp Glu Asn Ser
225                 230                 235                 240

Leu Val His Arg Ser Phe Phe Phe Gly Arg Glu Glu Ile Arg Ala Leu
                245                 250                 255

Arg Asn Arg Leu Pro Ala Ser Leu Gly Ala Cys Ser Thr Phe Glu Val
            260                 265                 270

Leu Met Ala Cys Val Trp Arg Cys Arg Thr Ile Ala Phe Ala Val Asp
        275                 280                 285

Pro Asp Glu Val Val Arg Ile Ser Cys Ile Ile Asn Met Arg Gly Lys
    290                 295                 300

His Gly Phe Glu Leu Pro Pro Gly Tyr Tyr Gly Asn Ala Phe Val Thr
305                 310                 315                 320
```

```
Pro Ala Ser Ile Thr Lys Ala Gly Met Leu Cys Lys Asn Pro Leu Glu
            325                 330                 335

Phe Ala Ile Arg Leu Val Lys Lys Ala Lys Ala Glu Met Ser Gln Glu
            340                 345                 350

Tyr Ile Lys Ser Val Ala Asp Leu Met Val Ile Lys Gly Arg Pro Leu
            355                 360                 365

Phe Thr Gln Pro Gly Asn Phe Thr Val Ser Asp Val Thr Arg Ala Gly
            370                 375                 380

Leu Gly Glu Val Asp Phe Gly Trp Gly Lys Pro Val Tyr Gly Gly Val
385                 390                 395                 400

Ala Arg Ala Cys Pro Ile Ile Ser Phe Arg Met Leu Phe Arg Asn Ser
            405                 410                 415

Lys Gly Glu Glu Gly Ser Val Ile Pro Ile Trp Leu Pro Pro Pro Val
            420                 425                 430

Met Glu Arg Phe Glu Gln Glu Leu Lys Arg Met Thr Lys Lys Ala Glu
            435                 440                 445

Leu Leu Ile Thr Ser Met Leu
            450                 455
```

<210> SEQ ID NO 39
<211> LENGTH: 1341
<212> TYPE: DNA
<213> ORGANISM: Capsicum annum
<220> FEATURE:
<223> OTHER INFORMATION: Pun1

<400> SEQUENCE: 39

| | | |
|---|---|---|
| atgcatcatc accaccacca cgcttttgct tgccatcttc ctttggtttc cgtctgcaac | 60 |
| aagtccttta tcaagccatc ctccttgacc ccatccacct tgagatttca caagctgtcc | 120 |
| ttcatcgacc agtccctgtc caacatgtac atcccatgtg cattcttcta ccccaaggtc | 180 |
| caacaaagat tggaggactc taagaactcc gacgagttgt ctcacattgc ccacttgttg | 240 |
| caaacttccc tgtcccagac tctggtttcc tactacccat acgctggtaa gttgaaggac | 300 |
| aacgctaccg ttgactgtaa cgacatgggt gctgagttct gtccgtcag aatcaagtgt | 360 |
| tccatgtccg agattttgga ccacccacat gcttctctgg ctgagtctat cgttttgcca | 420 |
| aaggatttgc catgggccaa caactgtgaa ggtggtaact tgttggttgt ccaggtgtcc | 480 |
| aagttcgact gtggtggtat tgctatctcc gtttgcttct cccacaagat cggtgacggt | 540 |
| tgttccttgt tgaacttctt gaacgactgg tcctccgtca ctagagatca cactactacc | 600 |
| actttggtcc catccccaag attcgttggt gactctgttt tctccaccca gaagtacggt | 660 |
| tccttgatca ctccacagat cctgtctgac ttgaaccagt gtgtccagaa gagactgatc | 720 |
| ttcccaactg acaagttgga cgctttgaga gctaaggttg ctgaagagtc cggtgttaag | 780 |
| aacccaacta gagctgaagt tgtctccgcc ttgttgttca gtgtgctac taaggcttcc | 840 |
| tcctccatgt tgccatctaa gttggtccac tttctgaaca tcaggaccat gatcaagcca | 900 |
| agattgccaa gaaacgccat cggtaacttg tcctccattt tctccattga ggccaccaac | 960 |
| atgcaggaca tggaattgcc aaccttggtc agaaacctga gaaaagaggt tgaggtcgcc | 1020 |
| tacaagaagg accaagttga gcagaacgag ctgatcttgg aagttgtcga atccatgaga | 1080 |
| gagggtaagc tgccattcga aaacatggac ggttacaaga acgtctacac ctgttccaac | 1140 |
| ctgtgcaagt accttactac caccgttgat tcggttgggg gtagaccaga gagagttttgt | 1200 |
| ttgggtaacg gtccatccaa gaacgcattc tttctgaagg actacaaggc cggtcaaggt | 1260 |

```
gttgaagcca gagttatgtt gcacaagcaa cagatgtccg agttcgagag aaacgaagag    1320
ttggtcgagt tcattgctta a                                              1341
```

<210> SEQ ID NO 40
<211> LENGTH: 446
<212> TYPE: PRT
<213> ORGANISM: Capsicum annum
<220> FEATURE:
<223> OTHER INFORMATION: Pun1_AA

<400> SEQUENCE: 40

```
Met His His His His His Ala Phe Ala Leu Pro Ser Ser Leu Val
1               5                   10                  15

Ser Val Cys Asn Lys Ser Phe Ile Lys Pro Ser Ser Leu Thr Pro Ser
                20                  25                  30

Thr Leu Arg Phe His Lys Leu Ser Phe Ile Asp Gln Ser Leu Ser Asn
            35                  40                  45

Met Tyr Ile Pro Cys Ala Phe Phe Tyr Pro Lys Val Gln Gln Arg Leu
50                  55                  60

Glu Asp Ser Lys Asn Ser Asp Glu Leu Ser His Ile Ala His Leu Leu
65                  70                  75                  80

Gln Thr Ser Leu Ser Gln Thr Leu Val Ser Tyr Tyr Pro Tyr Ala Gly
                85                  90                  95

Lys Leu Lys Asp Asn Ala Thr Val Asp Cys Asn Asp Met Gly Ala Glu
            100                 105                 110

Phe Leu Ser Val Arg Ile Lys Cys Ser Met Ser Glu Ile Leu Asp His
        115                 120                 125

Pro His Ala Ser Leu Ala Glu Ser Ile Val Leu Pro Lys Asp Leu Pro
130                 135                 140

Trp Ala Asn Asn Cys Glu Gly Gly Asn Leu Leu Val Val Gln Val Ser
145                 150                 155                 160

Lys Phe Asp Cys Gly Gly Ile Ala Ile Ser Val Cys Phe Ser His Lys
                165                 170                 175

Ile Gly Asp Gly Cys Ser Leu Leu Asn Phe Leu Asn Asp Trp Ser Ser
            180                 185                 190

Val Thr Arg Asp His Thr Thr Thr Leu Val Pro Ser Pro Arg Phe
        195                 200                 205

Val Gly Asp Ser Val Phe Ser Thr Gln Lys Tyr Gly Ser Leu Ile Thr
210                 215                 220

Pro Gln Ile Leu Ser Asp Leu Asn Gln Cys Val Gln Lys Arg Leu Ile
225                 230                 235                 240

Phe Pro Thr Asp Lys Leu Asp Ala Leu Arg Ala Lys Val Ala Glu Glu
                245                 250                 255

Ser Gly Val Lys Asn Pro Thr Arg Ala Glu Val Val Ser Ala Leu Leu
            260                 265                 270

Phe Lys Cys Ala Thr Lys Ala Ser Ser Met Leu Pro Ser Lys Leu
        275                 280                 285

Val His Phe Leu Asn Ile Arg Thr Met Ile Lys Pro Arg Leu Pro Arg
290                 295                 300

Asn Ala Ile Gly Asn Leu Ser Ser Ile Phe Ser Ile Glu Ala Thr Asn
305                 310                 315                 320

Met Gln Asp Met Glu Leu Pro Thr Leu Val Arg Asn Leu Arg Lys Glu
                325                 330                 335

Val Glu Val Ala Tyr Lys Lys Asp Gln Val Glu Gln Asn Glu Leu Ile
            340                 345                 350
```

```
Leu Glu Val Val Glu Ser Met Arg Glu Gly Lys Leu Pro Phe Glu Asn
            355                 360                 365
Met Asp Gly Tyr Lys Asn Val Tyr Thr Cys Ser Asn Leu Cys Lys Tyr
    370                 375                 380
Pro Tyr Tyr Thr Val Asp Phe Gly Trp Gly Arg Pro Glu Arg Val Cys
385                 390                 395                 400
Leu Gly Asn Gly Pro Ser Lys Asn Ala Phe Phe Leu Lys Asp Tyr Lys
            405                 410                 415
Ala Gly Gln Gly Val Glu Ala Arg Val Met Leu His Lys Gln Gln Met
            420                 425                 430
Ser Glu Phe Glu Arg Asn Glu Glu Leu Val Glu Phe Ile Ala
            435                 440                 445

<210> SEQ ID NO 41
<211> LENGTH: 1401
<212> TYPE: DNA
<213> ORGANISM: Dahlia variabilis
<220> FEATURE:
<223> OTHER INFORMATION: Dv3MaT

<400> SEQUENCE: 41
atgcatcatc accaccacca cgacaacatc ccaaacttga ctattttgga gcactccaga      60
atctccccac caccatctac tattggtcac agatccttgc ctctgacctt cttcgatatc     120
gcctggttgt tgtttccacc agtccaccac ttgtacttct accacttccc atactccaag     180
tcccacttca ccgagactgt tatccctaac ttgaagcact ccttgtccat caccttgcag     240
cactactttc cattcgtcgg taagctgatc gtctacccaa cccacacga ctctactaga      300
aagccagaga tcagacacgt tgagggtgac tctgttgctt tgactttcgc tgagactacc     360
ctggacttca cgacttgtc tgctaaccac ccaagaaagt gcgagaactt ctacccattg      420
gttccaccat gggtaacgc tgtcaaagag tccgactacg ttaccttgcc agttttctcc      480
gttcaggtca cctacttccc aaactccggt atttccatcg gtttgactaa ccaccactct     540
ttgtccgacg ctaacaccag attcggtttc ttgaaggctt gggcttccgt ttgtgaaact     600
ggtgaggatc agccattcct gaagaacggt tctccaccag ttttcgacag agttgttgtc     660
aacccacagc tgtacgagaa cagattgaac cagaccagac tgggtacttt ctaccaagct     720
ccttccttgg ttggttcctc atccgataga gttagagcca ctttcgtttt ggccagaact     780
cacatctccg gtttgaagaa gcaggtcttg actcagttgc aatgttggga gtacacctct     840
tccttcaccg ttacctgtgg ttacatctgg tcctgtatcg tcaagtcctt ggtcaacatg     900
ggtgagaaga agggtgagga cgaattggag caattcatcg tttccgttgg ttgcagatcc     960
agattggatc caccttttgcc agagaactac ttcggtaact gttccgcccc atgtatcgtc    1020
actatcaaga acggtgttct gaagggtgag aacggtttcg ttatggctgc taagttgatc    1080
ggtgagggta tctccaagat ggtcaacaag aagggtggta tcttggagta cgctgacaga    1140
tggtacgacg gtttcaagat cccagctaga aagatgggta tctccggtac tccaaagctg    1200
aacttctacg acattgactt cggttgggg aaggccatga agtacgaggt tgtttctatc    1260
gactactccg cctctgtttc cttgtccgct tgtaaagaat ccgctcagga cttcgagatc    1320
ggtgtttgtt tcccatccat gcagatggaa gccttcggta gattttcaa cgacggtttg    1380
gagtccgcta tcgcttctta a                                               1401

<210> SEQ ID NO 42
```

```
<211> LENGTH: 466
<212> TYPE: PRT
<213> ORGANISM: Dahlia variabilis
<220> FEATURE:
<223> OTHER INFORMATION: Dv3MaT_AA

<400> SEQUENCE: 42
```

Met His His His His His Asp Asn Ile Pro Asn Leu Thr Ile Leu
1               5                   10                  15

Glu His Ser Arg Ile Ser Pro Pro Ser Thr Ile Gly His Arg Ser
            20                  25                  30

Leu Pro Leu Thr Phe Phe Asp Ile Ala Trp Leu Leu Phe Pro Pro Val
            35                  40                  45

His His Leu Tyr Phe Tyr His Phe Pro Tyr Ser Lys Ser His Phe Thr
        50                  55                  60

Glu Thr Val Ile Pro Asn Leu Lys His Ser Leu Ser Ile Thr Leu Gln
65                  70                  75                  80

His Tyr Phe Pro Phe Val Gly Lys Leu Ile Val Tyr Pro Asn Pro His
                85                  90                  95

Asp Ser Thr Arg Lys Pro Glu Ile Arg His Val Glu Gly Asp Ser Val
            100                 105                 110

Ala Leu Thr Phe Ala Glu Thr Thr Leu Asp Phe Asn Asp Leu Ser Ala
        115                 120                 125

Asn His Pro Arg Lys Cys Glu Asn Phe Tyr Pro Leu Val Pro Pro Leu
130                 135                 140

Gly Asn Ala Val Lys Glu Ser Asp Tyr Val Thr Leu Pro Val Phe Ser
145                 150                 155                 160

Val Gln Val Thr Tyr Phe Pro Asn Ser Gly Ile Ser Ile Gly Leu Thr
                165                 170                 175

Asn His His Ser Leu Ser Asp Ala Asn Thr Arg Phe Gly Phe Leu Lys
            180                 185                 190

Ala Trp Ala Ser Val Cys Glu Thr Gly Glu Asp Gln Pro Phe Leu Lys
        195                 200                 205

Asn Gly Ser Pro Pro Val Phe Asp Arg Val Val Val Asn Pro Gln Leu
210                 215                 220

Tyr Glu Asn Arg Leu Asn Gln Thr Arg Leu Gly Thr Phe Tyr Gln Ala
225                 230                 235                 240

Pro Ser Leu Val Gly Ser Ser Asp Arg Val Arg Ala Thr Phe Val
                245                 250                 255

Leu Ala Arg Thr His Ile Ser Gly Leu Lys Lys Gln Val Leu Thr Gln
            260                 265                 270

Leu Pro Met Leu Glu Tyr Thr Ser Ser Phe Thr Val Thr Cys Gly Tyr
        275                 280                 285

Ile Trp Ser Cys Ile Val Lys Ser Leu Val Asn Met Gly Glu Lys Lys
290                 295                 300

Gly Glu Asp Glu Leu Glu Gln Phe Ile Val Ser Val Gly Cys Arg Ser
305                 310                 315                 320

Arg Leu Asp Pro Pro Leu Pro Glu Asn Tyr Phe Gly Asn Cys Ser Ala
                325                 330                 335

Pro Cys Ile Val Thr Ile Lys Asn Gly Val Leu Lys Gly Glu Asn Gly
            340                 345                 350

Phe Val Met Ala Ala Lys Leu Ile Gly Glu Gly Ile Ser Lys Met Val
        355                 360                 365

Asn Lys Lys Gly Gly Ile Leu Glu Tyr Ala Asp Arg Trp Tyr Asp Gly
370                 375                 380

```
Phe Lys Ile Pro Ala Arg Lys Met Gly Ile Ser Gly Thr Pro Lys Leu
385                 390                 395                 400

Asn Phe Tyr Asp Ile Asp Phe Gly Trp Gly Lys Ala Met Lys Tyr Glu
            405                 410                 415

Val Val Ser Ile Asp Tyr Ser Ala Ser Val Ser Leu Ser Ala Cys Lys
            420                 425                 430

Glu Ser Ala Gln Asp Phe Glu Ile Gly Val Cys Phe Pro Ser Met Gln
            435                 440                 445

Met Glu Ala Phe Gly Lys Ile Phe Asn Asp Gly Leu Glu Ser Ala Ile
    450                 455                 460

Ala Ser
465

<210> SEQ ID NO 43
<211> LENGTH: 1326
<212> TYPE: DNA
<213> ORGANISM: Nicotiana tababcum
<220> FEATURE:
<223> OTHER INFORMATION: NtHCT

<400> SEQUENCE: 43
atgcatcatc accaccacca caagatcgag gtcaaagaat ccaccatggt taagccagct      60
gctgagactc cacaacagag attgtggaac tccaacgttg acttggtcgt cccaaacttc     120
cacactccat ccgtctactt ctacagacca actggttccc aaacttctt cgacggtaag     180 gttttgaaag aggccttgtc caaggctctg gttccatttt atccaatggc cggtagactg     240
tgcagagatg aggatggtag aatcgagatc gactgtaagg gtcagggtgt tttgttcgtt     300
gaagctgaat ccgacggtgt tgttgatgac ttcggtgatt tcgctccaac cttggagttg     360
agacagttga ttccagctgt tgactactcc cagggtattc agtcttacgc cttgttggtc     420
ttgcagatca cccactttaa gtgtggtggt gtttccttgg gtgttggtat gcaacatcat     480
gctgctgatg gtgcttccgg tctgcacttt attaacactt ggtccgacat ggccagaggt     540
ttggacttga ctattccacc attcatcgac agaaccctgc tgagagctag agatccacca     600
caaccacaat tcccacacgt tgaataccaa ccaccaccaa ccttgaaggt tactccagag     660
aacactccaa tctccgaagc tgttccagaa acctccgttt ccatcttcaa gctgaccaga     720
gatcagatca acaccttgaa ggccaagtcc aaagaggacg taataccgt taactactcc     780 tcctacgaga tgttggctgg tcacgtttgg agatccactt gtatggctag aggattggct     840
cacgaccaag agactaagtt gtacattgct accgacggta gatccagatt gaggccatct     900
ttgccaccag gttacttcgg taacgttatc ttcactacta ccccaatcgc tgttgctggt     960
gacattcagt ctaagccaat ttggtacgct gcctccaagt gcatgatgc tttggctaga    1020 atggacaacg actacttgag atccgccttg gactacttgg aattgcagcc agatttgaag    1080
gccttggtta gaggtgctca caccttcaag tgtccaaact tgggtattac ctcctggtcc    1140
agattgccaa ttcacgatgc tgatttcggt tggggtagac caattttcat gggtccaggt    1200
ggtattgcct acgagggttt gtctttcatt ctgccatctc caactaacga cggttcccag    1260
tctgttgcta tttccttgca agctgagcac atgaagctgt cgagaagtt cctgtacgac    1320 ttctaa                                                              1326

<210> SEQ ID NO 44
<211> LENGTH: 441
<212> TYPE: PRT
```

<213> ORGANISM: Nicotiana tababcum
<220> FEATURE:
<223> OTHER INFORMATION: NtHCT_AA

<400> SEQUENCE: 44

```
Met His His His His His Lys Ile Glu Val Lys Glu Ser Thr Met
1               5                   10                  15

Val Lys Pro Ala Ala Glu Thr Pro Gln Gln Arg Leu Trp Asn Ser Asn
            20                  25                  30

Val Asp Leu Val Val Pro Asn Phe His Thr Pro Ser Val Tyr Phe Tyr
        35                  40                  45

Arg Pro Thr Gly Ser Pro Asn Phe Phe Asp Gly Lys Val Leu Lys Glu
    50                  55                  60

Ala Leu Ser Lys Ala Leu Val Pro Phe Tyr Pro Met Ala Gly Arg Leu
65                  70                  75                  80

Cys Arg Asp Glu Asp Gly Arg Ile Glu Ile Asp Cys Lys Gly Gln Gly
                85                  90                  95

Val Leu Phe Val Glu Ala Glu Ser Asp Gly Val Val Asp Asp Phe Gly
            100                 105                 110

Asp Phe Ala Pro Thr Leu Glu Leu Arg Gln Leu Ile Pro Ala Val Asp
        115                 120                 125

Tyr Ser Gln Gly Ile Gln Ser Tyr Ala Leu Leu Val Leu Gln Ile Thr
    130                 135                 140

His Phe Lys Cys Gly Gly Val Ser Leu Gly Val Gly Met Gln His His
145                 150                 155                 160

Ala Ala Asp Gly Ala Ser Gly Leu His Phe Ile Asn Thr Trp Ser Asp
                165                 170                 175

Met Ala Arg Gly Leu Asp Leu Thr Ile Pro Pro Phe Ile Asp Arg Thr
            180                 185                 190

Leu Leu Arg Ala Arg Asp Pro Pro Gln Pro Gln Phe Pro His Val Glu
        195                 200                 205

Tyr Gln Pro Pro Pro Thr Leu Lys Val Thr Pro Glu Asn Thr Pro Ile
    210                 215                 220

Ser Glu Ala Val Pro Glu Thr Ser Val Ser Ile Phe Lys Leu Thr Arg
225                 230                 235                 240

Asp Gln Ile Asn Thr Leu Lys Ala Lys Ser Lys Glu Asp Gly Asn Thr
                245                 250                 255

Val Asn Tyr Ser Ser Tyr Glu Met Leu Ala Gly His Val Trp Arg Ser
            260                 265                 270

Thr Cys Met Ala Arg Gly Leu Ala His Asp Gln Glu Thr Lys Leu Tyr
        275                 280                 285

Ile Ala Thr Asp Gly Arg Ser Arg Leu Arg Pro Ser Leu Pro Pro Gly
    290                 295                 300

Tyr Phe Gly Asn Val Ile Phe Thr Thr Thr Pro Ile Ala Val Ala Gly
305                 310                 315                 320

Asp Ile Gln Ser Lys Pro Ile Trp Tyr Ala Ser Lys Leu His Asp
                325                 330                 335

Ala Leu Ala Arg Met Asp Asn Asp Tyr Leu Arg Ser Ala Leu Asp Tyr
            340                 345                 350

Leu Glu Leu Gln Pro Asp Leu Lys Ala Leu Val Arg Gly Ala His Thr
        355                 360                 365

Phe Lys Cys Pro Asn Leu Gly Ile Thr Ser Trp Ser Arg Leu Pro Ile
    370                 375                 380

His Asp Ala Asp Phe Gly Trp Gly Arg Pro Ile Phe Met Gly Pro Gly
```

```
                385                 390                 395                 400
Gly Ile Ala Tyr Glu Gly Leu Ser Phe Ile Leu Pro Ser Pro Thr Asn
                    405                 410                 415

Asp Gly Ser Gln Ser Val Ala Ile Ser Leu Gln Ala Glu His Met Lys
                420                 425                 430

Leu Phe Glu Lys Phe Leu Tyr Asp Phe
            435                 440
```

<210> SEQ ID NO 45
<211> LENGTH: 1341
<212> TYPE: DNA
<213> ORGANISM: Aspergillus candidus
<220> FEATURE:
<223> OTHER INFORMATION: DBATAca

<400> SEQUENCE: 45

```
atgcatcatc accatcacca cgctggttct accgagttcg ttgttagatc cttggagaga      60
gttatggttg ctccatctca accatcccca aaggctttct tgcagttgtc cactttggac     120
aacttgccag gtgtcagaga gaacatcttc aacaccttgt ggtctacaa cgcctccgac      180
agagtttctg ttgatccagc caaggttatc agacaggcct gtccaaggt tctggtttac     240
tactctccat cgccggtag actgagaaag aaagaaaacg gtgacttgga ggttgagtgt      300
actggtgaag gtgctttgtt cgttgaagct atggctgaca ctgacctgtc tgttttcggt    360
gatttggacg actactcccc atctttggag cagttgttgt tctgtttgcc accagacact    420
gacatcgagg acattcaccc attggttgtt caggtcacca gattcacttg tggtggtttc    480
gttgttggtg tctccttctg tcacggtatc tgtgatggtt tgggtgctgg tcagttcttg   540
attgctgttg gtgaaatggc cagaggtgag attaagccat cttccgagcc aatctggaag   600
agagagttgt tgaagccaga ggacccactg tacagattgc agtactacca cttccagttg   660
atctgtccac catccacctt cggtaagatc gttcaaggtt ccttggttat cacctccgag   720
actatcaact gcatcaagca gtgcttgaga gaagagtcca aagagttctg ttccgccttc   780
gaagttgttt ccgctttggc ttggatcgct agaactagag ccttgcagat tccacacaac   840
gagaacgtca agctgatctt cgctatggac atgaaaagc tgttcaaccc accactgtcc   900
aagggttact acggtaactt cgttggtact gtttgcgcca tggacaacgt caaggatttg   960
ttgtctggtt ccttgctgag agtcgtcaga atcatcaaga aggccaaggt tcccctgaac  1020
gagcacttca cttccactat cgttactcca agatctggtt ccgacgagtc catcaactac  1080
gagaacatcg ttggtttcgg tgacagacgt agattgggtt tcgacgaagt tgatttcggt  1140
tggggtcacg ctgacaacgt ttctttggtt caacacggtc tgaaggacgt ttccgttgtt  1200
cagtcctacc tgctgttcat cagaccacca aagaacaacc cagacggtat caagatcctg  1260
tcctttatgc caccaccaat cgtcaagtcc ttcaagttcg agatggaaac catgaccaac  1320
aagtacgtca ccaagcctta a                                             1341
```

<210> SEQ ID NO 46
<211> LENGTH: 446
<212> TYPE: PRT
<213> ORGANISM: Aspergillus candidus
<220> FEATURE:
<223> OTHER INFORMATION: DBATAca_AA

<400> SEQUENCE: 46

```
Met His His His His His His Ala Gly Ser Thr Glu Phe Val Val Arg
1               5                   10                  15
```

-continued

Ser Leu Glu Arg Val Met Val Ala Pro Ser Gln Pro Ser Pro Lys Ala
            20                  25                  30

Phe Leu Gln Leu Ser Thr Leu Asp Asn Leu Pro Gly Val Arg Glu Asn
            35                  40                  45

Ile Phe Asn Thr Leu Leu Val Tyr Asn Ala Ser Asp Arg Val Ser Val
 50                  55                  60

Asp Pro Ala Lys Val Ile Arg Gln Ala Leu Ser Lys Val Leu Val Tyr
 65                  70                  75                  80

Tyr Ser Pro Phe Ala Gly Arg Leu Arg Lys Lys Glu Asn Gly Asp Leu
                 85                  90                  95

Glu Val Glu Cys Thr Gly Glu Gly Ala Leu Phe Val Glu Ala Met Ala
                100                 105                 110

Asp Thr Asp Leu Ser Val Phe Gly Asp Leu Asp Asp Tyr Ser Pro Ser
                115                 120                 125

Leu Glu Gln Leu Leu Phe Cys Leu Pro Pro Asp Thr Asp Ile Glu Asp
            130                 135                 140

Ile His Pro Leu Val Val Gln Val Thr Arg Phe Thr Cys Gly Gly Phe
145                 150                 155                 160

Val Val Gly Val Ser Phe Cys His Gly Ile Cys Asp Gly Leu Gly Ala
                165                 170                 175

Gly Gln Phe Leu Ile Ala Val Gly Glu Met Ala Arg Gly Glu Ile Lys
                180                 185                 190

Pro Ser Ser Glu Pro Ile Trp Lys Arg Glu Leu Leu Lys Pro Glu Asp
                195                 200                 205

Pro Leu Tyr Arg Leu Gln Tyr Tyr His Phe Gln Leu Ile Cys Pro Pro
            210                 215                 220

Ser Thr Phe Gly Lys Ile Val Gln Gly Ser Leu Val Ile Thr Ser Glu
225                 230                 235                 240

Thr Ile Asn Cys Ile Lys Gln Cys Leu Arg Glu Glu Ser Lys Glu Phe
                245                 250                 255

Cys Ser Ala Phe Glu Val Val Ser Ala Leu Ala Trp Ile Ala Arg Thr
                260                 265                 270

Arg Ala Leu Gln Ile Pro His Asn Glu Asn Val Lys Leu Ile Phe Ala
            275                 280                 285

Met Asp Met Arg Lys Leu Phe Asn Pro Pro Leu Ser Lys Gly Tyr Tyr
290                 295                 300

Gly Asn Phe Val Gly Thr Val Cys Ala Met Asp Asn Val Lys Asp Leu
305                 310                 315                 320

Leu Ser Gly Ser Leu Leu Arg Val Val Arg Ile Ile Lys Lys Ala Lys
                325                 330                 335

Val Ser Leu Asn Glu His Phe Thr Ser Thr Ile Val Thr Pro Arg Ser
            340                 345                 350

Gly Ser Asp Glu Ser Ile Asn Tyr Glu Asn Ile Val Gly Phe Gly Asp
            355                 360                 365

Arg Arg Arg Leu Gly Phe Asp Glu Val Asp Phe Gly Trp Gly His Ala
370                 375                 380

Asp Asn Val Ser Leu Val Gln His Gly Leu Lys Asp Val Ser Val Val
385                 390                 395                 400

Gln Ser Tyr Leu Leu Phe Ile Arg Pro Pro Lys Asn Asn Pro Asp Gly
                405                 410                 415

Ile Lys Ile Leu Ser Phe Met Pro Pro Ile Val Lys Ser Phe Lys
                420                 425                 430

```
Phe Glu Met Glu Thr Met Thr Asn Lys Tyr Val Thr Lys Pro
    435                 440                 445
```

<210> SEQ ID NO 47
<211> LENGTH: 1377
<212> TYPE: DNA
<213> ORGANISM: Streptomyces gancidicus
<220> FEATURE:
<223> OTHER INFORMATION: TSga

<400> SEQUENCE: 47

```
atgcatcatc accaccacca caagtctggt tctgctgctg gtgatgctgg tagaaccgtt      60
ttggttagat ctggtgaagc ttccggtgag agagttagat tgtccgttta cgacctggtc     120
aacggtactt tcggttcctc cagaaccttc tactacagac agagattgga caccgaggct     180
ttgagagagt ccttgagaag aactttggtc cactacccct tgctgaccgg tagattggtt     240
agagatgctg acagaggttt gtccgttgtt tgtgatgatg ctggtgctgt tttcgctgaa     300
actgactctg atagaccaat gccagattac ggtccagacc acagagttgg tgatgacttg     360
agaaggtaca tccacccagt taacgccttc agagttgttg gtcatgacac ccctttgttg     420
accgttaagg ttacccatat gagaggtggt ggttccgttt gggtgtttc cactaaccac      480
tctgttgttg acggttccgg ttgcttggat ttcttgttgc actggccag aacccacaga      540
ggtttggatc atagagcccc atctcacgac agagctttgt ggatggttt ggctgctggt      600
gttccaccag ctccagatga ttctcagtac gctgttatca ctggtagagc caagttcggt     660
ttcatctggc gtgttaacgc tagagccaga agagttagaa cctttaccgt cagattctcc     720
tcagccgagg ttttggcatt gagagaaact gctagagctg tggtgatca cgttagagct      780
acttccggtg atgctttgtc tgcccacatt tggagagttt tgggtgccgt tagagacaga     840
gaaccagctg ctactgaaag attgggtatc gtcgttggtt tgagaggtcc attgtctgaa     900
catctgccac atggttacgg tggtaacgct gtttccaaca tcactgctgc tttgccagct     960
agagccttga gaagaacc attggctcat actgcttccg ctgttagaga agccttggac     1020
agagttactc cagagagaat cagagaagag gctgctttct ggaggctca agaagggct     1080
ggtagagtca cagagtctt gtccagaatg gctttggact ccttcgctga cactgttcc     1140
ttgaacaacg tttccagatt gcccgtctac gctattgagt ttggtgctgg tagaccattc     1200
tggttcgaac atccagctac tccagttcca tggaccgttt tgattactcc aactccagat     1260
gacgaccact ccagagatgt tcacttgtct gttccaagag aagctgctga ggcattgaga     1320
actccagaat ggtccagaag attgcacctg agagaatctc ccccagacag atttttaa     1377
```

<210> SEQ ID NO 48
<211> LENGTH: 458
<212> TYPE: PRT
<213> ORGANISM: Streptomyces gancidicus
<220> FEATURE:
<223> OTHER INFORMATION: Tsga_AA

<400> SEQUENCE: 48

```
Met His His His His His His Lys Ser Gly Ser Ala Ala Gly Asp Ala
1               5                   10                  15

Gly Arg Thr Val Leu Val Arg Ser Gly Glu Ala Ser Gly Glu Arg Val
            20                  25                  30

Arg Leu Ser Val Tyr Asp Leu Val Asn Gly Thr Phe Gly Ser Ser Arg
        35                  40                  45

Thr Phe Tyr Tyr Arg Gln Arg Leu Asp Thr Glu Ala Leu Arg Glu Ser
```

```
            50                  55                  60
Leu Arg Arg Thr Leu Val His Tyr Pro Leu Leu Thr Gly Arg Leu Val
 65                  70                  75                  80

Arg Asp Ala Asp Arg Gly Leu Ser Val Val Cys Asp Ala Gly Ala
                 85                  90                  95

Val Phe Ala Glu Thr Asp Ser Asp Arg Pro Met Pro Asp Tyr Gly Pro
                100                 105                 110

Asp His Arg Val Gly Asp Asp Leu Arg Arg Tyr Ile His Pro Val Asn
                115                 120                 125

Ala Phe Arg Val Val Gly His Asp Thr Pro Leu Leu Thr Val Lys Val
            130                 135                 140

Thr His Met Arg Gly Gly Ser Val Leu Gly Val Ser Thr Asn His
145                 150                 155                 160

Ser Val Val Asp Gly Ser Gly Cys Leu Asp Phe Leu Leu His Trp Ser
                165                 170                 175

Arg Thr His Arg Gly Leu Asp His Arg Ala Pro Ser His Asp Arg Ala
                180                 185                 190

Leu Leu Asp Gly Leu Ala Ala Gly Val Pro Pro Ala Pro Asp Asp Ser
            195                 200                 205

Gln Tyr Ala Val Ile Thr Gly Arg Ala Lys Phe Gly Phe Ile Trp Arg
210                 215                 220

Val Asn Ala Arg Ala Arg Arg Val Arg Thr Phe Thr Val Arg Phe Ser
225                 230                 235                 240

Ser Ala Glu Val Leu Ala Leu Arg Glu Thr Ala Arg Ala Gly Gly Asp
                245                 250                 255

His Val Arg Ala Thr Ser Gly Asp Ala Leu Ser Ala His Ile Trp Arg
                260                 265                 270

Val Leu Gly Ala Val Arg Asp Arg Glu Pro Ala Ala Thr Glu Arg Leu
            275                 280                 285

Gly Ile Val Val Gly Leu Arg Gly Pro Leu Ser Glu His Leu Pro His
290                 295                 300

Gly Tyr Gly Gly Asn Ala Val Ser Asn Ile Thr Ala Ala Leu Pro Ala
305                 310                 315                 320

Arg Ala Leu Arg Glu Glu Pro Leu Ala His Thr Ala Ser Ala Val Arg
                325                 330                 335

Glu Ala Leu Asp Arg Val Thr Pro Glu Arg Ile Arg Glu Glu Ala Ala
                340                 345                 350

Phe Leu Glu Ala Gln Arg Arg Ala Gly Arg Val Asn Arg Val Leu Ser
                355                 360                 365

Arg Met Ala Leu Asp Ser Phe Ala Asp Thr Val Ser Leu Asn Asn Val
370                 375                 380

Ser Arg Leu Pro Val Tyr Ala Ile Glu Phe Gly Ala Gly Arg Pro Phe
385                 390                 395                 400

Trp Phe Glu His Pro Ala Thr Pro Val Pro Trp Thr Val Leu Ile Thr
                405                 410                 415

Pro Thr Pro Asp Asp His Ser Arg Asp Val His Leu Ser Val Pro
                420                 425                 430

Arg Glu Ala Ala Glu Ala Leu Arg Thr Pro Glu Trp Ser Arg Arg Leu
            435                 440                 445

His Leu Arg Glu Ser Ser Pro Asp Arg Phe
450                 455

<210> SEQ ID NO 49
```

<211> LENGTH: 1428
<212> TYPE: DNA
<213> ORGANISM: Streptomyces violaceusniger
<220> FEATURE:
<223> OTHER INFORMATION: TSvi

<400> SEQUENCE: 49

```
atgcatcatc accatcacca cactgcttcc gctactgaat ctggtgctaa gagaaccttc      60
actgttagag ctggtgaagc ttccggtgac agattgagat tgtccgtcta cgacatgctg     120
atcggtccaa tctacactcc aagagctttc ttctaccgtg aaaccttgga cggtgaagct     180
ttgagagctt ccttgaccag aaccctgaga aacttcccaa tcctgtccgg tagaatgaag     240
agggattctg acggtggttt gtccgttttg tgtgatgacg gtggtgttag attcgttgag     300
gcttacgctt ctgagccaat gccagattac ggtccaagac acactgctaa gaagggtttg     360
gaaagacact tgtcccacgc tatgccattc tgggttgttg atcatgacac cccactgttc     420
accgttaagt tgactcatat gaagggtggt ggttccatct tgggtttgac tatgaaccac     480
gctgttgctg acggttcttc ctacatgtct ttcttggagt cctgggtcaa cgagcataga     540
ggtttgggtt acgctaagcc atctcacgac agaggtgtta tcgatacttt gggtgctttg     600
gctactggtg acactagaac tggtggtgct cacttgactg ttactggtag aggtcaaaag     660
gctgccttca tcggtagaac tgttatgggt tccttgggta acgttactac cgtcactact     720
agattcactg ctactgagtt ggccaccatg aaggatactc tatggctga tttggccggt     780
actgaaagat gggtttccac taacgatgct ttgactgccc acttgtggaa ggttttgggt     840
gagttgagag atagaccaga cgcttccgaa gagagattgg gtttgattgc tgacttcaga     900
tcttccgctg gtgaggctgt tccagatgat tactggggta acgctgttac caacaccaga     960
ccaggtatga ctgctgctga attgagatcc agaccattgg gtgaagttgc tgctgctgtt    1020
agagcaggtc atgctatgaa caccgaagag agaatcagag aagagactgc cttcttgtgt    1080
gctgagagag atgctggtag attcaagagg gttatgacca ctatggcttt ggacgctttc    1140
gacggtacta tcgctattaa caactggtcc aagctgccct tctacagaat tgactttggt    1200
cagggtgctc cattctggta cgacttcact tctactccaa tcccatccac cgttcacatt    1260
gctccaactc cagctgatca aaacggtgcc agagatgttc atatggcctt gccaagaact    1320
caggtcagag cattgagaga accatcttgg gcttccagat tccacagata cgctgaatcc    1380
ggtgagactt tcccattgac tttcatggac tccaaggcca agagatag                 1428
```

<210> SEQ ID NO 50
<211> LENGTH: 475
<212> TYPE: PRT
<213> ORGANISM: Streptomyces violaceusniger
<220> FEATURE:
<223> OTHER INFORMATION: Tsvi_AA

<400> SEQUENCE: 50

Met His His His His His His Thr Ala Ser Ala Thr Glu Ser Gly Ala
1               5                   10                  15

Lys Arg Thr Phe Thr Val Arg Ala Gly Glu Ala Ser Gly Asp Arg Leu
            20                  25                  30

Arg Leu Ser Val Tyr Asp Met Leu Ile Gly Pro Ile Tyr Thr Pro Arg
        35                  40                  45

Ala Phe Phe Tyr Arg Glu Thr Leu Asp Gly Glu Ala Leu Arg Ala Ser
    50                  55                  60

Leu Thr Arg Thr Leu Arg Asn Phe Pro Ile Leu Ser Gly Arg Met Lys

```
            65                  70                  75                  80
Arg Asp Ser Asp Gly Gly Leu Ser Val Leu Cys Asp Gly Gly Val
                85                  90                  95

Arg Phe Val Glu Ala Tyr Ala Ser Glu Pro Met Pro Asp Tyr Gly Pro
                100                 105                 110

Arg His Thr Ala Lys Lys Gly Leu Glu Arg His Leu Ser His Ala Met
                115                 120                 125

Pro Phe Trp Val Val Asp His Asp Thr Pro Leu Phe Thr Val Lys Leu
            130                 135                 140

Thr His Met Lys Gly Gly Ser Ile Leu Gly Leu Thr Met Asn His
145                 150                 155                 160

Ala Val Ala Asp Gly Ser Ser Tyr Met Ser Phe Leu Glu Ser Trp Val
                165                 170                 175

Asn Glu His Arg Gly Leu Gly Tyr Ala Lys Pro Ser His Asp Arg Gly
                180                 185                 190

Val Ile Asp Thr Leu Gly Ala Leu Ala Thr Gly Asp Thr Arg Thr Gly
                195                 200                 205

Gly Ala His Leu Thr Val Thr Gly Arg Gly Gln Lys Ala Ala Phe Ile
            210                 215                 220

Gly Arg Thr Val Met Gly Ser Leu Gly Asn Val Thr Thr Val Thr Thr
225                 230                 235                 240

Arg Phe Thr Ala Thr Glu Leu Ala Thr Met Lys Asp Thr Ala Met Ala
                245                 250                 255

Asp Leu Ala Gly Thr Glu Arg Trp Val Ser Thr Asn Asp Ala Leu Thr
                260                 265                 270

Ala His Leu Trp Lys Val Leu Gly Glu Leu Arg Asp Arg Pro Asp Ala
            275                 280                 285

Ser Glu Glu Arg Leu Gly Leu Ile Ala Asp Phe Arg Ser Ser Ala Gly
            290                 295                 300

Glu Ala Val Pro Asp Asp Tyr Trp Gly Asn Ala Val Thr Asn Thr Arg
305                 310                 315                 320

Pro Gly Met Thr Ala Ala Glu Leu Arg Ser Arg Pro Leu Gly Glu Val
                325                 330                 335

Ala Ala Ala Val Arg Ala Gly His Ala Met Asn Thr Glu Glu Arg Ile
                340                 345                 350

Arg Glu Glu Thr Ala Phe Leu Cys Ala Glu Arg Asp Ala Gly Arg Phe
            355                 360                 365

Lys Arg Val Met Thr Thr Met Ala Leu Asp Ala Phe Asp Gly Thr Ile
            370                 375                 380

Ala Ile Asn Asn Trp Ser Lys Leu Pro Phe Tyr Arg Ile Asp Phe Gly
385                 390                 395                 400

Gln Gly Ala Pro Phe Trp Tyr Asp Phe Thr Ser Thr Pro Ile Pro Ser
                405                 410                 415

Thr Val His Ile Ala Pro Thr Pro Ala Asp Gln Asn Gly Ala Arg Asp
                420                 425                 430

Val His Met Ala Leu Pro Arg Thr Gln Val Arg Ala Leu Arg Glu Pro
            435                 440                 445

Ser Trp Ala Ser Arg Phe His Arg Tyr Ala Glu Ser Gly Glu Thr Phe
            450                 455                 460

Pro Leu Thr Phe Met Asp Ser Lys Ala Lys Arg
465                 470                 475
```

<210> SEQ ID NO 51

```
<211> LENGTH: 672
<212> TYPE: DNA
<213> ORGANISM: Shigella sonnei
<220> FEATURE:
<223> OTHER INFORMATION: CAT

<400> SEQUENCE: 51
atgcatcatc accatcacca cgagaaaaaa atcactggat ataccaccgt tgatatatcc      60
caatggcatc gtaaagaaca ttttgaggca tttcagtcag ttgctcaatg tacctataac    120
cagaccgttc agctggatat tacggccttt ttaaagaccg taaagaaaaa taagcacaag    180
ttttatccgg cctttattca cattcttgcc cgcctgatga atgctcatcc ggaattacgt    240
atggcaatga agacggtga gctggtgata tgggatagtg ttcacccttg ttacaccgtt    300
ttccatgagc aaactgaaac gttttcatcg ctctggagtg aataccacga cgatttccgg    360
cagtttctac acatatattc gcaagatgtg gcgtgttacg gtgaaaacct ggcctatttc    420
cctaaagggt ttattgagaa tatgttttc gtctcagcca atccctgggt gagtttcacc    480
agttttgatt taaacgtggc caatatggac aacttcttcg cccccgtttt caccatgggc    540
aaatattata cgcaaggcga caaggtgctg atgccgctgg cgattcaggt tcatcatgcc    600
gtttgtgatg gcttccatgt cggcagaatg cttaatgaat acaacagta ctgcgatgaa    660
ggggcggcct ga                                                       672

<210> SEQ ID NO 52
<211> LENGTH: 223
<212> TYPE: PRT
<213> ORGANISM: Shigella sonnei
<220> FEATURE:
<223> OTHER INFORMATION: CAT_AA

<400> SEQUENCE: 52
```

Met His His His His His His Glu Lys Lys Ile Thr Gly Tyr Thr Thr
1               5                   10                  15

Val Asp Ile Ser Gln Trp His Arg Lys Glu His Phe Glu Ala Phe Gln
            20                  25                  30

Ser Val Ala Gln Cys Thr Tyr Asn Gln Thr Val Gln Leu Asp Ile Thr
        35                  40                  45

Ala Phe Leu Lys Thr Val Lys Lys Asn Lys His Lys Phe Tyr Pro Ala
    50                  55                  60

Phe Ile His Ile Leu Ala Arg Leu Met Asn Ala His Pro Glu Leu Arg
65                  70                  75                  80

Met Ala Met Lys Asp Gly Glu Leu Val Ile Trp Asp Ser Val His Pro
                85                  90                  95

Cys Tyr Thr Val Phe His Glu Gln Thr Glu Thr Phe Ser Ser Leu Trp
            100                 105                 110

Ser Glu Tyr His Asp Asp Phe Arg Gln Phe Leu His Ile Tyr Ser Gln
        115                 120                 125

Asp Val Ala Cys Tyr Gly Glu Asn Leu Ala Tyr Phe Pro Lys Gly Phe
    130                 135                 140

Ile Glu Asn Met Phe Phe Val Ser Ala Asn Pro Trp Val Ser Phe Thr
145                 150                 155                 160

Ser Phe Asp Leu Asn Val Ala Asn Met Asp Asn Phe Phe Ala Pro Val
                165                 170                 175

Phe Thr Met Gly Lys Tyr Tyr Thr Gln Gly Asp Lys Val Leu Met Pro
            180                 185                 190

Leu Ala Ile Gln Val His His Ala Val Cys Asp Gly Phe His Val Gly

```
                   195                 200                 205
Arg Met Leu Asn Glu Leu Gln Gln Tyr Cys Asp Glu Gly Ala Ala
    210                 215                 220
```

<210> SEQ ID NO 53
<211> LENGTH: 1374
<212> TYPE: DNA
<213> ORGANISM: Saccharomyces cerevisiae
<220> FEATURE:
<223> OTHER INFORMATION: EHT

<400> SEQUENCE: 53

```
atgcatcatc accatcacca ctcagaagtt tccaaatggc cagcaatcaa cccattccat      60
tggggataca atggtacagt ttcgcatatt gtcggtgaaa atggttccat aaactccat     120
ttaaaagaca acaaggagca agttgatttt gacgagttcg ctaacaaata tgtcccaacg    180
ttgaagaatg gtgcccaatt caaattgagt ccttacttgt tcacaggtat tttgcaaact    240
ttgtacttag gtgctgctga tttctctaag aaatttcctg tattctacgg cagggaaatt    300
gtcaaattct cggatggtgg agtttgcacc gctgactggc tcatagattc atggaaaaag    360
gattatgagt tcgatcaaag tactacgagc tttgataaaa aaaatttga taaagacgag    420
aaggcgacac atccagaagg atggcctcgt ttacaaccac gtacaaggta cctgaaagat    480
aatgagttgg aagaactacg ggaggttgat ctacccctag tagttattct acatggtctt    540
gctggtggta gtcatgagcc gattataaga tctcttgctg aaaacctgtc tcgcagtggg    600
agatttcaag tggtcgtcct aaataccaga ggttgtgcac gttccaaaat taccaccaga    660
aatttattta cagcttatca cacaatggat attcgcgagt ttttgcaaag agaaaagcaa    720
agacatccag atagaaaact atacgctgtg ggatgctctt tggtgctac gatgctggca    780
aactatctgg gagaagaggg cgataaatca cctttatccg cagctgctac tttgtgcaat    840
ccttgggatc ttctccttc agcaattagg atgagccagg attggtggtc aagaacttta    900
ttttccaaaa atattgcgca attcttaaca agaaccgttc aggttaatat gggtgaatta    960
ggagttccaa atggctctct ccccgatcat cctcccacag tcaagaatcc atctttctat   1020
atgttcacgc ctgaaaatct aataaaggca aagagcttta atcgacccg ggaatttgat    1080
gaagtgtaca ctgcgcctgc tttaggcttc ccaaatgcta tggagtatta taagcggcc    1140
agctcaataa acagagttga tacaattcgg gttcctaccc ttgttatcaa ttccagggat   1200
gatcctgttg tcggcccaga tcaaccatac tcaatcgtgg aaaagaatcc tcgtattttg   1260
tattgtagaa ccgatttagg tggtcattta gcttacctag ataaagacaa caactcgtgg   1320
gctaccaagg caattgcaga atttttcact aagtttgatg aattagtcgt atga         1374
```

<210> SEQ ID NO 54
<211> LENGTH: 457
<212> TYPE: PRT
<213> ORGANISM: Saccharomyces cerevisiae
<220> FEATURE:
<223> OTHER INFORMATION: EHT_AA

<400> SEQUENCE: 54

```
Met His His His His His His Ser Glu Val Ser Lys Trp Pro Ala Ile
1               5                   10                  15

Asn Pro Phe His Trp Gly Tyr Asn Gly Thr Val Ser His Ile Val Gly
            20                  25                  30

Glu Asn Gly Ser Ile Lys Leu His Leu Lys Asp Asn Lys Glu Gln Val
        35                  40                  45
```

-continued

Asp Phe Asp Glu Phe Ala Asn Lys Tyr Val Pro Thr Leu Lys Asn Gly
    50                  55                  60

Ala Gln Phe Lys Leu Ser Pro Tyr Leu Phe Thr Gly Ile Leu Gln Thr
65                  70                  75                  80

Leu Tyr Leu Gly Ala Ala Asp Phe Ser Lys Lys Phe Pro Val Phe Tyr
                85                  90                  95

Gly Arg Glu Ile Val Lys Phe Ser Asp Gly Val Cys Thr Ala Asp
                100                 105                 110

Trp Leu Ile Asp Ser Trp Lys Lys Asp Tyr Glu Phe Asp Gln Ser Thr
            115                 120                 125

Thr Ser Phe Asp Lys Lys Lys Phe Asp Lys Asp Glu Lys Ala Thr His
    130                 135                 140

Pro Glu Gly Trp Pro Arg Leu Gln Pro Arg Thr Arg Tyr Leu Lys Asp
145                 150                 155                 160

Asn Glu Leu Glu Glu Leu Arg Glu Val Asp Leu Pro Leu Val Val Ile
                165                 170                 175

Leu His Gly Leu Ala Gly Gly Ser His Glu Pro Ile Ile Arg Ser Leu
                180                 185                 190

Ala Glu Asn Leu Ser Arg Ser Gly Arg Phe Gln Val Val Val Leu Asn
            195                 200                 205

Thr Arg Gly Cys Ala Arg Ser Lys Ile Thr Thr Arg Asn Leu Phe Thr
    210                 215                 220

Ala Tyr His Thr Met Asp Ile Arg Glu Phe Leu Gln Arg Glu Lys Gln
225                 230                 235                 240

Arg His Pro Asp Arg Lys Leu Tyr Ala Val Gly Cys Ser Phe Gly Ala
                245                 250                 255

Thr Met Leu Ala Asn Tyr Leu Gly Glu Glu Gly Asp Lys Ser Pro Leu
            260                 265                 270

Ser Ala Ala Ala Thr Leu Cys Asn Pro Trp Asp Leu Leu Ser Ala
        275                 280                 285

Ile Arg Met Ser Gln Asp Trp Trp Ser Arg Thr Leu Phe Ser Lys Asn
    290                 295                 300

Ile Ala Gln Phe Leu Thr Arg Thr Val Gln Val Asn Met Gly Glu Leu
305                 310                 315                 320

Gly Val Pro Asn Gly Ser Leu Pro Asp His Pro Pro Thr Val Lys Asn
                325                 330                 335

Pro Ser Phe Tyr Met Phe Thr Pro Glu Asn Leu Ile Lys Ala Lys Ser
                340                 345                 350

Phe Lys Ser Thr Arg Glu Phe Asp Glu Val Tyr Thr Ala Pro Ala Leu
        355                 360                 365

Gly Phe Pro Asn Ala Met Glu Tyr Tyr Lys Ala Ala Ser Ser Ile Asn
    370                 375                 380

Arg Val Asp Thr Ile Arg Val Pro Thr Leu Val Ile Asn Ser Arg Asp
385                 390                 395                 400

Asp Pro Val Val Gly Pro Asp Gln Pro Tyr Ser Ile Val Glu Lys Asn
                405                 410                 415

Pro Arg Ile Leu Tyr Cys Arg Thr Asp Leu Gly Gly His Leu Ala Tyr
                420                 425                 430

Leu Asp Lys Asp Asn Asn Ser Trp Ala Thr Lys Ala Ile Ala Glu Phe
        435                 440                 445

Phe Thr Lys Phe Asp Glu Leu Val Val
    450                 455

<210> SEQ ID NO 55
<211> LENGTH: 1596
<212> TYPE: DNA
<213> ORGANISM: Saccharomyces cerevisiae
<220> FEATURE:
<223> OTHER INFORMATION: ATF

<400> SEQUENCE: 55

| | |
|---|---|
| atgcatcatc accatcacca caatgaaatc gatgagaaaa atcaggcccc cgtgcaacaa | 60 |
| gaatgcctga aagagatgat tcagaatggg catgctcggc gtatgggatc tgttgaagat | 120 |
| ctgtatgttg ctctcaacag acaaaactta tatcgaaact tctgcacgta tggagaattg | 180 |
| agtgattact gtactaggga tcagctcaca ttagctttga gggaaatctg cctgaaaaat | 240 |
| ccaactcttt tacatattgt tctaccaaca agatggccaa atcatgaaaa ttattatcgc | 300 |
| agttccgaat actattcacg ccacatcca gtgcatgatt atatttcagt attacaagaa | 360 |
| ttgaaactga gtggtgtggt tctcaatgaa caacctgagt acagtgcagt aatgaagcaa | 420 |
| atattagaag agttcaaaaa tagtaagggt tcctatactg caaaaatttt taaacttact | 480 |
| accactttga ctattcctta ctttggacca acaggaccga gttggcggct aatttgtctt | 540 |
| ccagaagagc acacagaaaa gtggaaaaaa tttatctttg tatctaatca ttgcatgtct | 600 |
| gatggtcggt cttcgatcca cttttttcat gatttaagag acgaattaaa taatattaaa | 660 |
| actccaccaa aaaattaga ttacattttc aagtacgagg aggattacca attattgagg | 720 |
| aaacttccag aaccgatcga aaaggtgata gactttagac caccgtactt gtttattccg | 780 |
| aagtcacttc tttcgggttt catctacaat catttgagat tttcttcaaa aggtgtctgt | 840 |
| atgagaatgg atgatgtgga aaaaaccgat gatgttgtca ccgagatcat caatatttca | 900 |
| ccaacagaat tcaagcgat taaagcaaat attaaatcaa atatccaagg taagtgtact | 960 |
| atcactccgt ttttacatgt ttgttggttt gtatctcttc ataaatgggg taaatttttc | 1020 |
| aaaccattga acttcgaatg gcttacggat atttttatcc ccgcagattg ccgctcacaa | 1080 |
| ctaccagatg atgatgaaat gagacagat tacagatatg gcgctaacgt tggatttatt | 1140 |
| gacttcaccc cctggataag cgaatttgac atgaatgata caaagaaaa ttttttggcca | 1200 |
| cttattgagc actaccatga agtaatttcg gaagctttaa gaaataaaaa gcatctccat | 1260 |
| ggcttagggt tcaatataca aggcttcgtt caaaaatatg tgaacattga caaggtaatg | 1320 |
| tgcgatcgtg ccatcgggaa aagacgcgga ggtacattgt taagcaatgt aggtctgttt | 1380 |
| aatcagttag aggagcccga tgccaaatat tctatatgcg attggcatt tggccaattt | 1440 |
| caaggatcct ggcaccaagc attttccttg ggtgtttgtt cgactaatgt aaaggggatg | 1500 |
| aatattgttg ttgcttcaac aaagaatgtt gttggtagtc aagaatctct cgaagagctt | 1560 |
| tgctccattt acaaagctct cctttttaggc ccttag | 1596 |

<210> SEQ ID NO 56
<211> LENGTH: 531
<212> TYPE: PRT
<213> ORGANISM: Saccharomyces cerevisiae
<220> FEATURE:
<223> OTHER INFORMATION: ATF_AA

<400> SEQUENCE: 56

Met His His His His His His Asn Glu Ile Asp Glu Lys Asn Gln Ala
1               5                   10                  15

Pro Val Gln Gln Glu Cys Leu Lys Glu Met Ile Gln Asn Gly His Ala
            20                  25                  30

-continued

Arg Arg Met Gly Ser Val Glu Asp Leu Tyr Val Ala Leu Asn Arg Gln
         35                  40                  45

Asn Leu Tyr Arg Asn Phe Cys Thr Tyr Gly Glu Leu Ser Asp Tyr Cys
 50                  55                  60

Thr Arg Asp Gln Leu Thr Leu Ala Leu Arg Glu Ile Cys Leu Lys Asn
65                  70                  75                  80

Pro Thr Leu Leu His Ile Val Leu Pro Thr Arg Trp Pro Asn His Glu
                 85                  90                  95

Asn Tyr Tyr Arg Ser Ser Glu Tyr Tyr Ser Arg Pro His Pro Val His
                100                 105                 110

Asp Tyr Ile Ser Val Leu Gln Glu Leu Lys Leu Ser Gly Val Val Leu
                115                 120                 125

Asn Glu Gln Pro Glu Tyr Ser Ala Val Met Lys Gln Ile Leu Glu Glu
130                 135                 140

Phe Lys Asn Ser Lys Gly Ser Tyr Thr Ala Lys Ile Phe Lys Leu Thr
145                 150                 155                 160

Thr Thr Leu Thr Ile Pro Tyr Phe Gly Pro Thr Gly Pro Ser Trp Arg
                 165                 170                 175

Leu Ile Cys Leu Pro Glu Glu His Thr Glu Lys Trp Lys Lys Phe Ile
                180                 185                 190

Phe Val Ser Asn His Cys Met Ser Asp Gly Arg Ser Ser Ile His Phe
                195                 200                 205

Phe His Asp Leu Arg Asp Glu Leu Asn Asn Ile Lys Thr Pro Pro Lys
                210                 215                 220

Lys Leu Asp Tyr Ile Phe Lys Tyr Glu Glu Asp Tyr Gln Leu Leu Arg
225                 230                 235                 240

Lys Leu Pro Glu Pro Ile Glu Lys Val Ile Asp Phe Arg Pro Pro Tyr
                245                 250                 255

Leu Phe Ile Pro Lys Ser Leu Leu Ser Gly Phe Ile Tyr Asn His Leu
                260                 265                 270

Arg Phe Ser Ser Lys Gly Val Cys Met Arg Met Asp Asp Val Glu Lys
                275                 280                 285

Thr Asp Asp Val Val Thr Glu Ile Ile Asn Ile Ser Pro Thr Glu Phe
                290                 295                 300

Gln Ala Ile Lys Ala Asn Ile Lys Ser Asn Ile Gln Gly Lys Cys Thr
305                 310                 315                 320

Ile Thr Pro Phe Leu His Val Cys Trp Phe Val Ser Leu His Lys Trp
                325                 330                 335

Gly Lys Phe Phe Lys Pro Leu Asn Phe Glu Trp Leu Thr Asp Ile Phe
                340                 345                 350

Ile Pro Ala Asp Cys Arg Ser Gln Leu Pro Asp Asp Asp Glu Met Arg
                355                 360                 365

Gln Met Tyr Arg Tyr Gly Ala Asn Val Gly Phe Ile Asp Phe Thr Pro
370                 375                 380

Trp Ile Ser Glu Phe Asp Met Asn Asp Asn Lys Glu Asn Phe Trp Pro
385                 390                 395                 400

Leu Ile Glu His Tyr His Glu Val Ile Ser Glu Ala Leu Arg Asn Lys
                405                 410                 415

Lys His Leu His Gly Leu Gly Phe Asn Ile Gln Gly Phe Val Gln Lys
                420                 425                 430

Tyr Val Asn Ile Asp Lys Val Met Cys Asp Arg Ala Ile Gly Lys Arg
                435                 440                 445

Arg Gly Gly Thr Leu Leu Ser Asn Val Gly Leu Phe Asn Gln Leu Glu
    450                 455                 460

Glu Pro Asp Ala Lys Tyr Ser Ile Cys Asp Leu Ala Phe Gly Gln Phe
465                 470                 475                 480

Gln Gly Ser Trp His Gln Ala Phe Ser Leu Gly Val Cys Ser Thr Asn
                485                 490                 495

Val Lys Gly Met Asn Ile Val Val Ala Ser Thr Lys Asn Val Val Gly
            500                 505                 510

Ser Gln Glu Ser Leu Glu Glu Leu Cys Ser Ile Tyr Lys Ala Leu Leu
        515                 520                 525

Leu Gly Pro
    530

<210> SEQ ID NO 57
<211> LENGTH: 1344
<212> TYPE: DNA
<213> ORGANISM: Arabidopsis thaliana
<220> FEATURE:
<223> OTHER INFORMATION: Aco_op

<400> SEQUENCE: 57

```
atgcatcacc atcaccatca cactagtgga tccatggcag tcctatcctc agctgatagg      60
gctagtaacg aaaagaaggt aaagtcatct tacttcgact tgcctccaat ggaaatgtca     120
gttgcattcc acaagccac accagcttct acgtttcccc cgtgcacttc tgattactat     180
cactttaatg acttgttgac accagaagag caggcaatta gaaagaaggt aagagagtgt     240
atggaaaaag aagttgctcc gattatgact gaatactggg agaaggcaga gtttccattt     300
catataacac ctaagctagg ggctatggga gttgcaggcg atctatcaa aggttacggt     360 tgtccaggcc taagcatcac agccaatgct atcgcaacag ccgaaattgc aagggttgat     420
gccagttgtt ctacgttcat tttagtccat agttctttag gaatgctgac aattgcttta     480
tgcggtagtg aagcacaaaa agagaaatac cttccatcct ggcacaaact taatacagtg     540
gcctgctggg cgcttactga ccagataat ggttctgatg cttcaggatt gggaaccaca     600
gcgactaagg tggaaggcgg ttggaagatt aacggtcaaa aaggtggat aggaaactca     660 acattcgcgg atttattgat tatctttgct agaaacacga ctaccaacca aatcaacggc     720
ttcattgtaa agaaagatgc tcctggctta aaagcaacca aaatccctaa taaaattggt     780
ttgaggatgg tacaaaacgg ggatatcttg ttacagaacg tgtttgtgcc cgacgaagat     840
cgtctacccg tgttaattc tttccaagac acttccaagg tattagcagt ctcacgtgtt     900
atggtagctt ggcagcctat tggtatctct atgggtatct acgatatgtg tcatagatac     960
ctgaaagaaa ggaagcagtt tggagctcct ttagctgctt tcaacttaa ccagcaaaaa    1020 ttggtacaaa tgttaggaaa tgttcaagcg atgttcctta tgggctggag attgtgtaag    1080
ttatacgaaa ctggtcaaat gacacctggt caggcgtcat taggtaaggc ttggatatcc    1140
tctaaggcaa gagaaacagc aagtttgggc agagaacttt taggtggaaa cggtatttta    1200
gccgatttcc tagttgcgaa agcattctgt gacttggagc ctatatacac atacgaaggg    1260
acttacgata ttaatacatt agtgacgggg agagaagtta caggcattgc tagtttcaaa    1320
ccagctacaa ggtctagatt ataa                                           1344
```

<210> SEQ ID NO 58
<211> LENGTH: 447
<212> TYPE: PRT
<213> ORGANISM: Arabidopsis thaliana
<220> FEATURE:
<223> OTHER INFORMATION: Aco_AA

<400> SEQUENCE: 58

```
Met His His His His His Thr Ser Gly Ser Met Ala Val Leu Ser
1               5                   10                  15

Ser Ala Asp Arg Ala Ser Asn Glu Lys Val Lys Ser Ser Tyr Phe
                20                  25                  30

Asp Leu Pro Pro Met Glu Met Ser Val Ala Phe Pro Gln Ala Thr Pro
                35                  40                  45

Ala Ser Thr Phe Pro Pro Cys Thr Ser Asp Tyr Tyr His Phe Asn Asp
        50                  55                  60

Leu Leu Thr Pro Glu Glu Gln Ala Ile Arg Lys Lys Val Arg Glu Cys
65                  70                  75                  80

Met Glu Lys Glu Val Ala Pro Ile Met Thr Glu Tyr Trp Glu Lys Ala
                85                  90                  95

Glu Phe Pro Phe His Ile Thr Pro Lys Leu Gly Ala Met Gly Val Ala
                100                 105                 110

Gly Gly Ser Ile Lys Gly Tyr Gly Cys Pro Gly Leu Ser Ile Thr Ala
            115                 120                 125

Asn Ala Ile Ala Thr Ala Glu Ile Ala Arg Val Asp Ala Ser Cys Ser
    130                 135                 140

Thr Phe Ile Leu Val His Ser Ser Leu Gly Met Leu Thr Ile Ala Leu
145                 150                 155                 160

Cys Gly Ser Glu Ala Gln Lys Glu Lys Tyr Leu Pro Ser Leu Ala Gln
                165                 170                 175

Leu Asn Thr Val Ala Cys Trp Ala Leu Thr Glu Pro Asp Asn Gly Ser
            180                 185                 190

Asp Ala Ser Gly Leu Gly Thr Thr Ala Thr Lys Val Glu Gly Gly Trp
        195                 200                 205

Lys Ile Asn Gly Gln Lys Arg Trp Ile Gly Asn Ser Thr Phe Ala Asp
    210                 215                 220

Leu Leu Ile Ile Phe Ala Arg Asn Thr Thr Thr Asn Gln Ile Asn Gly
225                 230                 235                 240

Phe Ile Val Lys Lys Asp Ala Pro Gly Leu Lys Ala Thr Lys Ile Pro
                245                 250                 255

Asn Lys Ile Gly Leu Arg Met Val Gln Asn Gly Asp Ile Leu Leu Gln
            260                 265                 270

Asn Val Phe Val Pro Asp Glu Asp Arg Leu Pro Gly Val Asn Ser Phe
        275                 280                 285

Gln Asp Thr Ser Lys Val Leu Ala Val Ser Arg Val Met Val Ala Trp
    290                 295                 300

Gln Pro Ile Gly Ile Ser Met Gly Ile Tyr Asp Met Cys His Arg Tyr
305                 310                 315                 320

Leu Lys Glu Arg Lys Gln Phe Gly Ala Pro Leu Ala Ala Phe Gln Leu
                325                 330                 335

Asn Gln Gln Lys Leu Val Gln Met Leu Gly Asn Val Gln Ala Met Phe
            340                 345                 350

Leu Met Gly Trp Arg Leu Cys Lys Leu Tyr Glu Thr Gly Gln Met Thr
        355                 360                 365

Pro Gly Gln Ala Ser Leu Gly Lys Ala Trp Ile Ser Ser Lys Ala Arg
    370                 375                 380

Glu Thr Ala Ser Leu Gly Arg Glu Leu Leu Gly Gly Asn Gly Ile Leu
385                 390                 395                 400
```

Ala Asp Phe Leu Val Ala Lys Ala Phe Cys Asp Leu Glu Pro Ile Tyr
            405                 410                 415

Thr Tyr Glu Gly Thr Tyr Asp Ile Asn Thr Leu Val Thr Gly Arg Glu
            420                 425                 430

Val Thr Gly Ile Ala Ser Phe Lys Pro Ala Thr Arg Ser Arg Leu
            435                 440                 445

<210> SEQ ID NO 59
<211> LENGTH: 1554
<212> TYPE: DNA
<213> ORGANISM: Megasphaera elsedenii
<220> FEATURE:
<223> OTHER INFORMATION: Pct_Me

<400> SEQUENCE: 59

| | | | | | |
|---|---|---|---|---|---|
| atgagaaagg | ttgaaattat | taccgctgaa | caagctgctc | aattggttaa | ggacaacgac | 60 |
| accattacct | ctattggttt | cgtttcttct | gctcacccag | aagctttgac | caaggctttg | 120 |
| gaaagagat | tcttggacac | caacaccca | caaaacttga | cctacattta | cgctggttct | 180 |
| caaggtaaga | gagacggtag | agctgctgaa | cacttggctc | acaccggttt | gttgaagaga | 240 |
| gctattattg | tcactggca | aaccgttcca | gctattggta | agtggctgt | gaaaacaag | 300 |
| attgaagctt | acaacttctc | tcaaggtacc | ttggttcact | ggttcagagc | tttggctggt | 360 |
| cacaagttgg | gtgttttcac | cgacattggt | ttggaaacct | tcttggaccc | aagacaattg | 420 |
| ggtggtaagt | tgaacgacgt | taccaaggaa | gacttggtta | agttgattga | agttgacggt | 480 |
| cacgaacaat | tgttctaccc | aaccttccca | gttaacgttg | ctttcttgag | aggtacctac | 540 |
| gctgacgaat | ctggtaacat | tactatggac | gaagaaattg | gtccattcga | atctacctct | 600 |
| gttgctcaag | ctgttcacaa | ctgtggtggt | aaggttgttg | ttcaagttaa | ggacgttgtt | 660 |
| gctcacggtt | cttggaccc | aagaatggtt | aagattccag | gtatttacgt | tgactacgtt | 720 |
| gttgttgctg | ctccagaaga | ccaccaacaa | acctacgact | gtgaatacga | cccatctttg | 780 |
| tctggtgaac | acagagctcc | agaaggtgct | accgacgctg | ctttgccaat | gtctgctaag | 840 |
| aagattattg | gtagaagagg | tgcttttgaa | ttgaccgaaa | acgctgttgt | taacttgggt | 900 |
| gttggtgctc | cagaatacgt | tgcttctgtt | gctggtgaag | aaggtattgc | tgacaccatt | 960 |
| accttgaccg | ttgaaggtgg | tgctattggt | ggtgttccac | aaggtggtgc | tagattcggt | 1020 |
| tcttcaagaa | cgctgacgc | tattattgac | cacacctacc | aattcgactt | ctacgacggt | 1080 |
| ggtggtttgg | acattgctta | cttgggtttg | gctcaatgtg | acggttctgg | taacattaac | 1140 |
| gtttctaagt | tcggtaccaa | cgttgctggt | tgtggtggtt | cccaaacat | ttctcaacaa | 1200 |
| accccaaacg | tttacttctg | tggtaccttc | accgctggtg | gtttgaagat | tgctgttgaa | 1260 |
| gacggtaagg | ttaagatttt | gcaagaaggt | aaggctaaga | agttcattaa | ggctgttgac | 1320 |
| caaattacct | tcaacggttc | ttacgctgct | agaaacggta | agcacgtttt | gtacattacc | 1380 |
| gaaagatgtg | ttttcgaatt | gaccaaggaa | ggtttgaagt | tgattgaagt | tgctccaggt | 1440 |
| attgacattg | aaaaggacat | tttggctcac | atggacttca | agccaattat | tgacaaccca | 1500 |
| aagttgatgg | acgctagatt | gttccaagac | ggtccaatgg | gtttgaagaa | gtaa | 1554 |

<210> SEQ ID NO 60
<211> LENGTH: 517
<212> TYPE: PRT
<213> ORGANISM: Megasphaera elsedenii
<220> FEATURE:
<223> OTHER INFORMATION: Pct_Me_AA

<400> SEQUENCE: 60

Met Arg Lys Val Glu Ile Ile Thr Ala Glu Gln Ala Gln Leu Val
1               5                   10                  15

Lys Asp Asn Asp Thr Ile Thr Ser Ile Gly Phe Val Ser Ser Ala His
            20                  25                  30

Pro Glu Ala Leu Thr Lys Ala Leu Glu Lys Arg Phe Leu Asp Thr Asn
        35                  40                  45

Thr Pro Gln Asn Leu Thr Tyr Ile Tyr Ala Gly Ser Gln Gly Lys Arg
    50                  55                  60

Asp Gly Arg Ala Ala Glu His Leu Ala His Thr Gly Leu Leu Lys Arg
65                  70                  75                  80

Ala Ile Ile Gly His Trp Gln Thr Val Pro Ala Ile Gly Lys Leu Ala
                85                  90                  95

Val Glu Asn Lys Ile Glu Ala Tyr Asn Phe Ser Gln Gly Thr Leu Val
            100                 105                 110

His Trp Phe Arg Ala Leu Ala Gly His Lys Leu Gly Val Phe Thr Asp
        115                 120                 125

Ile Gly Leu Glu Thr Phe Leu Asp Pro Arg Gln Leu Gly Gly Lys Leu
    130                 135                 140

Asn Asp Val Thr Lys Glu Asp Leu Val Lys Leu Ile Glu Val Asp Gly
145                 150                 155                 160

His Glu Gln Leu Phe Tyr Pro Thr Phe Pro Val Asn Val Ala Phe Leu
                165                 170                 175

Arg Gly Thr Tyr Ala Asp Glu Ser Gly Asn Ile Thr Met Asp Glu Glu
            180                 185                 190

Ile Gly Pro Phe Glu Ser Thr Ser Val Ala Gln Ala Val His Asn Cys
        195                 200                 205

Gly Gly Lys Val Val Gln Val Lys Asp Val Val Ala His Gly Ser
    210                 215                 220

Leu Asp Pro Arg Met Val Lys Ile Pro Gly Ile Tyr Val Asp Tyr Val
225                 230                 235                 240

Val Val Ala Ala Pro Glu Asp His Gln Gln Thr Tyr Asp Cys Glu Tyr
                245                 250                 255

Asp Pro Ser Leu Ser Gly Glu His Arg Ala Pro Glu Gly Ala Thr Asp
            260                 265                 270

Ala Ala Leu Pro Met Ser Ala Lys Lys Ile Ile Gly Arg Arg Gly Ala
        275                 280                 285

Leu Glu Leu Thr Glu Asn Ala Val Val Asn Leu Gly Val Gly Ala Pro
    290                 295                 300

Glu Tyr Val Ala Ser Val Ala Gly Glu Glu Ile Ala Asp Thr Ile
305                 310                 315                 320

Thr Leu Thr Val Glu Gly Gly Ala Ile Gly Gly Val Pro Gln Gly Gly
                325                 330                 335

Ala Arg Phe Gly Ser Ser Arg Asn Ala Asp Ala Ile Ile Asp His Thr
            340                 345                 350

Tyr Gln Phe Asp Phe Tyr Asp Gly Gly Leu Asp Ile Ala Tyr Leu
        355                 360                 365

Gly Leu Ala Gln Cys Asp Gly Ser Gly Asn Ile Asn Val Ser Lys Phe
    370                 375                 380

Gly Thr Asn Val Ala Gly Cys Gly Gly Phe Pro Asn Ile Ser Gln Gln
385                 390                 395                 400

Thr Pro Asn Val Tyr Phe Cys Gly Thr Phe Thr Ala Gly Gly Leu Lys

```
                    405                 410                 415
Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
    450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515

<210> SEQ ID NO 61
<211> LENGTH: 1629
<212> TYPE: DNA
<213> ORGANISM: Cupriavidus necator
<220> FEATURE:
<223> OTHER INFORMATION: Pct_Cn

<400> SEQUENCE: 61
atgaaggtta ttaccgcaag agaagctgct gcattggttc aagacggttg gaccgttgct      60
tctgctggtt tcgttggtgc tggtcacgct gaagctgtta ccgaagcatt ggaacaaaga     120
ttcttgcaat ctggattgcc aagagacttg accttggttt actctgctgg acaaggtgac     180
agaggtgcta gaggtgttaa tcacttcggt aacgctggta tgaccgcttc tattgttggt     240
ggtcactgga gatctgctac cagattggct accttggcta tggctgaaca atgtgaaggt     300
tacaacttgc acaaggtgt ttttgaccac ctatacagag ctattgctgg tggtaagcca     360
ggtgttatga ccaagattgg tttgcacacc ttcgttgacc aagaaccgc tcaagacgct     420 agataccacg gtggtgctgt taatgaaaga gctagacaag ctatagctga aggtaaggct     480 tgttggttg acgctgttga cttcagaggt gacgaatact tgttctaccc atctttccca     540
attcactgtg ctttgattag atgtaccgct gctgacgcta gaggtaactt gtctacccac     600
agagaagcat ccaccacga attgttggct atggctcaag ctgctcacaa ctctggtggt     660
attgttattg ctcaagttga atctttggtt gaccaccacg aaatttgca agctattcac     720 gttccaggta ttttggttga ctacgttgtt gtttgtgaca cccagctaa ccaccaaatg     780 accttcgctg aatcttacaa cccagcttac gttacccctt ggcaaggtga agctgctgtt     840
gctgaagctg aagctgctcc agttgcagct ggtccattgg acgctagaac cattgttcaa     900
aggagagctg ttatggaatt ggctagaagg gctccaagag ttgttaattt gggtgttggt     960
atgccagctg ctgttggtat gttggctcac aagcaggat ggacggtttt cacttgacc    1020 gttgaagctg gtccaattgg tggtaccca gctgacggtt tgtctttcgg agcttctgct    1080
tacccagaag ctgttgttga ccaaccagct caattcgact tctacgaagg tggtggtatt    1140
gacttggcta ttttggtttt ggctgaattg acggtcacg gtaacgttaa tgtttctaag    1200
ttcggtgaag gtgaaggtgc ttctatagct ggtgttggtg gtttcattaa cattacccaa    1260
tctgctagag ctgttgtttt catgggtacc ttgaccgctg gtgattgga agttagagct    1320 ggtgacggtg gtttgcaaat tgttagagaa ggtagagtta agaagattgt tcctgaagtt    1380
```

-continued

```
tctcacttgt ctttcaacgg accatacgtt gcttctttgg gtattccagt tttgtacatt    1440
accgaaagag ctgttttcga aatgagagca ggtgctgacg gtgaagctag attgaccttg    1500
gttgaaattg ctccaggtgt tgacttgcaa agagacgttt tggaccaatg ttctacccca    1560
attgctgtag ctcaagactt gagagaaatg gacgctagat tgttccaagc tggaccattg    1620
cacttgtaa                                                            1629
```

<210> SEQ ID NO 62
<211> LENGTH: 542
<212> TYPE: PRT
<213> ORGANISM: Cupriavidus necator
<220> FEATURE:
<223> OTHER INFORMATION: Pct_CN_AA

<400> SEQUENCE: 62

```
Met Lys Val Ile Thr Ala Arg Glu Ala Ala Ala Leu Val Gln Asp Gly
 1               5                  10                  15

Trp Thr Val Ala Ser Ala Gly Phe Val Gly Ala Gly His Ala Glu Ala
                20                  25                  30

Val Thr Glu Ala Leu Glu Gln Arg Phe Leu Gln Ser Gly Leu Pro Arg
            35                  40                  45

Asp Leu Thr Leu Val Tyr Ser Ala Gly Gln Gly Asp Arg Gly Ala Arg
        50                  55                  60

Gly Val Asn His Phe Gly Asn Ala Gly Met Thr Ala Ser Ile Val Gly
    65                  70                  75                  80

Gly His Trp Arg Ser Ala Thr Arg Leu Ala Thr Leu Ala Met Ala Glu
                85                  90                  95

Gln Cys Glu Gly Tyr Asn Leu Pro Gln Gly Val Leu Thr His Leu Tyr
               100                 105                 110

Arg Ala Ile Ala Gly Gly Lys Pro Gly Val Met Thr Lys Ile Gly Leu
           115                 120                 125

His Thr Phe Val Asp Pro Arg Thr Ala Gln Asp Ala Arg Tyr His Gly
       130                 135                 140

Gly Ala Val Asn Glu Arg Ala Arg Gln Ala Ile Ala Glu Gly Lys Ala
145                 150                 155                 160

Cys Trp Val Asp Ala Val Asp Phe Arg Gly Asp Glu Tyr Leu Phe Tyr
                165                 170                 175

Pro Ser Phe Pro Ile His Cys Ala Leu Ile Arg Cys Thr Ala Ala Asp
            180                 185                 190

Ala Arg Gly Asn Leu Ser Thr His Arg Glu Ala Phe His His Glu Leu
        195                 200                 205

Leu Ala Met Ala Gln Ala Ala His Asn Ser Gly Gly Ile Val Ile Ala
    210                 215                 220

Gln Val Glu Ser Leu Val Asp His His Glu Ile Leu Gln Ala Ile His
225                 230                 235                 240

Val Pro Gly Ile Leu Val Asp Tyr Val Val Cys Asp Asn Pro Ala
                245                 250                 255

Asn His Gln Met Thr Phe Ala Glu Ser Tyr Asn Pro Ala Tyr Val Thr
            260                 265                 270

Pro Trp Gln Gly Glu Ala Ala Val Ala Glu Ala Glu Ala Ala Pro Val
        275                 280                 285

Ala Ala Gly Pro Leu Asp Ala Arg Thr Ile Val Gln Arg Arg Ala Val
    290                 295                 300

Met Glu Leu Ala Arg Arg Ala Pro Arg Val Val Asn Leu Gly Val Gly
305                 310                 315                 320
```

```
Met Pro Ala Ala Val Gly Met Leu Ala His Gln Ala Gly Leu Asp Gly
            325                 330                 335

Phe Thr Leu Thr Val Glu Ala Gly Pro Ile Gly Thr Pro Ala Asp
        340                 345                 350

Gly Leu Ser Phe Gly Ala Ser Ala Tyr Pro Glu Ala Val Val Asp Gln
            355                 360                 365

Pro Ala Gln Phe Asp Phe Tyr Glu Gly Gly Ile Asp Leu Ala Ile
        370                 375                 380

Leu Gly Leu Ala Glu Leu Asp Gly His Gly Asn Val Asn Val Ser Lys
385                 390                 395                 400

Phe Gly Glu Gly Glu Gly Ala Ser Ile Ala Gly Val Gly Gly Phe Ile
                405                 410                 415

Asn Ile Thr Gln Ser Ala Arg Ala Val Val Phe Met Gly Thr Leu Thr
                420                 425                 430

Ala Gly Gly Leu Glu Val Arg Ala Gly Asp Gly Gly Leu Gln Ile Val
            435                 440                 445

Arg Glu Gly Arg Val Lys Lys Ile Val Pro Glu Val Ser His Leu Ser
    450                 455                 460

Phe Asn Gly Pro Tyr Val Ala Ser Leu Gly Ile Pro Val Leu Tyr Ile
465                 470                 475                 480

Thr Glu Arg Ala Val Phe Glu Met Arg Ala Gly Ala Asp Gly Glu Ala
                485                 490                 495

Arg Leu Thr Leu Val Glu Ile Ala Pro Gly Val Asp Leu Gln Arg Asp
            500                 505                 510

Val Leu Asp Gln Cys Ser Thr Pro Ile Ala Val Ala Gln Asp Leu Arg
        515                 520                 525

Glu Met Asp Ala Arg Leu Phe Gln Ala Gly Pro Leu His Leu
        530                 535                 540

<210> SEQ ID NO 63
<211> LENGTH: 6360
<212> TYPE: DNA
<213> ORGANISM: Artificial Sequence
<220> FEATURE:
<223> OTHER INFORMATION: pYP004

<400> SEQUENCE: 63
gagctcgtag gaacaatttc gggcccctgc gtgttcttct gaggttcatc ttttacattt      60
gcttctgctg gataattttc agaggcaaca aggaaaaatt agatggcaaa aagtcgtctt     120
tcaaggaaaa atccccacca tctttcgaga tccctgtaa cttattggca actgaaagaa      180 tgaaaggag gaaatacaa atatactag aactgaaaaa aaaaaagtat aaatagagac        240
gatatatgcc aatacttcac aatgttcgaa tctattcttc atttgcagct attgtaaaat    300
aataaaacat caagaacaaa caagctcaac ttgtcttttc taagaacaaa gaataaacac    360
aaaaacaaaa agttttttta attttaatca aaaagttaac atgcatcacc atcaccatca    420
cactagtgga tccccgggc tgcaggaatt cgatatcaag cttatcgata ccgtcgacct      480
cgagtcatgt aattagttat gtcacgctta cattcacgcc ctccccccac atccgctcta    540
accgaaaagg aaggagttag acaacctgaa gtctaggtcc ctatttattt ttttatagtt    600
atgttagtat taagaacgtt atttatattt caaattttc tttttttttct gtacagacgc    660 gtgtacgcat gtaacattat actgaaaacc ttgcttgaga aggttttggg acgctcgaag    720
gctttaattt gcggccggta cccaattcgc cctatagtga gtcgtattac gcgcgctcac    780
```

```
tggccgtcgt tttacaacgt cgtgactggg aaaaccctgg cgttacccaa cttaatcgcc    840
ttgcagcaca tccccctttc gccagctggc gtaatagcga agaggcccgc accgatcgcc    900
cttcccaaca gttgcgcagc ctgaatggcg aatggcgcga cgcgccctgt agcggcgcat    960
taagcgcggc gggtgtggtg gttacgcgca gcgtgaccgc tacacttgcc agcgccctag   1020
cgcccgctcc tttcgctttc ttcccttcct ttctcgccac gttcgccggc tttccccgtc   1080
aagctctaaa tcgggggctc cctttagggt tccgatttag tgctttacgg cacctcgacc   1140
ccaaaaaact tgattagggt gatggttcac gtagtgggcc atcgccctga tagacggttt   1200
ttcgcccttt gacgttggag tccacgttct ttaatagtgg actcttgttc caaactggaa   1260
caacactcaa ccctatctcg gtctattctt ttgatttata agggattttg ccgatttcgg   1320
cctattggtt aaaaaatgag ctgatttaac aaaaatttaa cgcgaatttt aacaaaatat   1380
taacgtttac aatttcctga tgcggtattt tctccttacg catctgtgcg gtatttcaca   1440
ccgcataggg taataactga tataattaaa ttgaagctct aatttgtgag tttagtatac   1500
atgcatttac ttataataca gttttttagt tttgctggcc gcatcttctc aaatatgctt   1560
cccagcctgc ttttctgtaa cgttcaccct taccttagc atcccttccc tttgcaaata   1620
gtcctcttcc aacaataata atgtcagatc ctgtagagac cacatcatcc acggttctat   1680
actgttgacc caatgcgtct cccttgtcat ctaaacccac accgggtgtc ataatcaacc   1740
aatcgtaacc ttcatctctt ccacccatgt ctctttgagc aataaagccg ataacaaaat   1800
ctttgtcgct cttcgcaatg tcaacagtac ccttagtata ttctccagta gatagggagc   1860
ccttgcatga caattctgct aacatcaaaa ggcctctagg ttcctttgtt acttcttctg   1920
ccgcctgctt caaaccgcta acaatacctg ggcccaccac accgtgtgca ttcgtaatgt   1980
ctgcccattc tgctattctg tatacacccg cagagtactg caatttgact gtattaccaa   2040
tgtcagcaaa ttttctgtct tcgaagagta aaaaattgta cttggcggat aatgccttta   2100
gcggcttaac tgtgccctcc atggaaaaat cagtcaagat atccacatgt gttttagta   2160
aacaaatttt gggacctaat gcttcaacta actccagtaa ttccttggtg gtacgaacat   2220
ccaatgaagc acacaagttt gtttgctttt cgtgcatgat attaaatagc ttggcagcaa   2280
caggactagg atgagtagca gcacgttcct tatatgtagc tttcgacatg atttatcttc   2340
gtttcctgca ggttttgtt ctgtgcagtt gggttaagaa tactgggcaa tttcatgttt   2400
cttcaacact acatatgcgt atatatacca atctaagtct gtgctccttc cttcgttctt   2460
ccttctgttc ggagattacc gaatcaaaaa aatttcaaag aaaccgaaat caaaaaaaag   2520
aataaaaaaa aaatgatgaa ttgaattgaa aagctgtggt atggtgcact ctcagtacaa   2580
tctgctctga tgccgcatag ttaagccagc cccgacaccc gccaacaccc gctgacgcgc   2640
cctgacgggc ttgtctgctc ccggcatccg cttacagaca agctgtgacc gtctccggga   2700
gctgcatgtg tcagaggttt tcaccgtcat caccgaaacg cgcgagacga aagggcctcg   2760
tgatacgcct atttttatag gttaatgtca tgataataat ggtttcttag tatgatccaa   2820
tatcaaagga aatgatagca ttgaaggatg agactaatcc aattgaggag tggcagcata   2880
tagaacagct aaagggtagt gctgaaggaa gcatacgata cccgcatgg aatgggataa   2940
tatcacagga ggtactagac tacctttcat cctacataaa tagacgcata aagtacgca   3000
tttaagcata aacacgcact atgccgttct tctcatgtat atatatatac aggcaacacg   3060
cagatatagg tgcgacgtga acagtgagct gtatgtgcgc agctcgcgtt gcattttcgg   3120
aagcgctcgt tttcggaaac gctttgaagt tcctattccg aagttcctat tctctagaaa   3180
```

```
gtataggaac ttcagagcgc ttttgaaaac caaaagcgct ctgaagacgc actttcaaaa   3240
aaccaaaaac gcaccggact gtaacgagct actaaaatat tgcgaatacc gcttccacaa   3300
acattgctca aaagtatctc tttgctatat atctctgtgc tatatcccta tataacctac   3360
ccatccacct ttcgctcctt gaacttgcat ctaaactcga cctctacatt ttttatgttt   3420
atctctagta ttactcttta gacaaaaaaa ttgtagtaag aactattcat agagtgaatc   3480
gaaaacaata cgaaaatgta aacatttcct atacgtagta tatagagaca aaatagaaga   3540
aaccgttcat aattttctga ccaatgaaga atcatcaacg ctatcacttt ctgttcacaa   3600
agtatgcgca atccacatcg gtatagaata taatcgggga tgcctttatc ttgaaaaaat   3660
gcacccgcag cttcgctagt aatcagtaaa cgcgggaagt ggagtcaggc ttttttatg    3720 gaagagaaaa tagacaccaa agtagccttc ttctaacctt aacggaccta cagtgcaaaa   3780
agttatcaag agactgcatt atagagcgca caaaggagaa aaaagtaat  ctaagatgct   3840 ttgttagaaa aatagcgctc tcgggatgca ttttttgtaga acaaaaaaga agtatagatt  3900
ctttgttggt aaaatagcgc tctcgcgttg catttctgtt ctgtaaaaat gcagctcaga   3960
ttctttgttt gaaaaattag cgctctcgcg ttgcattttt gttttacaaa aatgaagcac   4020
agattcttcg ttggtaaaat agcgctttcg cgttgcattt ctgttctgta aaaatgcagc   4080
tcagattctt tgtttgaaaa attagcgctc tcgcgttgca ttttttgttct acaaaatgaa   4140 gcacagatgc ttcgttcagg tggcactttt cggggaaatg tgcgcggaac ccctatttgt   4200
ttatttttct aaatacattc aaatatgtat ccgctcatga caataaccc tgataaatg     4260 cttcaataat attgaaaaag gaagagtatg agtattcaac atttccgtgt cgcccttatt   4320 ccctttttg cggcattttg ccttcctgtt tttgctcacc cagaaacgct ggtgaaagta   4380
aaagatgctg aagatcagtt gggtgcacga gtgggttaca tcgaactgga tctcaacagc  4440
ggtaagatcc ttgagagttt tcgccccgaa gaacgttttc caatgatgag cactttttaaa  4500 gttctgctat gtggcgcggt attatcccgt attgacgccg ggcaagagca actcggtcgc  4560
cgcatacact attctcagaa tgacttggtt gagtactcac cagtcacaga aaagcatctt   4620
acggatggca tgacagtaag agaattatgc agtgctgcca taaccatgag tgataacact  4680
gcggccaact tacttctgac aacgatcgga ggaccgaagg agctaaccgc ttttttgcac  4740
aacatggggg atcatgtaac tcgccttgat cgttgggaac cggagctgaa tgaagccata  4800
ccaaacgacg agcgtgacac cacgatgcct gtagcaatgg caacaacgtt gcgcaaacta  4860
ttaactggcg aactacttac tctagcttcc cggcaacaat taatagactg gatggaggcg  4920
gataaagttg caggaccact tctgcgctcg gcccttccgg ctggctggtt tattgctgat  4980
aaatctggag ccggtgagcg tgggtctcgc ggtatcattg cagcactggg gccagatggt  5040
aagccctccc gtatcgtagt tatctacacg acggggagtc aggcaactat ggatgaacga  5100
aatagacaga tcgctgagat aggtgcctca ctgattaagc attggtaact gtcagaccaa  5160
gtttactcat atatacttta gattgattta aaacttcatt tttaatttaa aaggatctag  5220
gtgaagatcc tttttgataa tctcatgacc aaaatccctt aacgtgagtt ttcgttccac  5280
tgagcgtcag accccgtaga aaagatcaaa ggatcttctt gagatccttt ttttctgcgc  5340
gtaatctgct gcttgcaaac aaaaaaacca ccgctaccag cggtggtttg tttgccggat  5400
caagagctac caactctttt tccgaaggta actggcttca gcagagcgca gataccaaat  5460
actgtccttc tagtgtagcc gtagttaggc caccacttca agaactctgt agcaccgcct  5520
```

| | |
|---|---|
| acatacctcg ctctgctaat cctgttacca gtggctgctg ccagtggcga taagtcgtgt | 5580 |
| cttaccgggt tggactcaag acgatagtta ccggataagg cgcagcggtc gggctgaacg | 5640 |
| gggggttcgt gcacacagcc cagcttggag cgaacgacct acaccgaact gagataccta | 5700 |
| cagcgtgagc tatgagaaag cgccacgctt cccgaaggga gaaaggcgga caggtatccg | 5760 |
| gtaagcggca gggtcggaac aggagagcgc acgagggagc ttccaggggg aaacgcctgg | 5820 |
| tatctttata gtcctgtcgg gtttcgccac ctctgacttg agcgtcgatt tttgtgatgc | 5880 |
| tcgtcagggg ggcggagcct atggaaaaac gccagcaacg cggcctttt acggttcctg | 5940 |
| gccttttgct ggccttttgc tcacatgttc tttcctgcgt tatcccctga ttctgtggat | 6000 |
| aaccgtatta ccgcctttga gtgagctgat accgctcgcc gcagccgaac gaccgagcgc | 6060 |
| agcgagtcag tgagcgagga agcggaagag cgcccaatac gcaaaccgcc tctccccgcg | 6120 |
| cgttggccga ttcattaatg cagctggcac gacaggtttc ccgactggaa agcgggcagt | 6180 |
| gagcgcaacg caattaatgt gagttacctc actcattagg caccccaggc tttacacttt | 6240 |
| atgcttccgg ctcctatgtt gtgtggaatt gtgagcggat aacaatttca cacaggaaac | 6300 |
| agctatgacc atgattacgc caagcgcgca attaaccctc actaagggga acaaaagctg | 6360 |

<210> SEQ ID NO 64
<211> LENGTH: 6907
<212> TYPE: DNA
<213> ORGANISM: Artificial Sequence
<220> FEATURE:
<223> OTHER INFORMATION: pYP083

<400> SEQUENCE: 64

| | |
|---|---|
| cagcgacatg gaggcccaga ataccctcct tgacagtctt gacgtgcgca gctcaggggc | 60 |
| atgatgtgac tgtcgcccgt acatttagcc catacatccc catgtataat catttgcatc | 120 |
| catacatttt gatggccgca cggcgcgaag caaaaattac ggctcctcgc tgcagacctg | 180 |
| cgagcaggga aacgctcccc tcacagacgc gttgaattgt ccccacgccg cgcccctgta | 240 |
| gagaaatata aaaggttagg atttgccact gaggttcttc tttcatatac ttcctttaa | 300 |
| aatcttgcta ggatacagtt ctcacatcac atccgaacat aaacaaccat gggtaaggaa | 360 |
| aagactcacg tttcgaggcc gcgattaaat tccaacatgg atgctgattt atatgggtat | 420 |
| aaatgggctc gcgataatgt cgggcaatca ggtgcgacaa tctatcgatt gtatgggaag | 480 |
| cccgatgcgc cagagttgtt tctgaaacat ggcaaaggta gcgttgccaa tgatgttaca | 540 |
| gatgagatgg tcagactaaa ctggctgacg gaatttatgc ctcttccgac catcaagcat | 600 |
| tttatccgta ctcctgatga tgcatggtta ctcaccactg cgatccccgg caaaacagca | 660 |
| ttccaggtat tagaagaata tcctgattca ggtgaaaata ttgttgatgc gctggcagtg | 720 |
| ttcctgcgcc ggttgcattc gattcctgtt tgtaattgtc ttttaacag cgatcgcgta | 780 |
| tttcgtctcg ctcaggcgca atcacgaatg aataacggtt tggttgatgc gagtgatttt | 840 |
| gatgacgagc gtaatggctg gcctgttgaa caagtctgga agaaatgca taagcttttg | 900 |
| ccattctcac cggattcagt cgtcactcat ggtgatttct cacttgataa ccttatttt | 960 |
| gacgagggga aattaatagg ttgtattgat gttggacgag tcggaatcgc agaccgatac | 1020 |
| caggatcttg ccatcctatg gaactgcctc ggtgagtttt ctccttcatt acagaaacgg | 1080 |
| ctttttcaaa aatatggtat tgataatcct gatatgaata aattgcagtt tcatttgatg | 1140 |
| ctcgatgagt ttttctaatc agtactgaca ataaaaagat tcttgttttc aagaacttgt | 1200 |
| catttgtata gttttttat attgtagttg ttctatttta atcaaatgtt agcgtgattt | 1260 |

```
atatttttt tcgcctcgac atcatctgcc cagatgcgaa gttaagtgcg cagaaagtaa      1320
tatcatgcgt caatcgtatg tgaatgctgg tcgctatact gctgtcgatt cgatactaac      1380
gccgccatcc agtgtcgaaa acgcggtgtg aaataccgca cagatgcgta aggagaaaat      1440
accgcatgag ctcgtaggaa caatttcggg cccctgcgtg ttcttctgag gttcatcttt      1500
tacatttgct tctgctggat aattttcaga ggcaacaagg aaaaattaga tggcaaaaag      1560
tcgtctttca aggaaaaatc cccaccatct ttcgagatcc cctgtaactt attggcaact      1620
gaaagaatga aaggaggaa atacaaaat atactagaac tgaaaaaaa aaagtataaa         1680
tagagacgat atatgccaat acttcacaat gttcgaatct attcttcatt tgcagctatt      1740
gtaaaataat aaaacatcaa gaacaaacaa gctcaacttg tcttttctaa gaacaaagaa      1800
taaacacaaa aacaaaaagt ttttttaatt ttaatcaaaa agaattcaaa acgatgcatc      1860
accatcacca ccacgagact atgcagacta tcgacttctc attccaggtt agaaagtgtc      1920
agccagagtt gatcgctcca gctaacccaa ctccatacga gttcaagcaa ttgtccgacg      1980
ttgacgacca acagtccttg agattccagt tgccattggt aacatctac caccacaacc       2040
catccttgga gggtagagat ccagttaagg ttatcaaaga ggctatcgct aaggctttgg      2100
ttttctacta cccattggct ggtagattga gagagggtcc tggtagaaag ttgttcgttg      2160
agtgtactgg tgagggtatc ttgttcattg aagctgacgc tgacgtttcc ttggagcagt      2220
tcagagatac tttgccatac tccttgtcct ccatggaaaa caacatcatc cacaactcat      2280
tgaactccga cggtgttttg aactccccctt tgttgttgat ccaggttact agattgaagt     2340
gtggtggttt catcttcggt atccacttcg accacactat ggctgacggt tttggtatcg      2400
ctcagttcat gaaggctatt gctgagatcg ctagaggtgc tttcgctcca tctatttttgc     2460
cagtttggca gagagctttg ttgactgcta gagatcctcc aagaatcact gttagacact      2520
acgagtacga ccaggttgtt gacactaagt ccactttgat cccagctaac aacatgatcg      2580
acagattgtt cttcttcact cagagacaga tctccacatt gagacagact ttgccagctc      2640
acttgcacga ctgttcttca ttcgaggttt tgactgctta cgtttgggaga ttgagaacta    2700
tcgcttttcca gttgaagcca gaggaagagg ttagattctt gtgtgttgtt aacttgagat     2760
ccaagatcga catcccattg ggtttctacg gtaacgctat cgttttccca gctgttatca      2820
ctactgttgc taagttgtgt ggtaacccctt tgggttacgc tgttgacttg atcagaaagg    2880
ctaaggctaa agctacaaaa gagtacatca agtccatggt tgacttcatg gttatcaagg      2940
gtagaccaag attcactgag atcggtccat tcatgatgtc cgacattact agaatcggtt      3000
tcgagaacgt tgacttcggt tggggtaagg ctattttcgg tggtccaatt atcggtggtt      3060
gtggtatcat cagaggtatg atctcttact ccattgcttt catgaacaga aacggtgaga      3120
agggaatcgt tgttccattg tgtttgccac caccagctat ggaaagattc agagctaacg      3180
ttcacgcttc cttgcaggtt atccaggttt tggacaaggt tgacagagac atgcaaacaa      3240
tcttgtccgc tttgtaaagg ggcggccgct catgtaatta gttatgtcac gcttacattc      3300
acgccctccc cccacatccg ctctaaccga aaggaagga gttagacaac ctgaagtcta       3360
ggtcccctatt tatttttta tagttatgtt agtattaaga acgttattta tatttcaaat      3420
ttttctttt tttctgtaca gacgcgtgta cgcatgtaac attatactga aaaccttgct       3480
tgagaaggtt ttgggacgct cgaaggcttt aatttgcggc cggtacccaa ttcgccgaac      3540
cgtaaaaagg ccgcgttgct ggcgtttttc cataggctcc gccccctga cgagcatcac      3600
```

```
aaaaatcgac gctcaagtca gaggtggcga aacccgacag gactataaag ataccaggcg    3660
tttccccctg gaagctccct cgtgcgctct cctgttccga ccctgccgct taccggatac    3720
ctgtccgcct ttctcccttc gggaagcgtg gcgctttctc atagctcacg ctgtaggtat    3780
ctcagttcgg tgtaggtcgt tcgctccaag ctgggctgtg tgcacgaacc ccccgttcag    3840
cccgaccgct gcgccttatc cggtaactat cgtcttgagt ccaacccggt aagacacgac    3900
ttatcgccac tggcagcagc cactggtaac aggattagca gagcgaggta tgtaggcggt    3960
gctacagagt tcttgaagtg gtggcctaac tacggctaca ctagaaggac agtatttggt    4020
atctgcgctc tgctgaagcc agttaccttc ggaaaaagag ttggtagctc ttgatccggc    4080
aaacaaacca ccgctggtag cggtggtttt tttgtttgca agcagcagat tacgcgcaga    4140
aaaaaaggat ctcaagaaga tcctttgatc ttttctacgg ggtctgacgc tcagtggaac    4200
gaaaactcac gttaagggat tttggtcatg agattatcaa aaaggatctt cacctagatc    4260
cttttaaatt aaaaatgaag ttttaaatca atctaaagta tatatgagta aacttggtct    4320
gacagttacc aatgcttaat cagtgaggca cctatctcag cgatctgtct atttcgttca    4380
tccatagttg cctgactccc cgtcgtgtag ataactacga tacgggaggg cttaccatct    4440
ggccccagtg ctgcaatgat accgcgagac ccacgctcac cggctccaga tttatcagca    4500
ataaaccagc cagccggaag ggccgagcgc agaagtggtc ctgcaacttt atccgcctcc    4560
atccagtcta ttaattgttg ccgggaagct agagtaagta gttcgccagt taatagtttg    4620
cgcaacgttg ttgccattgc tacaggcatc gtggtgtcac gctcgtcgtt tggtatggct    4680
tcattcagct ccggttccca acgatcaagg cgagttacat gatccccat gttgtgcaaa    4740 aaagcggtta gctccttcgg tcctccgatc gttgtcagaa gtaagttggc cgcagtgtta    4800
tcactcatgg ttatggcagc actgcataat tctcttactg tcatgccatc cgtaagatgc    4860
ttttctgtga ctggtgagta ctcaaccaag tcattctgag aatagtgtat gcggcgaccg    4920
agttgctctt gcccggcgtc aatacgggat aataccgcgc cacatagcag aactttaaaa    4980
gtgctcatca ttggaaaacg ttcttcgggg cgaaaactct caaggatctt accgctgttg    5040
agatccagtt cgatgtaacc cactcgtgca cccaactgat cttcagcatc ttttactttc    5100
accagcgttt ctgggtgagc aaaaacagga aggcaaaatg ccgcaaaaaa gggaataagg    5160
gcgacacgga aatgttgaat actcatactc ttcctttttc aatattattg aagcatttat    5220
cagggttatt gtctcatgag cggatacata tttgaatgta tttagaaaaa taaacaaata    5280
ggggttccgc gcacatttcc ccgaaaagtg ccacctgaac gaagcatctg tgcttcattt    5340
tgtagaacaa aaatgcaacg cgagagcgct aattttcaa acaaagaatc tgagctgcat    5400
ttttacagaa cagaaatgca acgcgaaagc gctattttac caacgaagaa tctgtgcttc    5460 attttttgtaa aacaaaaatg caacgcgaga gcgctaattt ttcaaacaaa gaatctgagc    5520
tgcattttta cagaacagaa atgcaacgcg agagcgctat tttaccaaca aagaatctat    5580
acttcttttt tgttctacaa aaatgcatcc cgagagcgct atttttctaa caaagcatct    5640
tagattactt ttttttctcct tgtgcgctc tataatgcag tctcttgata acttttttgca    5700 ctgtaggtcc gttaaggtta gaagaaggct actttggtgt ctattttctc ttccataaaa    5760
aaagcctgac tccacttccc gcgttactg attactagcg aagctgcggg tgcatttttt    5820
caagataaag gcatcccga ttatattcta taccgatgtg gattgcgcat actttgtgaa    5880
cagaaagtga tagcgttgat gattcttcat tggtcagaaa attatgaacg gtttcttcta    5940
ttttgtctct atatactacg tataggaaat gtttacattt tcgtattgtt ttcgattcac    6000
```

```
tctatgaata gttcttacta caattttttt gtctaaagag taatactaga gataaacata    6060
aaaaatgtag aggtcgagtt tagatgcaag ttcaaggagc gaaaggtgga tgggtaggtt    6120
atatagggat atagcacaga gatatatagc aaagagatac ttttgagcaa tgtttgtgga    6180
agcggtattc gcaatatttt agtagctcgt tacagtccgg tgcgtttttg gttttttgaa    6240
agtgcgtctt cagagcgctt ttggttttca aaagcgctct gaagttccta tactttctag    6300
agaataggaa cttcggaata ggaacttcaa agcgtttccg aaaacgagcg cttccgaaaa    6360
tgcaacgcga gctgcgcaca tacagctcac tgttcacgtc gcacctatat ctgcgtgttg    6420
cctgtatata tatatacatg agaagaacgg catagtgcgt gtttatgctt aaatgcgtac    6480
ttatatgcgt ctatttatgt aggatgaaag gtagtctagt acctcctgtg atattatccc    6540
attccatgcg gggtatcgta tgcttccttc agcactaccc tttagctgtt ctatatgctg    6600
ccactcctca attggattag tctcatcctt caatgctatc atttcctttg atattggatc    6660
atactaagaa accattatta tcatgacatt aacctataaa aataggcgta tcacgaggcc    6720
ctttcgtctc gcgcgtttcg gtgatgacgg tgaaaacctc tgacacatgc agctcccgga    6780
gacggtcaca gcttgtctgt aagcggatgc cgggagcaga caagcccgtc agggcgcgtc    6840
agcgggtgtt ggcgggtgtc ggggctggct taactatgcg gcatcagagc agattgtact    6900
gagagtg                                                             6907

<210> SEQ ID NO 65
<211> LENGTH: 8270
<212> TYPE: DNA
<213> ORGANISM: Artificial Sequence
<220> FEATURE:
<223> OTHER INFORMATION: pYP096

<400> SEQUENCE: 65
acaggaaaca gctatgacca tgattacgcc aagcgcgcaa ttaaccctca ctaaagggaa      60
caaaagctgg agctcaagtc caatgctagt agagaagggg ggtaacaccc ctccgcgctc     120
ttttccgatt ttttttctaaa ccgtggaata tttcggatat ccttttgttg tttccgggtg    180
tacaatatgg acttcctctt ttctggcaac caaacccata catcgggatt cctataatac     240
cttcgttggt ctccctaaca tgtaggtggc ggaggggaga tatacaatag aacagatacc     300
agacaagaca taatgggcta acaagactac accaattac actgcctcat tgatggtggt     360
acataacgaa ctaatactgt agccctagac ttgatagcca tcatcatatc gaagtttcac     420
tacccttttt ccatttgcca tctattgaag taataatagg cgcatgcaac ttcttttctt     480
tttttttctt ttctctctcc cccgttgttg tctcaccata tccgcaatga caaaaaaatg     540
atggaagaca ctaaaggaaa aaattaacga caaagacagc accaacagat gtcgttgttc     600
cagagctgat gagggtatc tcgaagcaca cgaaactttt ccttccttc attcacgcac       660 actactctct aatgagcaac ggtatacggc cttccttcca gttacttgaa tttgaaataa     720
aaaaaagttt gctgtcttgc tatcaagtat aaatagacct gcaattatta atcttttgtt     780
tcctcgtcat tgttctcgtt cccttttctt cttgtttctt tttctgcaca atatttcaag     840
ctataccaag catacaatca actatctcat atacagttaa catgcatcac catcaccatc     900
acactagtgg atccatgaga aaggttgaaa ttattaccgc tgaacaagct gctcaattgg     960
ttaaggacaa cgacaccatt acctctattg gtttcgtttc ttctgctcac ccagaagctt    1020
tgaccaaggc tttggaaaag agattcttgg acaccaacac cccacaaaac ttgacctaca    1080
```

```
tttacgctgg ttctcaaggt aagagagacg gtagagctgc tgaacacttg gctcacaccg    1140
gtttgttgaa gagagctatt attggtcact ggcaaaccgt tccagctatt ggtaagttgg    1200
ctgttgaaaa caagattgaa gcttacaact tctctcaagg taccttggtt cactggttca    1260
gagctttggc tggtcacaag ttgggtgttt tcaccgacat tggtttggaa accttcttgg    1320
acccaagaca attgggtggt aagttgaacg acgttaccaa ggaagacttg gttaagttga    1380
ttgaagttga cggtcacgaa caattgttct acccaacctt cccagttaac gttgctttct    1440
tgagaggtac ctacgctgac gaatctggta acattactat ggacgaagaa attggtccat    1500
tcgaatctac ctctgttgct caagctgttc acaactgtgg tggtaaggtt gttgttcaag    1560
ttaaggacgt tgttgctcac ggttctttgg acccaagaat ggttaagatt ccaggtattt    1620
acgttgacta cgttgttgtt gctgctccag aagaccacca acaaacctac gactgtgaat    1680
acgacccatc tttgtctggt gaacacagag ctccagaagg tgctaccgac gctgctttgc    1740
caatgtctgc taagaagatt attggtagaa gaggtgcttt ggaattgacc gaaaacgctg    1800
ttgttaactt gggtgttggt gctccagaat acgttgcttc tgttgctggt gaagaaggta    1860
ttgctgacac cattaccttg accgttgaag gtggtgctat tggtggtgtt ccacaaggtg    1920
gtgctagatt cggttcttca agaaacgctg acgctattat tgaccacacc taccaattcg    1980
acttctacga cggtggtggt ttggacattg cttacttggg tttggctcaa tgtgacggtt    2040
ctggtaacat taacgtttct aagttcggta ccaacgttgc tggttgtggt ggtttcccaa    2100
acatttctca acaaccccca acgtttact tctgtggtac cttcaccgct ggtggtttga    2160
agattgctgt tgaagacggt aaggttaaga ttttgcaaga aggtaaggct aagaagttca    2220
ttaaggctgt tgaccaaatt accttcaacg gttcttacgc tgctagaaac ggtaagcacg    2280
ttttgtacat taccgaaaga tgtgttttcg aattgaccaa ggaaggtttg aagttgattg    2340
aagttgctcc aggtattgac attgaaaagg acattttggc tcacatggac ttcaagccaa    2400
ttattgacaa cccaaagttg atggacgcta gattgttcca agacggtcca atgggtttga    2460
agaagtaacc cgggctgcag gaattcgata tcaagcttat cgataccgtc gacctcgagt    2520
gaagttttgt tagaaaataa atcattttt aattgagcat tcttattcct attttattta    2580
aatagtttta tgtattgtta gctacataca acagtttaaa tcaaattttc ttttttccaa    2640
gtccaaaatg gaggtttatt ttgatgaccc gcatgcgatt atgttttgaa agtataagac    2700
tacatacatg tacatatatt taaacatgta aacccgtcca ttatattgct tactttcttc    2760
ttttttgccg ttttgacttg gacctctggt ttgctatttc cttacaatct ttgctacaat    2820
cggccggtac ccaattcgcc ctatagtgag tcgtattacg cgcgctcact ggccgtcgtt    2880
ttacaacgtc gtgactggga aaaccctggc gttacccaac ttaatcgcct tgcagcacat    2940
ccccctttcg ccagctggcg taatagcgaa gaggcccgca ccgatcgccc ttcccaacag    3000
ttgcgcagcc tgaatggcga atggcgcgac gcgcctgta gcggcgcatt aagcgcggcg    3060
ggtgtggtgg ttacgcgcag cgtgaccgct acacttgcca gcgccctagc gcccgctcct    3120
ttcgctttct tcccttcctt tctcgccacg ttcgccggct ttccccgtca gctctaaat    3180 cgggggctcc ctttagggtt ccgatttagt gctttacggc acctcgaccc caaaaaactt    3240
gattagggtg atggttcacg tagtgggcca tcgccctgat agacggtttt tcgccctttg    3300
acgttggagt ccacgttctt taatagtgga ctcttgttcc aaactggaac aacactcaac    3360
cctatctcgg tctattcttt tgatttataa gggattttgc cgatttcggc ctattggtta    3420
aaaaatgagc tgatttaaca aaaatttaac gcgaattta acaaaatatt aacgtttaca    3480
```

```
atttcctgat gcggtatttt ctccttacgc atctgtgcgg tatttcacac cgcataggca    3540
agtgcacaaa caatacttaa ataaatacta ctcagtaata acctatttct tagcattttt    3600
gacgaaattt gctattttgt tagagtcttt tacaccattt gtctccacac ctccgcttac    3660
atcaacacca ataacgccat ttaatctaag cgcatcacca acatttttctg gcgtcagtcc    3720 accagctaac ataaaatgta agctttcggg gctctcttgc cttccaaccc agtcagaaat    3780
cgagttccaa tccaaaagtt cacctgtccc acctgcttct gaatcaaaca agggaataaa    3840
cgaatgaggt ttctgtgaag ctgcactgag tagtatgttg cagtcttttg gaaatacgag    3900
tcttttaata actggcaaac cgaggaactc ttggtattct tgccacgact catctccatg    3960
cagttggacg atatcaatgc cgtaatcatt gaccagagcc aaaacatcct ccttaggttg    4020
attacgaaac acgccaacca agtatttcgg agtgcctgaa ctattttat atgcttttac    4080 aagacttgaa attttccttg caataaccgg gtcaattgtt ctctttctat tgggcacaca    4140 tataatacccc agcaagtcag catcggaatc tagagcacat tctgcggcct ctgtgctctg    4200
caagccgcaa actttcacca atggaccaga actacctgtg aaattaataa cagacatact    4260
ccaagctgcc tttgtgtgct taatcacgta tactcacgtg ctcaatagtc accaatgccc    4320
tccctcttgg ccctctcctt ttcttttttc gaccgaatta attcttaatc ggcaaaaaaa    4380
gaaaagctcc ggatcaagat tgtacgtaag gtgacaagct attttcaat aaagaatatc    4440 ttccactact gccatctggc gtcataactg caaagtacac atatattacg atgctgtcta    4500
ttaaatgctt cctatattat atatatagta atgtcgttta tggtgcactc tcagtacaat    4560
ctgctctgat gccgcatagt taagccagcc ccgacacccg ccaacacccg ctgacgcgcc    4620
ctgacgggct tgtctgctcc cggcatccgc ttacagacaa gctgtgaccg tctccgggag    4680
ctgcatgtgt cagaggtttt caccgtcatc accgaaacgc gcgagacgaa agggcctcgt    4740
gatacgccta tttttatagg ttaatgtcat gataataatg gtttcttaat atgatccaat    4800
atcaaaggaa atgatagcat tgaaggatga gactaatcca attgaggagt ggcagcatat    4860
agaacagcta aagggtagtg ctgaaggaag catacgatac cccgcatgga atgggataat    4920
atcacaggag gtactagact acctttcatc ctacataaat agacgcatat aagtacgcat    4980
ttaagcataa acacgcacta tgccgttctt ctcatgtata tatatataca ggcaacacgc    5040
agatataggt gcgacgtgaa cagtgagctg tatgtgcgca gctcgcgttg cattttcgga    5100
agcgctcgtt ttcggaaacg ctttgaagtt cctattccga agttcctatt ctctagaaag    5160
tataggaact tcgagcgct tttgaaaacc aaaagcgctc tgaagacgca ctttcaaaaa    5220
accaaaaacg caccggactg taacgagcta ctaaaatatt gcgaataccg cttccacaaa    5280
cattgctcaa aagtatctct ttgctatata tctctgtgct atatccctat ataacctacc    5340
catccacctt tcgctccttg aacttgcatc taaactcgac ctctacattt tttatgttta    5400
tctctagtat tactctttag acaaaaaaat tgtagtaaga actattcata gagtgaatcg    5460
aaaacaatac gaaaatgtaa acatttccta tacgtagtat atagagacaa aatagaagaa    5520
accgttcata attttctgac caatgaagaa tcatcaacgc tatcactttc tgttcacaaa    5580
gtatgcgcaa tccacatcgg tatagaatat aatcggggat gcctttatct tgaaaaaatg    5640
cacccgcagc ttcgctagta atcagtaaac gcgggaagtg gagtcaggct ttttttatgg    5700
aagagaaaat agacaccaaa gtagccttct tctaacctta acggacctac agtgcaaaaa    5760
gttatcaaga gactgcatta tagagcgcac aaaggagaaa aaaagtaatc taagatgctt    5820
```

-continued

```
tgttagaaaa atagcgctct cgggatgcat ttttgtagaa caaaaaagaa gtatagattc    5880
tttgttggta aaatagcgct ctcgcgttgc atttctgttc tgtaaaaatg cagctcagat    5940
tctttgtttg aaaaattagc gctctcgcgt tgcatttttg ttttacaaaa atgaagcaca    6000
gattcttcgt tggtaaaata gcgctttcgc gttgcatttc tgttctgtaa aaatgcagct    6060
cagattcttt gtttgaaaaa ttagcgctct cgcgttgcat ttttgttcta caaaatgaag    6120
cacagatgct tcgttcaggt ggcacttttc ggggaaatgt gcgcggaacc cctatttgtt    6180 tattttcta aatacattca aatatgtatc cgctcatgag acaataaccc tgataaatgc    6240
ttcaataata ttgaaaaagg aagagtatga gtattcaaca tttccgtgtc gcccttattc    6300
ccttttttgc ggcattttgc cttcctgttt ttgctcaccc agaaacgctg gtgaaagtaa    6360
aagatgctga agatcagttg ggtgcacgag tgggttacat cgaactggat ctcaacagcg    6420
gtaagatcct tgagagtttt cgccccgaag aacgttttcc aatgatgagc acttttaaag    6480
ttctgctatg tggcgcggta ttatcccgta ttgacgccgg gcaagagcaa ctcggtcgcc    6540
gcatacacta ttctcagaat gacttggttg agtactcacc agtcacagaa aagcatctta    6600
cggatggcat gacagtaaga gaattatgca gtgctgccat aaccatgagt gataacactg    6660
cggccaactt acttctgaca acgatcggag gaccgaagga gctaaccgct tttttgcaca    6720
acatggggga tcatgtaact cgccttgatc gttgggaacc ggagctgaat gaagccatac    6780
caaacgacga gcgtgacacc acgatgcctg tagcaatggc aacaacgttg cgcaaactat    6840
taactggcga actacttact ctagcttccc ggcaacaatt aatagactgg atggaggcgg    6900
ataaagttgc aggaccactt ctgcgctcgg cccttccggc tggctggttt attgctgata    6960
aatctggagc cggtgagcgt gggtctcgcg gtatcattgc agcactgggg ccagatggta    7020
agccctcccg tatcgtagtt atctacacga cggggagtca ggcaactatg gatgaacgaa    7080
atagacagat cgctgagata ggtgcctcac tgattaagca ttggtaactg tcagaccaag    7140
tttactcata tatactttag attgatttaa aacttcattt ttaatttaaa aggatctagg    7200
tgaagatcct ttttgataat ctcatgacca aaatccctta acgtgagttt tcgttccact    7260
gagcgtcaga ccccgtagaa aagatcaaag gatcttcttg agatcctttt tttctgcgcg    7320
taatctgctg cttgcaaaca aaaaaaccac cgctaccagc ggtggtttgt ttgccggatc    7380
aagagctacc aactcttttt ccgaaggtaa ctggcttcag cagagcgcag ataccaaata    7440
ctgtccttct agtgtagccg tagttaggcc accacttcaa gaactctgta gcaccgccta    7500
catacctcgc tctgctaatc ctgttaccag tggctgctgc cagtggcgat aagtcgtgtc    7560
ttaccgggtt ggactcaaga cgatagttac cggataaggc gcagcggtcg ggctgaacgg    7620
ggggttcgtg cacacagccc agcttggagc gaacgaccta caccgaactg agatacctac    7680
agcgtgagct atgagaaagc gccacgcttc ccgaagggag aaaggcggac aggtatccgg    7740
taagcggcag ggtcggaaca ggagagcgca cgagggagct tccaggggga aacgcctggt    7800
atctttatag tcctgtcggg tttcgccacc tctgacttga gcgtcgattt ttgtgatgct    7860
cgtcaggggg gcggagccta tggaaaaacg ccagcaacgc ggcctttta cggttcctgg    7920 ccttttgctg gccttttgct cacatgttct ttcctgcgtt atcccctgat tctgtggata    7980
accgtattac cgcctttgag tgagctgata ccgctcgccg cagccgaacg accgagcgca    8040
gcgagtcagt gagcgaggaa gcggaagagc gcccaatacg caaaccgcct ctccccgcgc    8100
gttggccgat tcattaatgc agctggcacg acaggtttcc cgactggaaa gcgggcagtg    8160
agcgcaacgc aattaatgtg agttacctca ctcattaggc accccaggct ttacacttta    8220
```
tgcttccggc tcctatgttg tgtggaattg tgagcggata acaatttcac        8270

<210> SEQ ID NO 66
<211> LENGTH: 8347
<212> TYPE: DNA
<213> ORGANISM: Artificial Sequence
<220> FEATURE:
<223> OTHER INFORMATION: pYP106

<400> SEQUENCE: 66
ctcaagtcca atgctagtag agaagggggg taacacccct ccgcgctctt ttccgatttt      60
tttctaaacc gtggaatatt tcggatatcc ttttgttgtt tccgggtgta caatatggac     120
ttcctctttt ctggcaacca aacccataca tcgggattcc tataatacct tcgttggtct     180
ccctaacatg taggtggcgg aggggagata tacaatagaa cagataccag acaagacata     240
atgggctaaa caagactaca ccaattacac tgcctcattg atggtggtac ataacgaact     300
aatactgtag ccctagactt gatagccatc atcatatcga agtttcacta cccttttttcc    360
atttgccatc tattgaagta ataataggcg catgcaactt cttttctttt tttttctttt     420
ctctctcccc cgttgttgtc tcaccatatc cgcaatgaca aaaaaatgat ggaagacact     480
aaaggaaaaa attaacgaca aagacagcac caacagatgt cgttgttcca gagctgatga     540
ggggtatctc gaagcacacg aaactttttc cttccttcat tcacgcacac tactctctaa     600
tgagcaacgg tatacggcct tccttccagt tacttgaatt tgaaataaaa aaagtttgc      660
tgtcttgcta tcaagtataa atagacctgc aattattaat cttttgtttc ctcgtcattg     720
ttctcgttcc ctttcttcct tgtttctttt tctgcacaat atttcaagct ataccaagca     780
tacaatcaac tatctcatat acagttaaca tgcatcacca tcaccatcac actagtggat     840
ccatgaaggt tattaccgca agagaagctg ctgcattggt tcaagacggt tggaccgttg     900
cttctgctgg tttcgttggt gctggtcacg ctgaagctgt taccgaagca ttggaacaaa     960
gattcttgca atctggattg ccaagagact tgaccttggt ttactctgct ggacaaggtg    1020
acagaggtgc tagaggtgtt aatcacttcg gtaacgctgg tatgaccgct tctattgttg    1080
gtggtcactg gagatctgct accagattgg ctaccttggc tatggctgaa caatgtgaag    1140
gttacaactt gccacaaggt gttttgaccc acctatacag agctattgct ggtggtaagc    1200
caggtgttat gaccaagatt ggtttgcaca ccttcgttga cccaagaacc gctcaagacg    1260
ctagatacca cggtggtgct gttaatgaaa gagctagaca agctatagct gaaggtaagg    1320
cttgttgggt tgacgctgtt gacttcagag gtgacgaata cttgttctac ccatcttttcc    1380
caattcactg tgctttgatt agatgtaccg ctgctgacgc tagaggtaac ttgtctaccc    1440
acagagaagc attccaccac gaattgttgg ctatggctca agctgctcac aactctggtg    1500
gtattgttat tgctcaagtt gaatctttgg ttgaccacca cgaaattttg caagctattc    1560
acgttccagg tattttggtt gactacgttg ttgtttgtga caacccagct aaccaccaaa    1620
tgaccttcgc tgaatcttac aacccagctt acgttacccc ttggcaaggt gaagctgctg    1680
ttgctgaagc tgaagctgct ccagttgcag ctggtccatt ggacgctaga accattgttc    1740
aaaggagagc tgttatggaa ttggctagaa gggctccaag agttgttaat ttgggtgttg    1800
gtatgccagc tgctgttggt atgttggctc accaagcagg attggacggt tcacccttga    1860
ccgttgaagc tggtccaatt ggtggtaccc cagctgacgg tttgtctttc ggagcttctg    1920
cttacccaga agctgttgtt gaccaaccag ctcaattcga cttctacgaa ggtggtggta    1980

```
ttgacttggc tattttgggt ttggctgaat tggacggtca cggtaacgtt aatgtttcta   2040
agttcggtga aggtgaaggt gcttctatag ctggtgttgg tggtttcatt aacattaccc   2100
aatctgctag agctgttgtt ttcatgggta ccttgaccgc tggtggattg aagttagag    2160
ctggtgacgt tggtttgcaa attgttagag aaggtagagt taagaagatt gttcctgaag   2220
tttctcactt gtcttcaac ggaccatacg ttgcttcttt gggtattcca gttttgtaca    2280
ttaccgaaag agctgttttc gaaatgagag caggtgctga cggtgaagct agattgacct   2340
tggttgaaat tgctccaggt gttgacttgc aaagagacgt tttggaccaa tgttctaccc   2400
caattgctgt agctcaagac ttgagagaaa tggacgctag attgttccaa gctggaccat   2460
tgcacttgta ataacccggg ctgcaggaat tcgatatcaa gcttatcgat accgtcgacc   2520
tcgaggaagt tttgttagaa ataaatcat ttttaattg agcattctta ttcctatttt     2580
atttaaatag ttttatgtat tgttagctac atacaacagt ttaaatcaaa ttttcttttt   2640
cccaagtcca aaatggaggt ttattttgat gacccgcatg cgattatgtt ttgaaagtat   2700
aagactacat acatgtacat atatttaaac atgtaaaccc gtccattata ttgcttactt   2760
tcttcttttt tgccgttttg acttggacct ctggtttgct atttccttac aatctttgct   2820
acaatcggcc ggtacccaat cgcctata gtgagtcgta ttacgcgcgc tcactggccg     2880
tcgttttaca acgtcgtgac tgggaaaacc ctggcgttac ccaacttaat cgccttgcag   2940
cacatccccc tttcgccagc tggcgtaata gcgaagaggc ccgcaccgat cgcccttccc   3000
aacagttgcg cagcctgaat ggcgaatggc gcgacgcgcc ctgtagcggc gcattaagcg   3060
cggcgggtgt ggtggttacg cgcagcgtga ccgctacact tgccagcgcc ctagcgcccg   3120
ctcctttcgc tttcttccct tcctttctcg ccacgttcgc cggctttccc cgtcaagctc   3180
taaatcgggg gctccctta gggttccgat ttagtgcttt acggcacctc gaccccaaaa   3240
aacttgatta gggtgatggt tcacgtagtg gccatcgcc ctgatagacg ttttttcgcc    3300
ctttgacgtt ggagtccacg ttctttaata gtggactctt gttccaaact ggaacaacac   3360
tcaaccctat ctcggtctat tcttttgatt tataagggat tttgccgatt tcggcctatt   3420
ggttaaaaaa tgagctgatt taacaaaaat ttaacgcgaa ttttaacaaa atattaacgt   3480
ttacaatttc ctgatgcggt attttctcct tacgcatctg tgcggtattt cacaccgcat   3540
aggcaagtgc acaaacaata cttaaataaa tactactcag taataaccta tttcttagca   3600
tttttgacga aatttgctat tttgttagag tcttttacac catttgtctc cacacctccg   3660
cttacatcaa caccaataac gccatttaat ctaagcgcat caccaacatt ttctggcgtc   3720
agtccaccag ctaacataaa atgtaagctt tcggggctct cttgccttcc aacccagtca   3780
gaaatcgagt tccaatccaa aagttcacct gtcccacctg cttctgaatc aaacaaggga   3840
ataaacgaat gaggtttctg tgaagctgca ctgagtagta tgttgcagtc ttttggaaat   3900
acgagtcttt taataactgg caaaccgagg aactcttggt attcttgcca cgactcatct   3960
ccatgcagtt ggacgatatc aatgccgtaa tcattgacca gagccaaaac atcctcctta   4020
ggttgattac gaaacacgcc aaccaagtat ttcggagtgc ctgaactatt tttatatgct   4080
tttacaagac ttgaaatttt ccttgcaata accgggtcaa ttgttctctt tctattgggc   4140
acacatataa tacccagcaa gtcagcatcg gaatctagag cacattctgc ggcctctgtg   4200
ctctgcaagc cgcaaacttt caccaatgga ccagaactac ctgtgaaatt aataacagac   4260
atactccaag ctgcctttgt gtgcttaatc acgtatactc acgtgctcaa tagtcaccaa   4320
tgccctccct cttggccctc tccttttctt ttttcgaccg aattaattct taatcggcaa   4380
```

```
aaaaagaaaa gctccggatc aagattgtac gtaaggtgac aagctatttt tcaataaaga    4440
atatcttcca ctactgccat ctggcgtcat aactgcaaag tacacatata ttacgatgct    4500
gtctattaaa tgcttcctat attatatata tagtaatgtc gtttatggtg cactctcagt    4560
acaatctgct ctgatgccgc atagttaagc cagccccgac acccgccaac acccgctgac    4620
gcgccctgac gggcttgtct gctcccggca tccgcttaca gacaagctgt gaccgtctcc    4680
gggagctgca tgtgtcagag gttttcaccg tcatcaccga aacgcgcgag acgaaagggc    4740
ctcgtgatac gcctattttt ataggttaat gtcatgataa taatggtttc ttaatatgat    4800
ccaatatcaa aggaaatgat agcattgaag gatgagacta atccaattga ggagtggcag    4860
catatagaac agctaaaggg tagtgctgaa ggaagcatac gatacccgc atggaatggg     4920 ataatatcac aggaggtact agactacctt tcatcctaca taaatagacg catataagta    4980
cgcatttaag cataaacacg cactatgccg ttcttctcat gtatatatat atacaggcaa    5040
cacgcagata taggtgcgac gtgaacagtg agctgtatgt gcgcagctcg cgttgcattt    5100
tcggaagcgc tcgttttcgg aaacgctttg aagttcctat tccgaagttc ctattctcta    5160
gaaagtatag gaacttcaga gcgcttttga aaaccaaaag cgctctgaag acgcactttc    5220
aaaaaaccaa aaacgcaccg gactgtaacg agctactaaa atattgcgaa taccgcttcc    5280
acaaacattg ctcaaaagta tctctttgct atatatctct gtgctatatc cctatataac    5340
ctacccatcc acctttcgct ccttgaactt gcatctaaac tcgacctcta catttttttat    5400 gtttatctct agtattactc tttagacaaa aaaattgtag taagaactat tcatagagtg    5460
aatcgaaaac aatacgaaaa tgtaaacatt tcctatacgt agtatataga gacaaaatag    5520
aagaaaccgt tcataatttt ctgaccaatg aagaatcatc aacgctatca ctttctgttc    5580
acaaagtatg cgcaatccac atcggtatag aatataatcg gggatgcctt tatcttgaaa    5640
aaatgcaccc gcagcttcgc tagtaatcag taaacgcggg aagtggagtc aggcttttt     5700 tatggaagag aaaatagaca ccaaagtagc cttcttctaa ccttaacgga cctacagtgc    5760
aaaaagttat caagagactg cattatagag cgcacaaagg agaaaaaaag taatctaaga    5820
tgctttgtta gaaaaatagc gctctcggga tgcatttttg tagaacaaaa aagaagtata    5880
gattctttgt tggtaaaata gcgctctcgc gttgcatttc tgttctgtaa aaatgcagct    5940
cagattcttt gtttgaaaaa ttagcgctct cgcgttgcat ttttgtttta caaaaatgaa    6000
gcacagattc ttcgttggta aaatagcgct ttcgcgttgc atttctgttc tgtaaaaatg    6060
cagctcagat tctttgtttg aaaaattagc gctctcgcgt tgcattttg ttctacaaaa     6120 tgaagcacag atgcttcgtt caggtggcac ttttcgggga aatgtgcgcg aacccctat     6180 ttgtttattt ttctaaatac attcaaatat gtatccgctc atgagacaat aaccctgata    6240
aatgcttcaa taatattgaa aaaggaagag tatgagtatt caacatttcc gtgtcgccct    6300
tattcccttt tttgcggcat tttgccttcc tgttttgct cacccagaaa cgctggtgaa      6360
agtaaaagat gctgaagatc agttgggtgc acgagtgggt tacatcgaac tggatctcaa    6420
cagcggtaag atccttgaga gttttcgccc cgaagaacgt tttccaatga tgagcacttt    6480
taaagttctg ctatgtggcg cggtattatc ccgtattgac gccgggcaag agcaactcgg    6540
tcgccgcata cactattctc agaatgactt ggttgagtac tcaccagtca cagaaaagca    6600
tcttacggat ggcatgacag taagagaatt atgcagtgct gccataacca tgagtgataa    6660
cactgcggcc aacttacttc tgacaacgat cggaggaccg aaggagctaa ccgcttttt     6720
```

| | |
|---|---|
| gcacaacatg ggggatcatg taactcgcct tgatcgttgg gaaccggagc tgaatgaagc | 6780 |
| cataccaaac gacgagcgtg acaccacgat gcctgtagca atggcaacaa cgttgcgcaa | 6840 |
| actattaact ggcgaactac ttactctagc ttcccggcaa caattaatag actggatgga | 6900 |
| ggcggataaa gttgcaggac cacttctgcg ctcggccctt ccggctggct ggtttattgc | 6960 |
| tgataaatct ggagccggtg agcgtgggtc tcgcggtatc attgcagcac tggggccaga | 7020 |
| tggtaagccc tcccgtatcg tagttatcta cacgacgggg agtcaggcaa ctatggatga | 7080 |
| acgaaataga cagatcgctg agataggtgc ctcactgatt aagcattggt aactgtcaga | 7140 |
| ccaagtttac tcatatatac tttagattga tttaaaactt catttttaat ttaaaaggat | 7200 |
| ctaggtgaag atcctttttg ataatctcat gaccaaaatc ccttaacgtg agttttcgtt | 7260 |
| ccactgagcg tcagaccccg tagaaaagat caaaggatct tcttgagatc ctttttttct | 7320 |
| gcgcgtaatc tgctgcttgc aaacaaaaaa accaccgcta ccagcggtgg tttgtttgcc | 7380 |
| ggatcaagag ctaccaactc tttttccgaa ggtaactggc ttcagcagag cgcagatacc | 7440 |
| aaatactgtc cttctagtgt agccgtagtt aggccaccac ttcaagaact ctgtagcacc | 7500 |
| gcctacatac ctcgctctgc taatcctgtt accagtggct gctgccagtg gcgataagtc | 7560 |
| gtgtcttacc gggttggact caagacgata gttaccggat aaggcgcagc ggtcgggctg | 7620 |
| aacggggggt tcgtgcacac agcccagctt ggagcgaacg acctacaccg aactgagata | 7680 |
| cctacagcgt gagctatgag aaagcgccac gcttcccgaa gggagaaagg cggacaggta | 7740 |
| tccggtaagc ggcagggtcg gaacaggaga gcgcacgagg gagcttccag ggggaaacgc | 7800 |
| ctggtatctt tatagtcctg tcgggtttcg ccacctctga cttgagcgtc gatttttgtg | 7860 |
| atgctcgtca gggggggcgga gcctatggaa aaacgccagc aacgcggcct ttttacggtt | 7920 |
| cctggccttt tgctggcctt ttgctcacat gttctttcct gcgttatccc ctgattctgt | 7980 |
| ggataaccgt attaccgcct ttgagtgagc tgataccgct cgccgcagcc gaacgaccga | 8040 |
| gcgcagcgag tcagtgagcg aggaagcgga agagcgccca atacgcaaac cgcctctccc | 8100 |
| cgcgcgttgg ccgattcatt aatgcagctg gcacgacagg tttcccgact ggaaagcggg | 8160 |
| cagtgagcgc aacgcaatta atgtgagtta cctcactcat taggcacccc aggctttaca | 8220 |
| ctttatgctt ccggctccta tgttgtgtgg aattgtgagc ggataacaat ttcacacagg | 8280 |
| aaacagctat gaccatgatt acgccaagcg cgcaattaac cctcactaaa gggaacaaaa | 8340 |
| gctggag | 8347 |

<210> SEQ ID NO 67
<211> LENGTH: 7645
<212> TYPE: DNA
<213> ORGANISM: Artificial Sequence
<220> FEATURE:
<223> OTHER INFORMATION: pYP137

<400> SEQUENCE: 67

| | |
|---|---|
| gagctcgtag gaacaatttc gggcccctgc gtgttcttct gaggttcatc ttttacattt | 60 |
| gcttctgctg gataattttc agaggcaaca aggaaaaatt agatggcaaa aagtcgtctt | 120 |
| tcaaggaaaa atccccacca tctttcgaga tcccctgtaa cttattggca actgaaagaa | 180 |
| tgaaaaggag gaaaatacaa aatatactag aactgaaaaa aaaaagtat aaatagagac | 240 |
| gatatatgcc aatacttcac aatgttcgaa tctattcttc atttgcagct attgtaaaat | 300 |
| aataaaacat caagaacaaa caagctcaac ttgtctttc taagaacaaa gaataaacac | 360 |
| aaaaacaaaa agttttttta attttaatca aaagttaac atgcatcacc atcaccatca | 420 |

```
cactagtgga tccatggcag tcctatcctc agctgatagg gctagtaacg aaaagaaggt    480
aaagtcatct tacttcgact tgcctccaat ggaaatgtca gttgcattcc cacaagccac    540
accagcttct acgttccccc cgtgcacttc tgattactat cactttaatg acttgttgac    600
accagaagag caggcaatta gaaagaaggt aagagagtgt atggaaaaag aagttgctcc    660
gattatgact gaatactggg agaaggcaga gtttccattt catataacac ctaagctagg    720
ggctatggga gttgcaggcg gatctatcaa aggttacgg tgtccaggcc taagcatcac     780
agccaatgct atcgcaacag ccgaaattgc aagggttgat gccagttgtt ctacgttcat    840
tttagtccat agttctttag gaatgctgac aattgcttta tgcggtagtg aagcacaaaa    900
agagaaatac cttccatcct tggcacaact aatacagtg gcctgctggg cgcttactga     960
gccagataat ggttctgatg cttcaggatt gggaaccaca cgcgactaagg tggaaggcgg   1020 ttggaagatt aacggtcaaa aaggtggat aggaaactca acattcgcgg atttattgat     1080
tatctttgct agaaacacga ctaccaacca aatcaacggc ttcattgtaa agaaagatgc    1140
tcctggctta aaagcaacca aaatccctaa taaaattggt ttgaggatgg tacaaaacgg    1200
ggatatcttg ttacagaacg tgtttgtgcc cgacgaagat cgtctacccg tgttaattc     1260 tttccaagac acttccaagg tattagcagt ctcacgtgtt atggtagctt ggcagcctat    1320
tggtatctct atgggtatct acgatatgtg tcatagatac ctgaaagaaa ggaagcagtt    1380
tggagctcct ttagctgctt tcaacttaa ccagcaaaaa ttggtacaaa tgttaggaaa     1440
tgttcaagcg atgttcctta tgggctggag attgtgtaag ttatacgaaa ctggtcaaat    1500
gacacctggt caggcgtcat taggtaaggc ttggatatcc tctaaggcaa gagaaacagc    1560
aagtttgggc agagaacttt taggtggaaa cggtatttta gccgatttcc tagttgcgaa    1620
agcattctgt gacttggagc ctatatacac atacgaaggg acttacgata ttaatacatt    1680
agtgacgggg agagaagtta caggcattgc tagtttcaaa ccagctacaa ggtctagatt    1740
ataagcttat cgataccgtc gacctcgagt catgtaatta gttatgtcac gcttacattc    1800
acgccctccc cccacatccg ctctaaccga aaaggaagga gttagacaac ctgaagtcta    1860 ggtcccctatt tattttttta tagttatgtt agtattaaga acgttattta tatttcaaat    1920
tttctttttt tttctgtaca gacgcgtgta cgcatgtaac attatactga aaaccttgct    1980
tgagaaggtt ttgggacgct cgaaggcttt aatttgcggc cggtacccaa ttcgccctat    2040
agtgagtcgt attacgcgcg ctcactggcc gtcgttttac aacgtcgtga ctgggaaaac    2100
cctggcgtta cccaacttaa tcgccttgca gcacatcccc ctttcgccag ctggcgtaat    2160
agcgaagagg cccgcaccga tcgcccttcc caacagttgc gcagcctgaa tggcgaatgg    2220
cgcgacgcgc cctgtagcgg cgcattaagc gcggcgggtg tggtggttac gcgcagcgtg    2280
accgctacac ttgccagcgc cctagcgccc gctcctttcg ctttcttccc ttcctttctc    2340
gccacgttcg ccggctttcc ccgtcaagct ctaaatcggg gctcccttt agggttccga     2400 tttagtgctt tacggcacct cgaccccaaa aaacttgatt agggtgatgg ttcacgtagt    2460
gggccatcgc cctgatagac ggttttcgc cctttgacgt tggagtccac gttctttaat    2520
agtggactct tgttccaaac tggaacaaca ctcaaccta tctcggtcta ttcttttgat     2580
ttataaggga ttttgccgat ttcggcctat tggttaaaaa atgagctgat ttaacaaaaa    2640
tttaacgcga attttaacaa atattaacg tttacaattt cctgatgcgg tattttctcc     2700
ttacgcatct gtgcggtatt tcacaccgca tagggtaata actgatataa ttaaattgaa    2760
```

```
gctctaattt gtgagtttag tatacatgca tttacttata atacagttttt ttagttttgc      2820 tggccgcatc ttctcaaata tgcttcccag cctgctttc tgtaacgttc accctctacc       2880
ttagcatccc ttcccttgc aaatagtcct cttccaacaa taataatgtc agatcctgta       2940
gagaccacat catccacggt tctatactgt tgacccaatg cgtctcccct gtcatctaaa      3000
cccacaccgg gtgtcataat caaccaatcg taaccttcat ctcttccacc catgtctctt     3060
tgagcaataa agccgataac aaaatctttg tcgctcttcg caatgtcaac agtacccta      3120 gtatattctc cagtagatag ggagcccttg catgacaatt ctgctaacat caaaaggcct     3180
ctaggttcct ttgttacttc ttctgccgcc tgcttcaaac cgctaacaat acctgggccc     3240
accacaccgt gtgcattcgt aatgtctgcc cattctgcta ttctgtatac acccgcagag    3300
tactgcaatt tgactgtatt accaatgtca gcaaatttc tgtcttcgaa gagtaaaaaa     3360
ttgtacttgg cggataatgc ctttagcggc ttaactgtgc cctccatgga aaaatcagtc    3420
aagatatcca catgtgtttt tagtaaacaa attttgggac ctaatgcttc aactaactcc   3480
agtaattcct tggtggtacg aacatccaat gaagcacaca agtttgtttg cttttcgtgc    3540
atgatattaa atagcttggc agcaacagga ctaggatgag tagcagcacg ttccttatat    3600
gtagctttcg acatgattta tcttcgtttc ctgcaggttt tgttctgtg cagttgggtt    3660 aagaatactg ggcaattca tgtttcttca acactacata tgcgtatata taccaatcta    3720
agtctgtgct ccttccttcg ttcttccttc tgttcggaga ttaccgaatc aaaaaaattt   3780
caaagaaacc gaaatcaaaa aaagaataa aaaaaaatg atgaattgaa ttgaaaagct    3840
gtggtatggt gcactctcag tacaatctgc tctgatgccg catagttaag ccagccccga    3900
cacccgccaa cacccgctga cgcgccctga cgggcttgtc tgctcccggc atccgcttac   3960
agacaagctg tgaccgtctc cgggagctgc atgtgtcaga ggttttcacc gtcatcaccg   4020
aaacgcgcga gacgaaaggg cctcgtgata cgcctatttt tataggttaa tgtcatgata    4080
ataatggttt cttagtatga tccaatatca aggaaatga tagcattgaa ggatgagact    4140
aatccaattg aggagtggca gcatatagaa cagctaaagg gtagtgctga aggaagcata    4200
cgataccccg catggaatgg gataatatca caggaggtac tagactacct ttcatcctac   4260
ataaatagac gcatataagt acgcatttaa gcataaacac gcactatgcc gttcttctca   4320
tgtatatata tatacaggca acacgcagat ataggtgcga cgtgaacagt gagctgtatg    4380
tgcgcagctc gcgttgcatt ttcggaagcg ctcgttttcg gaaacgcttt gaagttccta    4440
ttccgaagtt cctattctct agaaagtata ggaacttcag agcgcttttg aaaaccaaaa   4500
gcgctctgaa gacgcacttt caaaaaacca aaaacgcacc ggactgtaac gagctactaa   4560
aatattgcga ataccgcttc cacaaacatt gctcaaaagt atctctttgc tatatatctc   4620
tgtgctatat ccctatataa cctacccatc caccttcgc tccttgaact tgcatctaaa   4680
ctcgacctct acatttttta tgtttatctc tagtattact cttagacaa aaaaattgta   4740 gtaagaacta ttcatagagt gaatcgaaaa caatacgaaa atgtaaacat ttcctatacg    4800
tagtatatag agacaaaata gaagaaaccg ttcataattt tctgaccaat gaagaatcat    4860
caacgctatc actttctgtt cacaaagtat gcgcaatcca catcggtata gaatataatc   4920
ggggatgcct ttatcttgaa aaaatgcacc cgcagcttcg ctagtaatca gtaaacgcgg    4980
gaagtggagt caggctttt ttatggaaga gaaatagac accaaagtag ccttcttcta    5040
accttaacgg acctacagtg caaaaagtta tcaagagact gcattataga gcgcacaaag    5100
gagaaaaaaa gtaatctaag atgctttgtt agaaaaatag cgctctcggg atgcattttt   5160
```

```
gtagaacaaa aaagaagtat agattctttg ttggtaaaat agcgctctcg cgttgcattt    5220
ctgttctgta aaaatgcagc tcagattctt tgtttgaaaa attagcgctc tcgcgttgca    5280
tttttgtttt acaaaaatga agcacagatt cttcgttggt aaaatagcgc tttcgcgttg    5340
catttctgtt ctgtaaaaat gcagctcaga ttctttgttt gaaaaattag cgctctcgcg    5400
ttgcattttt gttctacaaa atgaagcaca gatgcttcgt tcaggtggca cttttcgggg    5460
aaatgtgcgc ggaacccta tttgtttatt tttctaaata cattcaaata tgtatccgct    5520
catgagacaa taaccctgat aaatgcttca ataatattga aaaggaaga gtatgagtat    5580 tcaacatttc cgtgtcgccc ttattccctt ttttgcggca ttttgccttc ctgttttgc    5640 tcacccagaa acgctggtga agtaaaaga tgctgaagat cagttgggtg cacgagtggg    5700
ttacatcgaa ctggatctca acagcggtaa gatccttgag agttttcgcc ccgaagaacg    5760
ttttccaatg atgagcactt ttaaagttct gctatgtggc gcggtattat cccgtattga    5820
cgccgggcaa gagcaactcg gtcgccgcat acactattct cagaatgact tggttgagta    5880
ctcaccagtc acagaaaagc atcttacgga tggcatgaca gtaagagaat tatgcagtgc    5940
tgccataacc atgagtgata acactgcggc caacttactt ctgacaacga tcggaggacc    6000
gaaggagcta accgcttttt tgcacaacat ggggatcat gtaactcgcc ttgatcgttg    6060
ggaaccggag ctgaatgaag ccataccaaa cgacgagcgt gacaccacga tgcctgtagc    6120
aatggcaaca acgttgcgca aactattaac tggcgaacta cttactctag cttcccggca    6180
acaattaata gactggatgg aggcggataa agttgcagga ccacttctgc gctcggccct    6240
tccggctggc tggtttattg ctgataaatc tggagccggt gagcgtgggt ctcgcggtat    6300
cattgcagca ctggggccag atggtaagcc ctcccgtatc gtagttatct acacgacggg    6360
gagtcaggca actatggatg aacgaaatag acagatcgct gagataggtg cctcactgat    6420
taagcattgg taactgtcag accaagttta ctcatatata ctttagattg atttaaaact    6480 tcattttta tttaaaagga tctaggtgaa gatcctttt gataatctca tgaccaaaat    6540
cccttaacgt gagttttcgt tccactgagc gtcagacccc gtagaaaaga tcaaaggatc    6600
ttcttgagat cctttttttc tgcgcgtaat ctgctgcttg caaacaaaaa aaccaccgct    6660
accagcggtg gtttgtttgc cggatcaaga gctaccaact ctttttccga aggtaactgg    6720
cttcagcaga gcgcagatac caaatactgt ccttctagtg tagccgtagt taggccacca    6780
cttcaagaac tctgtagcac cgcctacata cctcgctctg ctaatcctgt taccagtggc    6840
tgctgccagt ggcgataagt cgtgtcttac cgggttggac tcaagacgat agttaccgga    6900
taaggcgcag cggtcgggct gaacggggggg ttcgtgcaca cagcccagct tggagcgaac    6960
gacctacacc gaactgagat acctacagcg tgagctatga aaagcgcca cgcttcccga    7020 agggagaaag gcggacaggt atccggtaag cggcagggtc ggaacaggag agcgcacgag    7080
ggagcttcca gggggaaacg cctggtatct ttatagtcct gtcgggtttc gccacctctg    7140
acttgagcgt cgatttttgt gatgctcgtc agggggggcgg agcctatgga aaaacgccag    7200
caacgcggcc ttttttacggt tcctggcctt ttgctggcct tttgctcaca tgttctttcc    7260
tgcgttatcc cctgattctg tggataaccg tattaccgcc tttgagtgag ctgataccgc    7320
tcgccgcagc cgaacgaccg agcgcagcga gtcagtgagc gaggaagcgg aagagcgccc    7380
aatacgcaaa ccgcctctcc ccgcgcgttg gccgattcat taatgcagct ggcacgacag    7440
gtttcccgac tggaaagcgg gcagtgagcg caacgcaatt aatgtgagtt acctcactca    7500
```

-continued

```
ttaggcaccc caggctttac actttatgct tccggctcct atgttgtgtg gaattgtgag    7560
cggataacaa tttcacacag gaaacagcta tgaccatgat tacgccaagc gcgcaattaa    7620
ccctcactaa agggaacaaa agctg                                          7645
```

<210> SEQ ID NO 68
<211> LENGTH: 3755
<212> TYPE: DNA
<213> ORGANISM: Artificial Sequence
<220> FEATURE:
<223> OTHER INFORMATION: pD902e

<400> SEQUENCE: 68

```
cttcagtaat gtcttgtttc ttttgttgca gtggtgagcc attttgactt cgtgaaagtt      60
tctttagaat agttgtttcc agaggccaaa cattccaccc gtagtaaagt gcaagcgtag     120
gaagaccaag actggcataa atcaggtata agtgtcgagc actggcaggt gatcttctga     180
aagtttctac tagcagataa gatccagtag tcatgcatat ggcaacaatg taccgtgtgg     240
atctaagaac gcgtcctact aaccttcgca ttcgttggtc cagtttgttg ttatcgatca     300
acgtgacaag gttgtcgatt ccgcgtaagc atgcataccc aaggacgcct gttgcaattc     360
caagtgagcc agttccaaca atctttgtaa tattagagca cttcattgtg ttgcgcttga     420
aagtaaaatg cgaacaaatt aagagataat ctcgaaaccg cgacttcaaa cgccaatatg     480
atgtgcggca cacaataagc gttcatatcc gctgggtgac tttctcgctt taaaaaatta     540
tccgaaaaaa ttttctagag tgttgttact ttatacttcc ggctcgtata atacgacaag     600
gtgtaaggag gactaaacca tggctaaact cacctctgct gttccagtcc tgactgctcg     660
tgatgttgct ggtgctgttg agttctggac tgatagactc ggtttctccc gtgacttcgt     720
agaggacgac tttgccggtg ttgtacgtga cgacgttacc ctgttcatct ccgcagttca     780
ggaccaggtt gtgccagaca acactctggc atgggtatgg ttcgtggtc tggacgaact     840 gtacgctgag tggtctgagg tcgtgtctac caacttccgt gatgcatctg gtccagctat     900
gaccgagatc ggtgaacagc cctggggtcg tgagtttgca ctgcgtgatc agctggtaa     960 ctgcgtgcat ttcgtcgcag aagaacagga ctaacaattg acaccttacg attatttaga    1020
gagtatttat tagttttatt gtatgtatac ggatgtttta ttatctatt atgcccttat    1080 attctgtaac tatccaaaag tcctatctta tcaagccagc aatctatgtc cgcgaacgtc    1140
aactaaaaat aagcttttta tgctgttctc tctttttttc ccttcggtat aattatacct    1200
tgcatccaca gattctcctg ccaaattttg cataatcctt tacaacatgg ctatatggga    1260
gcacttagcg ccctccaaaa cccatattgc ctacgcatgt ataggtgttt tttccacaat    1320
attttctctg tgctctcttt ttattaaaga gaagctctat atcggagaag cttctgtggc    1380
cgttatattc ggccttatcg tgggaccaca ttgcctgaat tggtttgccc cggaagattg    1440
gggaaacttg gatctgatta ccttagctgc aggtaccact gagcgtcaga ccccgtagaa    1500
aagatcaaag gatcttcttg agatcctttt tttctgcgcg taatctgctg cttgcaaaca    1560
aaaaaaccac cgctaccagc ggtggtttgt ttgccggatc aagagctacc aactcttttt    1620
ccgaaggtaa ctggcttcag cagagcgcag ataccaaata ctgttcttct agtgtagccg    1680
tagttaggcc accacttcaa gaactctgta gcaccgccta catcctcgc tctgctaatc    1740 ctgttaccag tggctgctgc cagtggcgat aagtcgtgtc ttaccgggtt ggactcaaga    1800
cgatagttac cggataaggc gcagcggtcg ggctgaacgg ggggttcgtg cacacagccc    1860
agcttggagc gaacgaccta ccgaactg agatacctac agcgtgagct atgagaaagc    1920
```

```
gccacgcttc ccgaagggag aaaggcggac aggtatccgg taagcggcag ggtcggaaca      1980
ggagagcgca cgagggagct tccagggggga aacgcctggt atctttatag tcctgtcggg      2040
tttcgccacc tctgacttga gcgtcgattt ttgtgatgct cgtcaggggg gcggagccta      2100
tggaaaaacg ccagcaacgc ggccttttta cggttcctgg ccttttgctg ccttttgct       2160 cacatgttct ttcctgcggt acccagatcc aattcccgct ttgactgcct gaaatctcca      2220
tcgcctacaa tgatgacatt tggatttggt tgactcatgt tggtattgtg aaatagacgc      2280
agatcgggaa cactgaaaaa tacacagtta ttattcattt aaataacatc caaagacgaa      2340
aggttgaatg aaacctttt gccatccgac atccacaggt ccattctcac acataagtgc       2400
caaacgcaac aggaggggat acactagcag cagaccgttg caaacgcagg acctccactc      2460
ctcttctcct caacacccac ttttgccatc gaaaaaccag cccagttatt gggcttgatt      2520
ggagctcgct cattccaatt ccttctatta ggctactaac accatgactt tattagcctg      2580
tctatcctgg cccccctggc gaggttcatg tttgtttatt tccgaatgca acaagctccg      2640
cattacaccc gaacatcact ccagatgagg gctttctgag tgtgggtca aatagtttca       2700 tgttccccaa atggcccaaa actgacagtt taaacgctgt cttggaacct aatatgacaa      2760
aagcgtgatc tcatccaaga tgaactaagt ttggttcgtt gaaatgctaa cggccagttg      2820
gtcaaaaaga aacttccaaa agtcggcata ccgtttgtct tgtttggtat tgattgacga      2880
atgctcaaaa ataatctcat taatgcttag cgcagtctct ctatcgcttc tgaaccccgg      2940
tgcacctgtg ccgaaacgca aatggggaaa cacccgcttt ttggatgatt atgcattgtc      3000
tccacattgt atgcttccaa gattctggtg ggaatactgc tgatagccta acgttcatga      3060
tcaaaattta actgttctaa cccctacttg acagcaatat ataaacagaa ggaagctgcc      3120
ctgtcttaaa cctttttttt tatcatcatt attagcttac tttcataatt gcgactggtt      3180
ccaattgaca agcttttgat tttaacgact tttaacgaca acttgagaag atcaaaaaac      3240
aactaattat tgaaagaatt caaaacgatg tttgcaaaag aaggtgaaaa tgaaggttga      3300
aggggcggcc gctcaagagg atgtcagaat gccatttgcc tgagagatgc aggcttcatt      3360
tttgatactt ttttatttgt aacctatata gtataggatt ttttttgtca ttttgtttct      3420
tctcgtacga gcttgctcct gatcagccta tctcgcagca gatgaatatc ttgtggtagg      3480
ggtttgggaa aatcattcga gtttgatgtt tttcttggta tttcccactc ctcttcagag      3540
tacagaagat taagtgaaac cttcgtttgt gcggatccca ccggcgcaat aatatttac       3600 ttattttggt caacccccaaa taggttgatt tcatacttgg ttcattcaaa aataagtagt     3660
cttttgagat ctttcaatat tataataaat atactataac agccgacttg tttcattttc     3720
gcgaatgttc ccccagctta tccaccggcg ggatc                                3755
```

<210> SEQ ID NO 69
<211> LENGTH: 990
<212> TYPE: DNA
<213> ORGANISM: Escherichia coli
<220> FEATURE:
<223> OTHER INFORMATION: ldhA-sc

<400> SEQUENCE: 69

```
atgaagttgg ctgtttactc taccaagcaa tacgacaaga agtacttgca acaagttaac       60
gaatctttcg gtttcgaatt ggaattcttc gacttcttgt tgaccgaaaa gaccgctaag      120
accgctaacg gttgtgaagc tgtttgtatt ttcgttaacg acgacggttc tagaccagtt      180
```

```
ttggaagaat tgaagaagca cggtgttaag tacattgctt tgagatgtgc tggtttcaac    240
aacgttgact tggacgctgc taaggaattg ggtttgaagg ttgttagagt tccagcttac    300
gacccagaag ctgttgctga acacgctatt ggtatgatga tgaccttgaa cagaagaatt    360
cacagagctt accaaagaac cagagacgct aacttctctt tggaaggttt gaccggtttc    420
accatgtacg gtaagaccgc tggtgttatt ggtaccggta agattggtgt tgctatgttg    480
agaattttga agggtttcgg tatgagattg ttggctttcg acccataccc atctgctgct    540
gctttggaat gggtgttga atacgttgac ttgccaacct tgttctctga atctgacgtt    600
atttctttgc actgtccatt gaccccagaa aactaccact tgttaacga gctgctttc    660 gaacaaatga agaacggtgt tatgattgtt aacacctcta gaggtgcttt gattgactct    720
caagctgcta ttgaagcttt gaagaaccaa aagattggtt ctttgggtat ggacgtttac    780
gaaaacgaaa gagacttgtt cttcgaagac aagtctaacg acgttattca agacgacgtt    840
ttcagaagat gtctgctgtt gtcacaacgtt tgttcaccg gtcaccaagc tttcttgacc    900
gctgaagctt tgacctctat ttctcaaacc accttgcaaa acttgtctaa cttggaaaag    960
ggtgaaacct gtccaaacga attggtttaa                                    990
```

<210> SEQ ID NO 70
<211> LENGTH: 329
<212> TYPE: PRT
<213> ORGANISM: Escherichia coli
<220> FEATURE:
<223> OTHER INFORMATION: ldhA-sc_AA

<400> SEQUENCE: 70

```
Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
                20                  25                  30

Leu Leu Thr Glu Lys Thr Ala Lys Thr Ala Asn Gly Cys Glu Ala Val
            35                  40                  45

Cys Ile Phe Val Asn Asp Asp Gly Ser Arg Pro Val Leu Glu Glu Leu
        50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
                100                 105                 110

Met Met Thr Leu Asn Arg Arg Ile His Arg Ala Tyr Gln Arg Thr Arg
            115                 120                 125

Asp Ala Asn Phe Ser Leu Glu Gly Leu Thr Gly Phe Thr Met Tyr Gly
        130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

Pro Ser Ala Ala Ala Leu Glu Leu Gly Val Glu Tyr Val Asp Leu Pro
                180                 185                 190

Thr Leu Phe Ser Glu Ser Asp Val Ile Ser Leu His Cys Pro Leu Thr
            195                 200                 205

Pro Glu Asn Tyr His Leu Leu Asn Glu Ala Ala Phe Glu Gln Met Lys
        210                 215                 220
```

```
Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Asp Val Phe Arg Arg Leu Ser Ala Cys His
        275                 280                 285

Asn Val Leu Phe Thr Gly His Gln Ala Phe Leu Thr Ala Glu Ala Leu
        290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325
```

<210> SEQ ID NO 71
<211> LENGTH: 7337
<212> TYPE: DNA
<213> ORGANISM: Artificial Sequence
<220> FEATURE:
<223> OTHER INFORMATION: pYP024

<400> SEQUENCE: 71

| | |
|---|---|
| ctcgtaggaa caatttcggg cccctgcgtg ttcttctgag gttcatcttt tacatttgct | 60 |
| tctgctggat aattttcaga ggcaacaagg aaaaattaga tggcaaaaag tcgtctttca | 120 |
| aggaaaaatc cccaccatct ttcgagatcc cctgtaactt attggcaact gaaagaatga | 180 |
| aaaggaggaa aatacaaaat atactagaac tgaaaaaaaa aaagtataaa tagagacgat | 240 |
| atatgccaat acttcacaat gttcgaatct attcttcatt tgcagctatt gtaaaataat | 300 |
| aaaacatcaa gaacaaacaa gctcaacttg tcttttctaa gaacaaagaa taaacacaaa | 360 |
| aacaaaaagt tttttttaatt ttaatcaaaa aatgaagttg ctgtttact ctaccaagca | 420 |
| atacgacaag aagtacttgc aacaagttaa cgaatctttc ggtttcgaat tggaattctt | 480 |
| cgacttcttg ttgaccgaaa agaccgctaa gaccgctaac ggttgtgaag ctgtttgtat | 540 |
| tttcgttaac gacgacggtt ctagaccagt tttggaagaa ttgaagaagc acggtgttaa | 600 |
| gtacattgct ttgagatgtg ctggtttcaa caacgttgac ttggacgctg ctaaggaatt | 660 |
| gggtttgaag gttgttagag ttccagctta cgacccagaa gctgttgctg aacacgctat | 720 |
| tggtatgatg atgaccttga acagaagaat tcacagagct taccaaagaa ccagagacgc | 780 |
| taacttctct ttggaaggtt tgaccggttt caccatgtac ggtaagaccg ctggtgttat | 840 |
| tggtaccggt aagattggtg ttgctatgtt gagaattttg aagggtttcg gtatgagatt | 900 |
| gttggctttc gacccatacc catctgctgc tgctttggaa ttgggtgttg aatacgttga | 960 |
| cttgccaacc ttgttctctg aatctgacgt tatttctttg cactgtccat gacccccaga | 1020 |
| aaactaccac ttgttgaacg aagctgcttt cgaacaaatg aagaacggtg ttatgattgt | 1080 |
| taacaccctct agaggtgctt tgattgactc tcaagctgct attgaagctt gaagaaacca | 1140 |
| aaagattggt tctttgggta tggacgtttta cgaaaacgaa agagacttgt tcttcgaaga | 1200 |
| caagtctaac gacgttattc aagacgacgt tttcagaaga ttgtctgctt gtcacaacgt | 1260 |
| tttgttcacc ggtcaccaag cttttcttgac cgctgaagct ttgacctcta tttctcaaac | 1320 |
| caccttgcaa aacttgtcta acttggaaaa gggtgaaacc tgtccaaacg aattggttta | 1380 |
| actcgagtca tgtaattagt tatgtcacgc ttacattcac gccctccccc cacatccgct | 1440 |

```
ctaaccgaaa aggaaggagt tagacaacct gaagtctagg tccctattta ttttttttata   1500
gttatgttag tattaagaac gttatttata tttcaaattt ttcttttttt tctgtacaga   1560
cgcgtgtacg catgtaacat tatactgaaa accttgcttg agaaggtttt gggacgctcg   1620
aaggctttaa tttgcggccg gtacccaatt cgccctatag tgagtcgtat tacgcgcgct   1680
cactggccgt cgttttacaa cgtcgtgact gggaaaaccc tggcgttacc caacttaatc   1740
gccttgcagc acatccccct ttcgccagct ggcgtaatag cgaagaggcc cgcaccgatc   1800
gcccttccca acagttgcgc agcctgaatg gcgaatggcg cgacgcgccc tgtagcggcg   1860
cattaagcgc ggcgggtgtg gtggttacgc gcagcgtgac cgctacactt gccagcgccc   1920
tagcgcccgc tcctttcgct ttcttccctt cctttctcgc cacgttcgcc ggctttcccc   1980
gtcaagctct aaatcggggg ctcccttag ggttccgatt tagtgcttta cggcacctcg   2040
accccaaaaa acttgattag ggtgatggtt cacgtagtgg gccatcgccc tgatagacgg   2100
ttttcgccc tttgacgttg gagtccacgt tctttaatag tggactcttg ttccaaactg   2160
gaacaacact caaccctatc tcggtctatt cttttgattt ataagggatt ttgccgattt   2220
cggcctattg gttaaaaaat gagctgattt aacaaaaatt taacgcgaat tttaacaaaa   2280
tattaacgtt tacaatttcc tgatgcggta ttttctcctt acgcatctgt gcggtatttc   2340
acaccgcata gatccgtcga gttcaagaga aaaaaaaga aaagcaaaa agaaaaaagg   2400
aaagcgcgcc tcgttcagaa tgacacgtat agaatgatgc attaccttgt catcttcagt   2460
atcatactgt tcgtatacat acttactgac attcataggt atacatatat acacatgtat   2520
atatatcgta tgctgcagct ttaaataatc ggtgtcacta cataagaaca cctttggtgg   2580
agggaacatc gttggtacca ttgggcgagg tggcttctct tatggcaacc gcaagagcct   2640
tgaacgcact ctcactacgg tgatgatcat tcttgcctcg cagacaatca acgtggaggg   2700
taattctgct agcctctgca aagctttcaa gaaaatgcgg gatcatctcg caagagagat   2760
ctcctacttt ctcccttgc aaaccaagtt cgacaactgc gtacggcctg ttcgaaagat   2820
ctaccaccgc tctggaaagt gcctcatcca aaggcgcaaa tcctgatcca aacctttta   2880
ctccacgcgc cagtagggcc tctttaaaag cttgaccgag agcaatcccg cagtcttcag   2940
tggtgtgatg gtcgtctatg tgtaagtcac caatgcactc aacgattagc gaccagccgg   3000
aatgcttggc cagagcatgt atcatatggt ccagaaaccc tatacctgtg tggacgttaa   3060
tcacttgcga ttgtgtggcc tgttctgcta ctgcttctgc ctctttttct gggaagatcg   3120
agtgctctat cgctagggga ccacccttta aagagatcgc aatctgaatc ttggtttcat   3180
ttgtaatacg ctttactagg gctttctgct ctgtcatctt tgccttcgtt tatcttgcct   3240
gctcattttt tagtatattc ttcgaagaaa tcacattact ttatataatg tataattcat   3300
tatgtgataa tgccaatcgc taagaaaaaa aaagagtcat ccgctagggg aaaaaaaaaa   3360
atgaaaatca ttaccgaggc ataaaaaaat atagagtgta ctagaggagg ccaagagtaa   3420
tagaaaaaga aaattgcggg aaaggactgt gttatgactt ccctgactaa tgccgtgttc   3480
aaacgatacc tggcagtgac tcctagcgct caccaagctc ttaaaacggg aatttatggt   3540
gcactctcag tacaatctgc tctgatgccg catagttaag ccagcccga cacccgccaa   3600
cacccgctga cgcgccctga cgggcttgtc tgctcccggc atccgcttac agacaagctg   3660
tgaccgtctc cgggagctgc atgtgtcaga ggttttcacc gtcatcaccg aaacgcgcga   3720
gacgaaaggg cctcgtgata cgcctatttt tataggttaa tgtcatgata ataatggttt   3780
```

```
cttagatgat ccaatatcaa aggaaatgat agcattgaag gatgagacta atccaattga   3840
ggagtggcag catatagaac agctaaaggg tagtgctgaa ggaagcatac gatacccgc    3900
atggaatggg ataatatcac aggaggtact agactacctt tcatcctaca taaatagacg   3960
catataagta cgcatttaag cataaacacg cactatgccg ttcttctcat gtatatatat   4020
atacaggcaa cacgcagata taggtgcgac gtgaacagtg agctgtatgt gcgcagctcg   4080
cgttgcattt tcggaagcgc tcgttttcgg aaacgctttg aagttcctat tccgaagttc   4140
ctattctcta gaaagtatag gaacttcaga gcgcttttga aaaccaaaag cgctctgaag   4200
acgcactttc aaaaaaccaa aaacgcaccg gactgtaacg agctactaaa atattgcgaa   4260
taccgcttcc acaaacattg ctcaaaagta tctctttgct atatatctct gtgctatatc   4320
cctatataac ctacccatcc acctttcgct ccttgaactt gcatctaaac tcgacctcta   4380
cattttttat gtttatctct agtattactc tttagacaaa aaaattgtag taagaactat   4440
tcatagagtg aatcgaaaac aatacgaaaa tgtaaacatt tcctatacgt agtatataga   4500
gacaaaatag aagaaaccgt tcataatttt ctgaccaatg aagaatcatc aacgctatca   4560
ctttctgttc acaaagtatg cgcaatccac atcggtatag aatataatcg gggatgcctt   4620
tatcttgaaa aaatgcaccc gcagcttcgc tagtaatcag taaacgcggg aagtggagtc   4680
aggctttttt tatggaagag aaaatagaca ccaaagtagc cttcttctaa ccttaacgga   4740
cctacagtgc aaaaagttat caagagactg cattatagag cgcacaaagg agaaaaaaag   4800
taatctaaga tgctttgtta gaaaaatagc gctctcggga tgcatttttg tagaacaaaa   4860
aagaagtata gattctttgt tggtaaaata gcgctctcgc gttgcatttc tgttctgtaa   4920
aaatgcagct cagattcttt gtttgaaaaa ttagcgctct cgcgttgcat ttttgtttta   4980
caaaaatgaa gcacagattc ttcgttggta aaatagcgct ttcgcgttgc atttctgttc   5040
tgtaaaaatg cagctcagat tctttgtttg aaaaattagc gctctcgcgt tgcatttttg   5100
ttctacaaaa tgaagcacag atgcttcgtt caggtggcac ttttcgggga aatgtgcgcg   5160
gaacccctat ttgtttattt ttctaaatac attcaaatat gtatccgctc atgagacaat   5220
aaccctgata aatgcttcaa taatattgaa aaaggaagag tatgagtatt caacatttcc   5280
gtgtcgccct tattcccttt tttgcggcat tttgccttcc tgttttgct cacccagaaa    5340
cgctggtgaa agtaaaagat gctgaagatc agttgggtgc acgagtgggt tacatcgaac   5400
tggatctcaa cagcggtaag atccttgaga gttttcgccc cgaagaacgt tttccaatga   5460
tgagcacttt taaagttctg ctatgtggcg cggtattatc ccgtattgac gccgggcaag   5520
agcaactcgg tcgccgcata cactattctc agaatgactt ggttgagtac tcaccagtca   5580
cagaaaagca tcttacggat ggcatgacag taagagaatt atgcagtgct gccataacca   5640
tgagtgataa cactgcggcc aacttacttc tgacaacgat cggaggaccg aaggagctaa   5700
ccgctttttt gcacaacatg ggggatcatg taactcgcct tgatcgttgg aaccggagc    5760
tgaatgaagc cataccaaac gacgagcgtg acaccacgat gcctgtagca atggcaacaa   5820
cgttgcgcaa actattaact ggcgaactac ttactctagc ttcccggcaa caattaatag   5880
actggatgga ggcggataaa gttgcaggac cacttctgcg ctcggccctt ccggctggct   5940
ggtttattgc tgataaatct ggagccggtg agcgtgggtc tcgcggtatc attgcagcac   6000
tggggccaga tggtaagccc tcccgtatcg tagttatcta cacgacgggg agtcaggcaa   6060
ctatggatga acgaaataga cagatcgctg agataggtgc ctcactgatt aagcattggt   6120
aactgtcaga ccaagtttac tcatatatac tttagattga tttaaaactt cattttaat    6180
```

```
ttaaaaggat ctaggtgaag atccttttg ataatctcat gaccaaaatc ccttaacgtg    6240
agttttcgtt ccactgagcg tcagaccccg tagaaaagat caaaggatct tcttgagatc    6300 cttttttct gcgcgtaatc tgctgcttgc aaacaaaaaa accaccgcta ccagcggtgg     6360
tttgtttgcc ggatcaagag ctaccaactc tttttccgaa ggtaactggc ttcagcagag    6420
cgcagatacc aaatactgtc cttctagtgt agccgtagtt aggccaccac ttcaagaact    6480
ctgtagcacc gcctacatac ctcgctctgc taatcctgtt accagtggct gctgccagtg    6540
gcgataagtc gtgtcttacc gggttggact caagacgata gttaccggat aaggcgcagc    6600
ggtcgggctg aacgggggt tcgtgcacac agcccagctt ggagcgaacg acctacaccg     6660
aactgagata cctacagcgt gagctatgag aaagcgccac gcttcccgaa gggagaaagg    6720
cggacaggta tccggtaagc ggcagggtcg gaacaggaga gcgcacgagg gagcttccag    6780
ggggaaacgc ctggtatctt tatagtcctg tcgggtttcg ccacctctga cttgagcgtc    6840
gatttttgtg atgctcgtca gggggcgga gcctatggaa aaacgccagc aacgcggcct     6900
ttttacggtt cctggccttt tgctggcctt ttgctcacat gttctttcct gcgttatccc    6960
ctgattctgt ggataaccgt attaccgcct ttgagtgagc tgataccgct cgccgcagcc    7020
gaacgaccga gcgcagcgag tcagtgagcg aggaagcgga agagcgccca atacgcaaac    7080
cgcctctccc cgcgcgttgg ccgattcatt aatgcagctg gcacgacagg tttcccgact    7140
ggaaagcggg cagtgagcgc aacgcaatta atgtgagtta cctcactcat taggcacccc    7200
aggctttaca ctttatgctt ccggctccta tgttgtgtgg aattgtgagc ggataacaat    7260
ttcacacagg aaacagctat gaccatgatt acgccaagcg cgcaattaac cctcactaaa    7320
gggaacaaaa gctggag                                                   7337
```

FERMENTATIVE PRODUCTION OF N-BUTYLACRYLATE USING ALCOHOL ACYL TRANSFERASE ENZYMES

FIELD OF THE INVENTION

The invention is directed to a recombinant nucleic acid molecule, a recombinant microorganism and to a method for fermentative production of n-butylacrylate and other esters from alcohols and acyl-CoA units using alcohol acyl transferase enzymes.

BACKGROUND

Acrylate esters are among the most versatile monomers for providing performance properties to a wide variety of polymers. Acrylate esters are chemically produced with acrylic acid and alcohols. For instance, n-butylacrylate (n-BA) is produced by esterifying acrylate with butanol.

Production of n-BA in a biological system has not been demonstrated. A pathway for the production of n-BA in a biological system may comprise an acryloyl-CoA biosynthesis pathway and a butanol biosynthesis pathway. In addition, for fermentative production of n-BA, an alcohol acyl transferase (AAT) enzyme, capable of catalysing an esterification reaction between acryloyl-CoA and butanol, forming an ester bond, would need to be present in a production system, such as a microorganism. Currently, multiple pathways have been reported for the production of acryloyl-CoA or butanol in a biological system via natural or engineered pathways (Teufel, Kung et al. 2009) (Schadeweg and Boles 2016).

Also, various publications describe AAT enzyme activities that combine acyl-CoAs with alcohols through ester formation (El-Sharkawy, Manriquez et al. 2005). They show that some AATs have broad substrate specificities resulting in various ester products. However, no AAT enzymes capable of forming n-BA esters in a biological system by esterification of acryloyl-CoA and butanol were described known.

The physiological properties of acryloyl-CoA and butanol and their intermediates limited the functionality and/or the capacity of fermentative production of these products in microorganisms (Zhou, Zhang et al. 2011). Many difficulties, such as reducing power imbalance, toxicity, ATP imbalance, and oxygen sensitivity of enzymes also make the development of engineered strain to produce acryl ester cumbersome.

Especially, acrylate, butanol, and n-BA are toxic to the cells. Although, there are some examples in public for producing acrylate and butanol by fermentation separately in yeast and various other host strains, there is no reported biological method to produce n-butyl acrylate in a biological system due to the lack of adequate AAT enzymes catalysing the esterification reaction.

Today n-BA is mainly produced from chemical methods based on petroleum based feedstock. Availability of a sustainable method for producing acrylate esters is becoming interesting. One way for such a sustainable method could be a biological system for fermentative production of acrylate esters from renewable feed stock, such as glucose or lignocellulose. Fermentative n-BA production is hypothetically possible, if acryloyl-CoA and butanol are produced in a cell and subsequently combined to form n-BA by an AAT enzyme. Identifying AAT enzymes catalysing this esterification step is a key challenge for providing such fermentative production system.

SUMMARY

It is therefore one objective of the invention at hand to provide AAT enzymes having an activity of esterifying acryloyl-CoA and butanol to form n-BA. Furthermore, it is an objective of the invention at hand to develop a microorganism capable of fermentative production of n-BA by esterification of acryloyl-CoA and butanol and to provide fermentation systems for the production of n-BA.

It is an additional objective of the invention at hand to provide AAT enzymes having an activity of esterifying propionyl-CoA and butanol to form butylpropionate and/or of esterifying lactoyl-CoA and butanol to form butyl lactate and or of esterifying acetyl-CoA and ethanol to form ethyl acetate. Further it is an objective of the invention at hand to develop microorganisms capable of fermentative production of butyl propionate, butyl lactate and/or ethyl acetate by esterification of propionyl-CoA and butanol, lactoyl-CoA and butanol and/or acetyl-CoA and ethanol, respectively and to provide fermentation systems for the production of butyl propionate, butyl lactate and/or ethyl acetate.

DETAILED DESCRIPTION OF THE INVENTION

Figure 1:
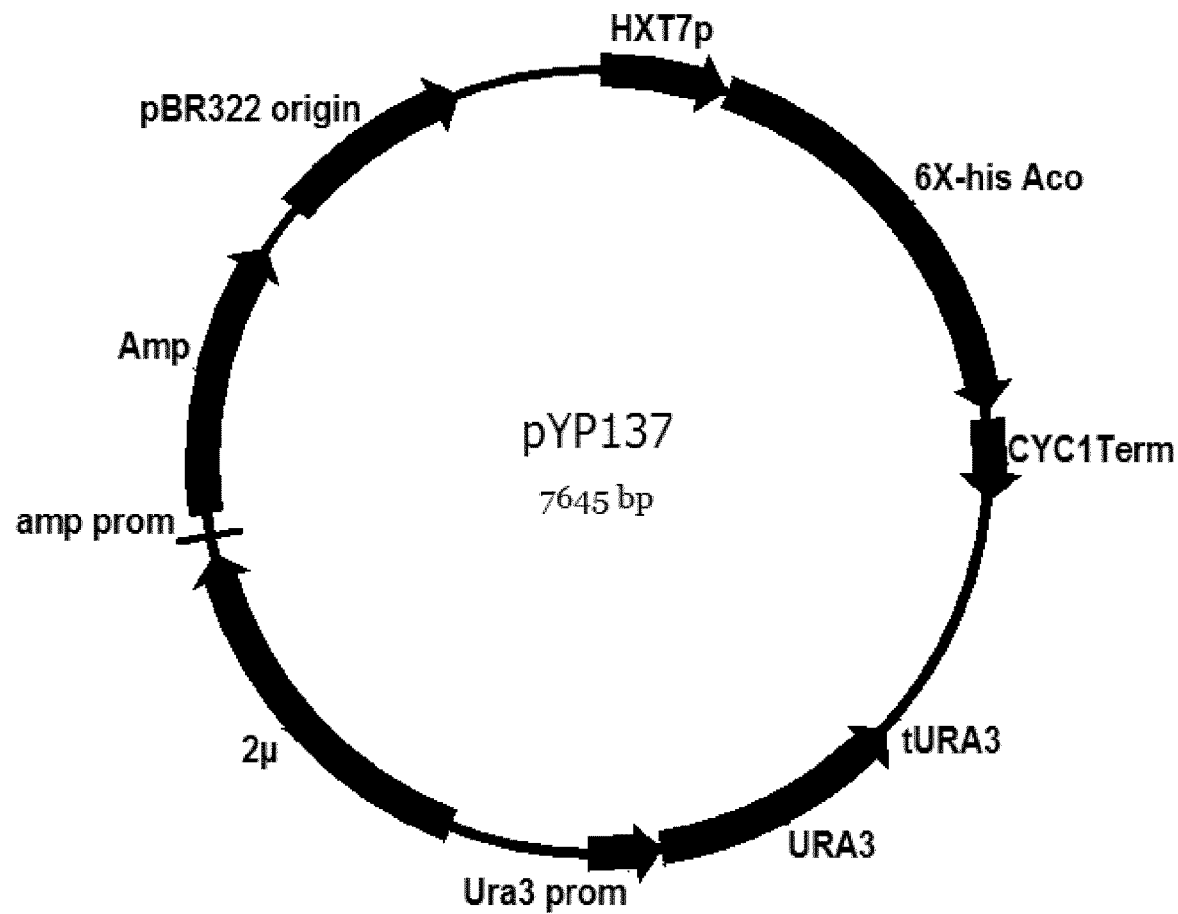
FIG. 1 is a diagram of pYP137 construction vector for overexpression of Aco in *S. cerevisiae*.

One embodiment of the invention is a method for fermentative production of n-butylacrylate (n-BA) comprising the steps of
  i) providing a recombinant microorganism comprising a butanol producing pathway, an acryloyl-CoA producing pathway and expressing an AAT gene encoding an AAT enzyme having an n-BA forming activity and
  ii) culturing said microorganism under conditions that allow for the production of n-BA and
  iii) recovering n-BA from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having an n-BA forming activity means an AAT enzyme catalysing the reaction of acryloyl-CoA and butanol to n-BA and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "acryloyl-CoA producing pathway" means a metabolic pathway comprising all enzymes catalyzing the biochemical reactions to form acryloyl-CoA from other metabolite(s). Such pathways have previously been established in microorganisms as for example described in (Zhou, Zhang et al. 2011) (Chu, Ahn et al. 2015).

Another embodiment of the invention is a method for fermentative production of n-BA as described above wherein the AAT gene encoding an AAT enzyme having an n-BA forming activity is selected from the group consisting of (I) a nucleic acid molecule comprising a sequence of SEQ ID NO: 1, 3, 5, 7, 9, 11 or 13, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and (IV) a nucleic acid molecule encoding a polypeptide of SEQ ID NO: 2, 4, 6, 8, 10, 12, or 14 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

n-BA forming activity may be quantified by an assay as described in (Fikri E. L. Yahyaoui 2002).

A further embodiment of the invention is a recombinant microorganism comprising an introduced, increased or enhanced activity and/or expression of a nucleic acid molecule encoding an AAT gene encoding an AAT enzyme having an n-BA forming activity. Preferably, said recombinant microorganism is further comprising a butanol producing pathway and an acryloyl-CoA producing pathway. More preferably, the nucleic acid molecule encoding an AAT gene encoding an AAT enzyme having an n-BA forming activity that is having an introduced, increased or enhanced activity and/or expression in the recombinant microorganism of the invention is selected from the group consisting of (I) a nucleic acid molecule comprising a sequence of SEQ ID NO: 1, 3, 5, 7, 9, 11 or 13, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and (III) a nucleic acid molecule hybridizing under medium stringent conditions, more preferably under high stringent conditions, most preferably under very high stringent conditions to the complement of a nucleic acid molecule having SEQ ID NO: 1, 3, 5, 7, 9, 11 or 13, and (IV) a nucleic acid molecule encoding a polypeptide of SEQ ID NO: 2, 4, 6, 8, 10, 12, or 14 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

In one embodiment the n-BA forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus spp., Micrococcus sp. CCM825, Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella* typhimurium, *Salmonella schottmulleri, Xanthomonas citri, Synechocystis* sp., *Synechococcus elongatus, Thermosynechococcus elongatus, Microcystis aeruginosa, Nostoc* sp., *N. commune, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::loxP adh3::loxP; adh4Δ:: loxP, adh5Δ::loxP Δadh1,3,4,5 (all with loxP)].

A further embodiment of the invention is a composition comprising one or more recombinant n-BA forming microorganisms of the invention as defined above. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing n-BA comprising the steps of:
(I) introducing, increasing or enhancing the activity and/or expression of an AAT gene encoding an AAT enzyme having an n-BA forming activity in a microorganism; and
(II) further introducing in the microorganism a butanol producing pathway and an acryloyl-CoA producing pathway.

Introducing a butanol or an acryloyl-CoA producing pathway means introducing into the recombinant microorganism all enzymes necessary for catalysing the biochemical reactions to form butanol or acryloyl-CoA respectively, from other metabolite(s).

The AAT gene that is introduced, increased or enhanced in the recombinant microorganism used in the method for producing a recombinant microorganism producing n-BA is selected from the group consisting of
(I) a nucleic acid molecule comprising a sequence of SEQ ID NO: 1, 3, 5, 7, 9, 11 or 13, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and
(IV) a nucleic acid molecule encoding a polypeptide of SEQ ID NO: 2, 4, 6, 8, 10, 12, or 14 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
(I) a nucleic acid molecule comprising a sequence of SEQ ID NO: 1, 3, 5, 7, 9, 11 or 13, and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11 or 13, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11 or 13, and
(IV) a nucleic acid molecule encoding a polypeptide of SEQ ID NO: 2, 4, 6, 8, 10, 12, or 14 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, or 14 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the n-BA forming activity as the polypeptide having SEQ ID NO: 2, 4, 6, 8, 10, 12, or 14 and wherein the promoter is heterologous to said nucleic acid molecule.

A further embodiment of the invention is a method of culturing or growing the n-BA forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the n-BA forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing n-BA, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a n-BA forming recombinant microorganism of the invention or a composition of the invention for the fermentative production of n-BA is an additional embodiment of the invention. A further embodiment of the invention is a process for fermentative production of n-BA comprising the steps of
 I) growing the n-BA forming microorganism as defined above in a fermenter and
 II) recovering n-BA from the fermentation broth obtained in I).

A further embodiment of the invention is a method for fermentative production of butyl propionate comprising the steps of
 i) providing a recombinant microorganism comprising a butanol producing pathway, an propionyl-CoA producing pathway and expressing an AAT gene encoding an AAT enzyme having an butyl propionate forming activity and
 ii) culturing said microorganism under conditions that allow for the production of butyl propionate and
 iii) recovering butyl propionate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having a butyl propionate forming activity means an AAT enzyme catalysing the reaction of propionyl-CoA and butanol to butyl propionate and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "propionyl-CoA producing pathway" means a metabolic pathway comprising all enzymes catalyzing the biochemical reactions to form propionyl-CoA from other metabolite(s). Such pathways have previously been established in microorganisms as for example described in (Yuzawa, Chiba et al. 2012).

Another embodiment of the invention is a method for fermentative production of butyl propionate wherein the AAT gene encoding an AAT enzyme having a butyl propionate forming activity is selected from the group consisting of
 (I) a nucleic acid molecule comprising a sequence of SEQ ID NO: 1, 3, 5, 7, 9, 11, 13, 15, 17, 19, 21, 23 or 25, and
 (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and
 (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and
 (IV) a nucleic acid molecule encoding a polypeptide of SEQ ID NO: 2, 4, 6, 8, 10, 12, 14, 16, 18, 20, 22, 24 or 26 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

Butyl propionate forming activity may be quantified by an assay as described in (Fikri E. L. Yahyaoui 2002).

A further embodiment of the invention is a butyl propionate forming recombinant microorganism comprising an introduced, increased or enhanced activity and/or expression of a nucleic acid molecule encoding an AAT gene encoding an AAT enzyme having a butyl propionate forming activity. Preferably, said recombinant microorganism is further comprising a butanol producing pathway and an propionyl-CoA producing pathway. More preferably, the nucleic acid molecule encoding an AAT gene encoding an AAT enzyme having a butyl propionate forming activity that is having an introduced, increased or enhanced activity and/or expression in the recombinant microorganism of the invention is selected from the group consisting of (I) a nucleic acid molecule comprising a sequence of SEQ ID NO: 1, 3, 5, 7, 9, 11, 13, 15, 17, 19, 21, 23 or 25, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and (IV) a nucleic acid molecule encoding a polypeptide of SEQ ID NO: 2, 4, 6, 8, 10, 12, 14, 16, 18, 20, 22, 24 or 26 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

In one embodiment the butyl propionate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris*,

*Zygosaccharomyces* spec, such as *Zygosaccharomyces rouxii* and *Zygosaccharomyces bailii*, *Candida* spec, such as *Candida boidinii*, *Candida utilis*, *Candida freyschussii*, *Candida glabrata* and *Candida sonorensis*, *Schwanniomyces* spec, such as *Schwanniomyces occidentalis*, *Arxula* spec, such as *Arxula adeninivorans*, *Ogataea* spec such as *Ogataea minuta*, *Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::loxP adh3::loxP; adh4Δ:: loxP, adh5Δ::loxP Δadh1,3,4,5 (all with loxP)].

A further embodiment of the invention is a composition comprising one or more recombinant butyl propionate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing butyl propionate comprising the steps of:

(I) introducing, increasing or enhancing the activity and/or expression of an AAT gene encoding an AAT enzyme having an butyl propionate forming activity in a microorganism; and (II) further introducing in the microorganism a butanol producing pathway and an propionyl-CoA producing pathway.

Introducing a butanol or a propionyl-CoA producing pathway means introducing into the recombinant microorganism all enzymes necessary for catalysing the biochemical reactions to form butanol or propionyl-CoA respectively, from other metabolite(s).

The AAT gene that is introduced, increased or enhanced in the recombinant microorganism used in the method for producing a recombinant microorganism producing butyl propionate is selected from the group consisting of (I) a nucleic acid molecule comprising a sequence of SEQ ID NO: 1, 3, 5, 7, 9, 11, 13, 15, 17, 19, 21, 23 or 25, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and (IV) a nucleic acid molecule encoding a polypeptide of SEQ ID NO: 2, 4, 6, 8, 10, 12, 14, 16, 18, 20, 22, 24 or 26 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of (I) a nucleic acid molecule comprising a sequence of SEQ ID NO: 1, 3, 5, 7, 9, 11, 13, 15, 17, 19, 21, 23 or 25, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 11, 13, 15, 17, 19, 21, 23 or 25, and (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 11, 13, 15, 17, 19, 21, 23 or 25, and (IV) a nucleic acid molecule encoding a polypeptide of SEQ ID NO: 2, 4, 6, 8, 10, 12, 14, 16, 18, 20, 22, 24 or 26 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 12, 14, 16, 18, 20, 22, 24 or 26 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl propionate forming activity as the polypeptide having SEQ ID NO: 2, 4, 6, 8, 10, 12, 14, 16, 18, 20, 22, 24 or 26 and wherein the promoter is heterologous to said nucleic acid molecule.

A further embodiment of the invention is a method of culturing or growing the butyl propionate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the butyl propionate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing butyl propionate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a butyl propionate forming recombinant microorganism of the invention or a composition of the invention for the fermentative production of butyl propionate is an additional embodiment of the invention. A further embodiment of the invention is a process for fermentative production of butyl propionate comprising the steps of
I) growing the butyl propionate forming microorganism of the invention in a fermenter and
II) recovering butyl propionate from the fermentation broth obtained in I).

A further embodiment of the invention is a method for fermentative production of butyl lactate comprising the steps of
i) providing a recombinant microorganism comprising a butanol producing pathway, a lactoyl-CoA producing pathway and expressing an AAT gene encoding an AAT enzyme having a butyl lactate forming activity and
ii) culturing said microorganism under conditions that allow for the production of butyl lactate and
iii) recovering butyl lactate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having a butyl lactate forming activity means an AAT enzyme catalysing the reaction of lactoyl-CoA and butanol to butyl lactate and CoA. The AAT enzyme may be endogenous or heterologous to the microorganism.

A "butanol producing pathway" means a metabolic pathway comprising all enzymes catalysing the biochemical reactions to form butanol from other metabolite(s). Such pathways have previously been established in microorganisms as for example described in (Schadeweg and Boles 2016).

A "lactoyl-CoA producing pathway" means a metabolic pathway comprising all enzymes catalyzing the biochemical reactions to form lactoyl-CoA from other metabolite(s). Such pathways have previously been established in microorganisms as for example described in (Nevoigt 2008).

Another embodiment of the invention is a method for fermentative production of butyl lactate wherein the AAT gene encoding an AAT enzyme having a butyl lactate forming activity is selected from the group consisting of
(I) a nucleic acid molecule comprising a sequence of SEQ ID NO: 1, 3, 5, 7, 9, 15, 17 or 19 and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
(IV) a nucleic acid molecule encoding a polypeptide of SEQ ID NO: 2, 4, 6, 8, 10, 16, 18 or 20 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20.

Butyl lactate forming activity may be quantified by an assay as described in (Fikri E. L. Yahyaoui 2002).

A further embodiment of the invention is a butyl lactate forming recombinant microorganism comprising an introduced, increased or enhanced activity and/or expression of a nucleic acid molecule encoding an AAT gene encoding an AAT enzyme having a butyl lactate forming activity. Preferably, said recombinant microorganism is further comprising a butanol producing pathway and a lactoyl-CoA producing pathway. More preferably, the nucleic acid molecule encoding an AAT gene encoding an AAT enzyme having a butyl lactate forming activity that is having an introduced, increased or enhanced activity and/or expression in the recombinant microorganism of the invention is selected from the group consisting of
- (I) a nucleic acid molecule comprising a sequence of SEQ ID NO: 1, 3, 5, 7, 9, 15, 17 or 19 and
- (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
- (III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
- (IV) a nucleic acid molecule encoding a polypeptide of SEQ ID NO: 2, 4, 6, 8, 10, 16, 18 or 20 or a functional fragment thereof, and
- (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
- wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20.

In one embodiment the butyl lactate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::loxP adh3::loxP; adh4Δ:: loxP, adh5Δ::loxP Δadh1,3,4,5 (all with loxP)].

A further embodiment of the invention is a composition comprising one or more recombinant butyl lactate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing butyl lactate comprising the steps of:
(I) introducing, increasing or enhancing the activity and/ or expression of an AAT gene encoding an AAT enzyme having a butyl lactate forming activity in a microorganism; and
(II) further introducing in the microorganism a butanol producing pathway and a lactoyl-CoA producing pathway.

Introducing a butanol or a lactoyl-CoA producing pathway means introducing into the recombinant microorganism all enzymes necessary for catalysing the biochemical reactions to form butanol or lactoyl-CoA respectively, from other metabolite(s).

The AAT gene that is introduced, increased or enhanced in the recombinant microorganism used in the method for producing a recombinant microorganism producing butyl lactate is selected from the group consisting of
(I) a nucleic acid molecule comprising a sequence of SEQ ID NO: 1, 3, 5, 7, 9, 15, 17 or 19 and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
(IV) a nucleic acid molecule encoding a polypeptide of SEQ ID NO: 2, 4, 6, 8, 10, 16, 18 or 20 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of
(I) a nucleic acid molecule comprising a sequence of SEQ ID NO: 1, 3, 5, 7, 9, 15, 17 or 19 and
(II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, 3, 5, 7, 9, 15, 17 or 19, and
(III) a nucleic acid molecule hybridizing under medium stringent conditions, preferably under high stringent conditions, more preferably under very high stringent conditions to the complement of a nucleic acid molecule having SEQ ID NO: 1, 3, 5, 7, 9, 15, 17 or 19, and
(IV) a nucleic acid molecule encoding a polypeptide of SEQ ID NO: 2, 4, 6, 8, 10, 16, 18 or 20 or a functional fragment thereof, and
(V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 2, 4, 6, 8, 10, 16, 18 or 20 or a functional fragment thereof,
wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the butyl lactate forming activity as the polypeptide having SEQ ID NO: 2, 4, 6, 8, 10, 16, 18 or 20 and wherein the promoter is heterologous to said nucleic acid molecule.

A further embodiment of the invention is a method of culturing or growing the butyl lactate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the butyl lactate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing butyl lactate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of a butyl lactate forming recombinant microorganism of the invention or a composition of the invention for the fermentative production of butyl lactate is an additional embodiment of the invention. A further embodiment of the invention is a process for fermentative production of butyl lactate comprising the steps of I) growing the butyl lactate forming microorganism of the invention in a fermenter and II) recovering butyl lactate from the fermentation broth obtained in I).

A further embodiment of the invention is a method for fermentative production of ethyl acetate comprising the steps of i) providing a recombinant microorganism comprising an ethanol producing pathway, an acetyl-CoA producing pathway and expressing an AAT gene encoding an AAT enzyme having an ethyl acetate forming activity and ii) culturing said microorganism under conditions that allow for the production of ethyl acetate and iii) recovering ethyl acetate from the fermentation broth.

The term AAT enzyme or AAT enzyme activity means an enzyme or an enzyme activity as defined by EC 2.3.1.84, catalysing an esterification step, transferring an acyl-CoA to an alcohol. An AAT enzyme having an ethyl acetate forming activity means an AAT enzyme catalysing the reaction of acetyl-CoA and ethanol to ethyl acetate and CoA. The AAT enzyme may be endogenous or heterologous to the microorganism.

An "ethanol producing pathway" means a metabolic pathway comprising all enzymes catalysing the biochemical reactions to form ethanol from other metabolite(s). Such pathways have previously been established in microorganisms (Oeser, 2015, *Yeast;* 32(1)).

An "acetyl-CoA producing pathway" means a metabolic pathway comprising all enzymes catalyzing the biochemical reactions to form acetyl-CoA from other metabolite(s). Such pathways have previously been established in microorganisms (Schadeweg, V. and E. Boles, 2016, BIOTECHNOLOGY FOR BIOFUELS (9)).

Another embodiment of the invention is a method for fermentative production of ethyl acetate wherein the AAT gene encoding an AAT enzyme having an ethyl acetate forming activity is selected from the group consisting of (I) a nucleic acid molecule comprising a sequence of SEQ ID NO: 3, 5, 7, 9, 11, 13, 15, 17, 19, 21, 23, 25 or 27, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and (IV) a nucleic acid molecule encoding a polypeptide of SEQ ID NO: 4, 6, 8, 10, 12, 14, 16, 18, 20, 22, 24, 26 or 28 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

Ethyl acetate forming activity may be quantified by an assay as described in (Fikri E. L. Yahyaoui 2002).

A further embodiment of the invention is an ethyl acetate forming recombinant microorganism comprising an introduced, increased or enhanced activity and/or expression of a nucleic acid molecule encoding an AAT gene encoding an AAT enzyme having an ethyl acetate forming activity. Preferably, said recombinant microorganism is further comprising an ethanol producing pathway and a ethyl-CoA producing pathway. More preferably, the nucleic acid molecule encoding an AAT gene encoding an AAT enzyme having an ethyl acetate forming activity that is having an introduced, increased or enhanced activity and/or expression in the recombinant microorganism of the invention is selected from the group consisting of (I) a nucleic acid molecule comprising a sequence of SEQ ID NO: 3, 5, 7, 9, 11, 13, 15, 17, 19, 21, 23, 25 or 27, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and (IV) a nucleic acid molecule encoding a polypeptide of SEQ ID NO: 4, 6, 8, 10, 12, 14, 16, 18, 20, 22, 24, 26 or 28 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

In one embodiment the ethyl acetate forming recombinant microorganism of the invention is selected from the group of prokaryotic microorganisms comprising, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermenturn, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Clostridium propionicum, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Lactobacillus* spp., *Micrococcus* sp. CCM825, *Morganella morganii, Nocardia opaca, Nocardia rugosa, Pantoea agglomerans, Planococcus eucinatus, Proteus rettgeri, Propionibacterium shermanii, Pseudomonas synxantha, Pseudomonas azotoformans, Pseudomonas jluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Bacillus coagulans, Escherichia freundii, Microbacterium ammoniaphilum, Serratia marcescens, Salmonella typhimurium, Salmonella schottmulleri, Xanthomonas citri, Synechocystis* sp., *Synechococcus elongatus, Thermosynechococcus elongatus, Microcystis aeruginosa, Nostoc* sp., *N. commune, N. sphaericum, Nostoc punctiforme, Spirulina platensis, Lyngbya majuscula, L. lagerheimii, Phormidium tenue, Anabaena* sp., *Leptolyngbya* sp, *Zymomonas mobilis* and so forth.

In another embodiment of the invention, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia* or *Trichosporon* spp., *Yamadazyma* spp. or *Pseudozyma* spp.

Preferably, the microorganism is a yeast of the genus *Saccharomyces* spec, most preferably *Saccharomyces cerevisiae* TYC-072 [MATa; ura3-52; trp1-289; leu2-3_112; his3 Δ1; MAL2-8C; SUC2 adh1::loxP adh3::loxP; adh4Δ:: loxP, adh5Δ::loxP Δadh1,3,4,5 (all with loxP)].

A further embodiment of the invention is a composition comprising one or more recombinant ethyl acetate forming microorganisms of the invention. The composition may further comprise a medium that allows grow of the recombinant microorganism of the invention. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. (Steen, Chan et al. 2008, Krivoruchko, Serrano-Amatriain et al. 2013, Tang, Feng et al. 2013). Preferably the carbon source is glucose or sucrose, more preferably the carbon source is glucose.

A further embodiment of the invention is a method for producing a recombinant microorganism producing ethyl acetate comprising the steps of:

(I) introducing, increasing or enhancing the activity and/or expression of an AAT gene encoding an AAT enzyme having an ethyl acetate forming activity in a microorganism; and (II) further introducing in the microorganism an ethanol producing pathway and an acetyl-CoA producing pathway.

Introducing an ethanol or an acetyl-CoA producing pathway means introducing into the recombinant microorganism all enzymes necessary for catalysing the biochemical reactions to form ethanol or acetyl-CoA respectively, from other metabolite(s).

The AAT gene that is introduced, increased or enhanced in the recombinant microorganism used in the method for producing a recombinant microorganism producing ethyl acetate is selected from the group consisting of (I) a nucleic acid molecule comprising a sequence of SEQ ID NO: 3, 5, 7, 9, 11, 13, 15, 17, 19, 21, 23, 25 or 27, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and (IV) a nucleic acid molecule encoding a polypeptide of SEQ ID NO: 4, 6, 8, 10, 12, 14, 16, 18, 20, 22, 24, 26 or 28 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28.

The microorganism may be selected from the group of microorganisms as defined above.

A further embodiment of the invention is a recombinant expression construct or a recombinant vector comprising said recombinant expression construct wherein the recombinant expression construct is comprising a promoter functional in a microorganism functionally linked to a nucleic acid molecule having a sequence selected from the group consisting of (I) a nucleic acid molecule comprising a sequence of SEQ ID NO: 3, 5, 7, 9, 11, 13, 15, 17, 19, 21, 23, 25 or 27, and (II) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 3, 5, 7, 9, 11, 13, 15, 17, 19, 21, 23, 25 or 27, and (III) a nucleic acid molecule hybridizing under medium stringent conditions, preferably under high stringent conditions, more preferably under very high stringent conditions to the complement of a nucleic acid molecule having SEQ ID NO: 3, 5, 7, 9, 11, 13, 15, 17, 19, 21, 23, 25 or 27, and (IV) a nucleic acid molecule encoding a polypeptide of SEQ ID NO: 4, 6, 8, 10, 12, 14, 16, 18, 20, 22, 24, 26 or 28 or a functional fragment thereof, and (V) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% identity to a polypeptide of SEQ ID NO: 4, 6, 8, 10, 12, 14, 16, 18, 20, 22, 24, 26 or 28 or a functional fragment thereof, wherein the polypeptide encoded by (II), (III) or (V) is having at least 10% or 20% preferably at least 30% or 50%, more preferably at least 60% or 70%, even more preferably at least 75%, 80%, 85% or 90%, most preferred at least 95% of the ethyl acetate forming activity as the polypeptide having SEQ ID NO: 4, 6, 8, 10, 12, 14, 16, 18, 20, 22, 24, 26 or 28 and wherein the promoter is heterologous to said nucleic acid molecule.

A further embodiment of the invention is a method of culturing or growing the ethyl acetate forming recombinant microorganism of the invention comprising the steps of inoculating a culture medium with one or more recombinant microorganism of the invention and culturing or growing said recombinant microorganism in culture medium. The medium may comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose or sucrose, more preferably the carbon source is glucose.

In some embodiments, the ethyl acetate forming recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 28° C., 30° C. or 32° C. In a most preferred embodiment the temperature is about 28° C. or 30° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 5-6.

In one embodiment of the method of producing ethyl acetate, the microorganism is cultured in a medium comprising between 1% and 30% (w/v) of a sugar, between 5% and 25% (w/v) of a sugar, between 10% and 20% (w/v) of a sugar, between 14% and 18% (w/v) of a sugar. Preferably the microorganism is cultured in a medium comprising between 15% and 20% (w/v) of a sugar.

A use of an ethyl acetate forming recombinant microorganism of the invention or a composition of the invention for the fermentative production of ethyl acetate is an additional embodiment of the invention. A further embodiment of the invention is a process for fermentative production of ethyl acetate comprising the steps of I) growing the ethyl acetate forming microorganism of the invention in a fermenter and II) recovering ethyl acetate from the fermentation broth obtained in I).

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as startcodon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, more preferably 5 fold or more, even more preferably 10 fold or more, most preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, densitometric measurement of nucleic acid concentration in a gel, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry O H et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional fragment: the term "functional fragment" refers to any nucleic acid and/or protein which comprises merely a part of the full length nucleic acid and/or full length polypeptide of the invention but still provides the same function, i.e. the function of an AAT enzyme catalyzing the reaction of acryloyl-CoA and butanol to n-BA and CoA. Preferably, the fragment comprises at least 50%, at least 60%, at least 70%, at least 80%, at least 90% at least 95%, at least 98%, at least 99% of the sequence from which it is derived. Preferably, the functional fragment comprises contiguous nucleic acids or amino acids of the nucleic acid and/or protein from which the functional fragment is derived. A functional fragment of a nucleic acid molecule encoding a protein means a fragment of the nucleic acid molecule encoding a functional fragment of the protein.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other. In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (NY); Silhavy et al. (1984) Experiments with Gene Fusions, Cold Spring Harbor Laboratory, Cold Spring Harbor (NY); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self-replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: Tm=81.5+0.41(% G+C), when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M NaPO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M NaPO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J.

Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pair-wise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multiple hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -l Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wisconsin, USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO:1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or-5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the later being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with at least one recombinant nucleic acid molecule.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, dsRNA) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e.g., when the genetic modification affects coding nucleic acid sequences of the microorganism) as compared to the wild type microorganism from which it was derived. A recombinant microorganism comprises at least one recombinant nucleic acid molecule.

The term "recombinant" with respect to nucleic acid molecules refers to nucleic acid molecules produced by man using recombinant nucleic acid techniques. The term comprises nucleic acid molecules which as such do not exist in nature or do not exist in the organism from which the nucleic acid molecule is derived, but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecules" may also comprise a "recombinant construct" which comprises, preferably operably linked, a sequence of nucleic acid molecules not naturally occurring in that order. Preferred methods for producing said recombinant nucleic acid molecules may comprise cloning techniques, directed or non-directed mutagenesis, gene synthesis or recombination techniques.

An example of such a recombinant nucleic acid molecule is a plasmid into which a heterologous DNA-sequence has been inserted or a gene or promoter which has been mutated compared to the gene or promoter from which the recombinant nucleic acid molecule derived. The mutation may be introduced by means of directed mutagenesis technologies known in the art or by random mutagenesis technologies such as chemical, UV light or x-ray mutagenesis or directed evolution technologies.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

nBA (a) and nBP (b) production in *S. cerevisiae* by feeding propionate and butanol. TYC-166 is the test strain with ACO, Pct-Me, and Cm-AAT2 expressed. TYC-181 is the negative control strain with Pct-Me and Cm-AAT2 but without ACO expressed.

EXAMPLES

The following examples serve to illustrate the invention without limiting the scope thereof.
Chemicals and Common Methods Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, CA, USA) using the Sanger technology (Sanger et al., 1977). Unless described otherwise, chemicals and reagents are obtained from Sigma Aldrich (Sigma Aldrich, St. Louis, USA), from Promega (Madison, WI, USA), Duchefa (Haarlem, The Netherlands) or Invitrogen (Carlsbad, CA, USA). Restriction endonucleases are from New England Biolabs (Ipswich, MA, USA) or Roche Diagnostics GmbH (Penzberg, Germany). Oligonucleotides are synthesized by IDT (Coralville, USA).

1. In Vivo Production of Acryloyl-CoA in *S. cerevisiae*

1.1 Heterologous Expression of Short-Chain acyl-CoA Oxidase (Aco) in *S. cerevisiae*

Short-chain acyl-CoA (coenzyme A) oxidase catalyses an oxidation reaction with saturated acyl-CoAs (e.g. propionyl-CoA) to enoyl-CoAs (e.g. acryloyl-CoA). Nucleotide sequence of the Aco gene (GB: AB017643.1) from *Arabidopsis thaliana* was obtained from the NCBI (http://www.ncbi.nlm.nih.gov/). The nucleotide sequence was codon optimized for expression in yeast with an N-terminal 6x-His tag based on the standard codon usage table in IDT Gene synthesis service (Seq ID No. 57). The 1337 bp of ACO gene was synthesized by IDT (Coralville, USA). The ACO gene fragment flanked by BamHI and HindIII restriction sites was inserted in a vector with 2 micron and pBR322 origin of replicon, ura3 and bla gene as markers to yield pYP137 (high-copy *E. coli/S. cerevisiae* shuttle vector; complements Ura-auxotrophy in *S. cerevisiae*: pBR322; CEN4-origin; AmpR; URA3, ACO under control of truncated HXT71-392 promoter and CYC1 terminator, Seq ID No. 67). The construct is subjected to be introduced in *S. cerevisiae* with various combinations of other genes in the pathway (FIG. 1).

1.2 Heterologous Expression of Propionyl-CoA Transferase in *S. cerevisiae*

Figure 2:
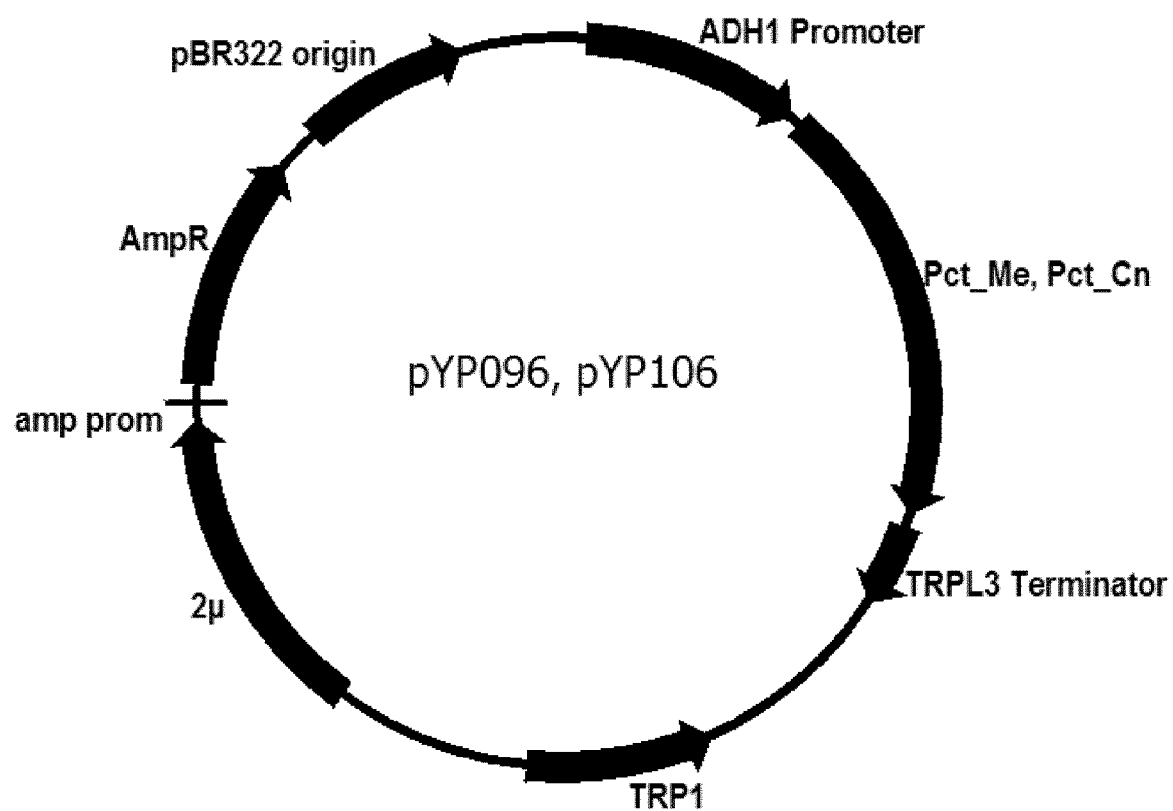
FIG. 2 is a diagram of pYP096, pYP106 construction vector for overexpression of pct in *S. cerevisiae*.

Enzymatic activity of pct is to transfer CoA to short carbon length acids by forming thioester bond. This yield various acyl-CoAs as intermediates of various biosynthetic pathways. Propionyl-CoA transferases use acetyl-CoA as a CoA donor to create propionyl-CoA from propionate. Pct genes used for this experiment from *Megasphaera elsdenii*, (CCC72964) and from *Cupriavidus necator* (CAJ93797) were codon-optimized for expression in *S. cerevisiae* and synthesized by GeneScript (Piscataway, USA) and IDT (Coralville, USA), yielding pct-Me (Seq ID No. 59) and pct-CN (Seq ID No. 61) (Prabhu et. al 2012). These genes were cloned into gene overexpression plasmids by homologous recombination methods described in prior publications (Gietz et. al., 2007). The pct genes were inserted seamlessly into the *E. coli/S. cerevisiae* shuttle plasmid to overexpress the protein from the strong constitutive promoter ADH1 and TRPL3 terminator with tryptophan auxotrophic marker in 2micron base high-copy expression vector. The resulting plasmids pYP096 (Seq ID No. 65), and pYP106 (Seq ID No. 66) are listed in the Table 1 (FIG. 2).

TABLE 1

List of plasmids encoding for different propionate CoA-transferase

| Plasmid | Plasmid description | Enzyme Key | Species/Protein | Accession #, Seq ID No. |
|---------|---------------------|------------|-----------------|-------------------------|
| pYP096 | high-copy *E. coli/S. cerevisiae* shuttle vector; complements Trp-auxotrophy in *S. cerevisiae*: pBR322; 2 μm-ori; AmpR; TRP1; ADH1 promoter and RPL3 terminator, contains codon-optimized pct of *M. elsdenii* | Pct-Me | *Megasphaera elsdenii* | CCC72964, Seq ID No. 65 |
| pYP106 | high-copy *E. coli/S. cerevisiae* shuttle vector; complements Trp-auxotrophy in *S. cerevisiae*: pBR322; 2 μm-ori; AmpR; TRP1; ADH1 promoter and RPL3 terminator, contains codon-optimized pct of *Cupriavidus necator* | Pct-Cn | *Cupriavidus necator* | CAJ93797, Seq ID No. 66 |

2. In Vivo Production of Lactoyl-CoA in *S. cerevisiae*

In order to produce lactoyl-CoA in the cytosol of *S. cerevisiae*, conversion of pyruvate to lactate and lactate to lactoyl-CoA has to occur by heterologous enzymes. Lactate dehydrogenase is responsible to convert pyruvate to lactate with NADH, and lactate dehydrogenase (ldhA) from *E. coli* was expresses in yeast after codon optimization, yielding ldhA-sc (Seq ID No. 69). To overexpress ldhA-sc in *S. cerevisiae*, a yeast shuttle expression vector was constructed. The ldhA-sc was inserted seamlessly by homologues recombination between the HXT7 promoter and CYC1 terminator on a plasmid (high-copy *E. coli/S. cerevisiae* shuttle vector; complements His-auxotrophy in *S. cerevisiae*: pBR322; 2 μ-ori; AmpR; HIS3). The resulting plasmid was named pYP024 (Seq ID No. 71). This plasmid was transformed into *S. cerevisiae* W303-1A strain to yield strain TYC-006. TYC-006 was cultured in the synthetic media and the cultured broth contained lactate which was converted from lactate. This lactate was converted further to lactoyl-CoA by expression of propionyl-CoA transferase, pct-Me (Seq ID No. 59), and pct-Cn (Seq ID No. 61) in the *S. cerevisiae* strain with ldhA-sc.

3. Heterologous Expression of Alcohol Acyl Transferase (AAT) in *P. pastoris* and *S. cerevisiae*

Figure 3:
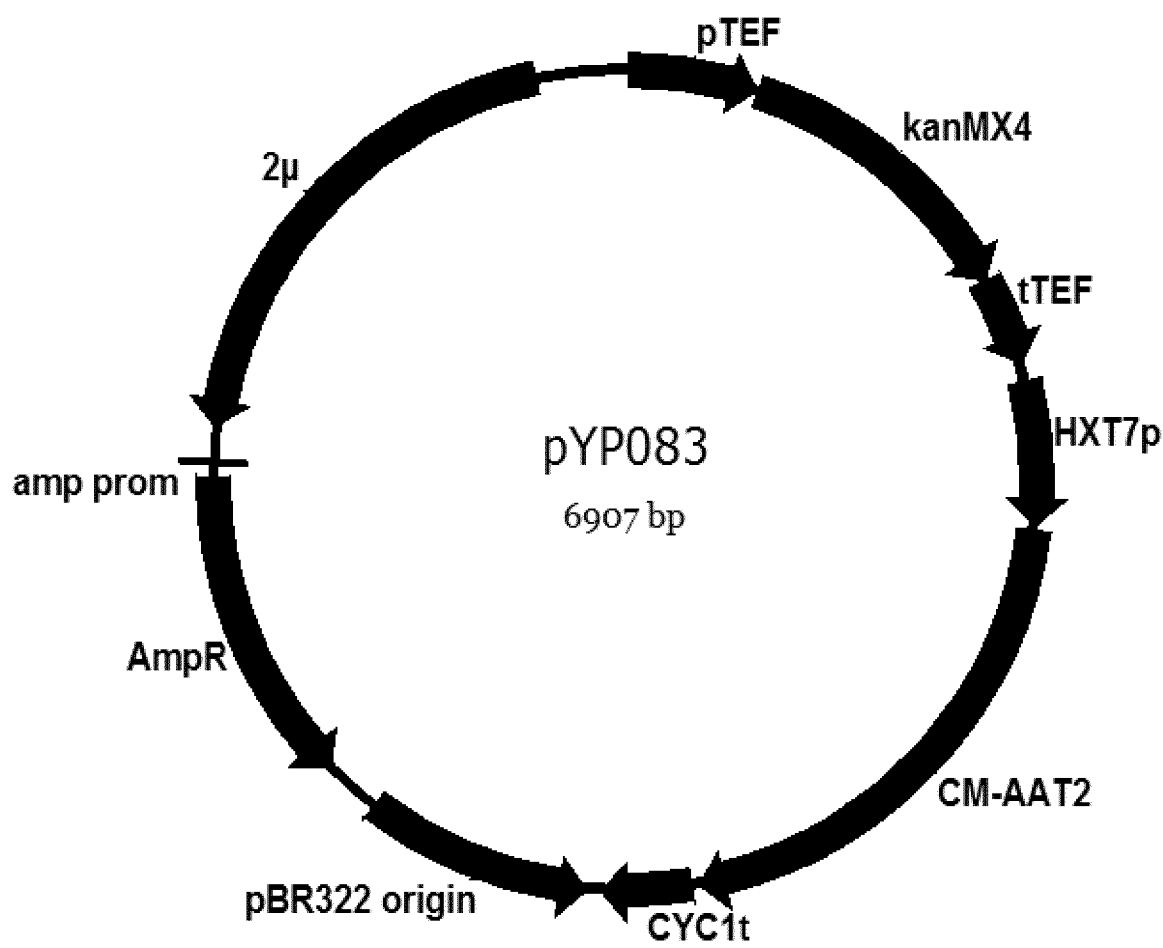
FIG. 3 is a diagram of pYP083 construction vector for overexpression of AAT in *S. cerevisiae*.

AAT is responsible for forming an ester bond between alcohols and acyl-CoAs. Various putative AATs were chosen for analysis (see Table 2). Selected AAT genes were subjected to go through activity screening tests in vitro. The methylotrophic yeast *P. pastoris* was chosen as expression host for the evaluation of expression of candidate genes encoding putative AATs. Expression constructs were set up in the plasmid pD902 (DNA 2.0) which provides the strong methanol-inducible AOX promoter. The plasmid was modified by inserting the PARS1 element, which allowed the episomal replication of the plasmid (Cregg, J. M., et al., 1985). Selected candidate AATs were constructed into pD902e plasmids (Seq ID No. 68) and transformed in *P. pastoris* GapChap. In order to overexpress for example Cm-AAT2 in *S. cerevisiae*, the gene was cloned in a high copy overexpression vector with a strong promoter and a terminator, yielding pYP083 (Seq ID No. 64, high-copy *E. coli/S. cerevisiae* shuttle vector; confers geneticin resistance: pBR322; 2 μm-ori; AmpR; lac Z; kanMX; truncated HXT71-392 promoter and CYC1 terminator CDS: N-terminal His tagged CmAAT2_Cucumis melo) (FIG. 3).

TABLE 2

Overview of the AATs selected for expression and characterization

| SEQ ID NO | gene name | identifier | Origin | Origin | reference |
|---|---|---|---|---|---|
| 1 | CM-AAT1 | CAA94432 | *Cucumis melo* | melon | Yahyaoui et al., 2002 El-Sharkaway et al., 2005 |
| 3 | MpAAT1 | AY707098 | *Malus pumila* | apple | Souleyre et al., 2005 |
| 5 | VAAT | CAC09062 | *Fragaria vesca* | strawberry | Beckwilder et al., 2004 |
| 7 | CM-AAT2 | AAL77060 | *Cucumis melo* | melon | El-Sharkaway et al., 2005 |
| 9 | Md-AAT2 | AAS79797 | *Malus domestica* | apple | Li et al., 2006 |
| 11 | BEBT | AF500200 | *Clarkia breweri* | flower | D'Auria et al., 2002 |
| 13 | CbBEAT | AAC18062 | *Clarkia breweri* | flower | Dudareva et al., 1998 |
| 15 | SAAT | CAC09048 | *Fragaria x ananassa* | strawberry | Beekwilder et al., 2004 |
| 17 | FaAAT2 | JN089766) | *Fragaria x ananassa* | strawberry | Cumplido-Laso et al., 2012 |
| 19 | AeAT9 | HO772637 | *Actinidia eriantha* | kiwi | Günther et al., 2011 |
| 21 | Rh-AAT1 | AAW31948 | *Rosa* hybrid cultivar | flower | Guterman et al., 2006 |
| 23 | CM-AAT4 | AAW51126 | *Cucumis melo* | melon | El-Sharkaway et al., 2005 |
| 25 | ACT | WP_001010387 | (*Staphylococcus sciuri*) | bacterium | Rodriguez et al., 2014 |
| 27 | BanAAT | AX025506 | *Musa sapientum* | banana | Beekwilder et al., 2004 |
| 29 | Glossy2 | CAA61258 | *Zea mays* | maize | Tacke et al., 1995 |
| 31 | CM-AAT3 | AAW51125 | *Cucumis melo* | melon | El-Sharkaway et al., 2005 |
| 33 | BAHDFox | EMT69722 | *Fusarium oxysporum* | fungi | — |
| 35 | VpAAT1 | FJ548611 | *Vasconcellea pubescens* | papaya | Balbotin et al., 2010 |
| 37 | AMAT | AY705388 | *Vitis labrusca* | grape | Wang & De Luca, 2005 |
| 39 | Pun1 | AAV66311 | *Capsicum annum* | pepper | Stewart et al., 2005 |

TABLE 2-continued

Overview of the AATs selected for expression and characterization

| SEQ ID NO | gene name | identifier | Origin | Origin | reference |
|---|---|---|---|---|---|
| 41 | Dv3MaT | AAO12206 | Dahlia variabilis | flower | Suzuki et al., 2002 |
| 43 | NtHCT | CAD47830 | Nicotiana tababcum | tobacco | Hoffmann et al., 2003 |
| 45 | DBATAca | ACI47063 | Aspergillus candidus | fungi | — |
| 47 | TSga | WP_006129805 | Streptomyces gancidicus | bacterium | — |
| 49 | TSvi | YP_004810992 | Streptomyces violaceusniger | bacterium | — |
| 51 | CAT | YP_007500975 | Shigella sonnei | bacterium | Rodriguez et al., 2014 |
| 53 | EHT | NP_009736 | Saccharomyces cerevisae | yeast | Rodriguez et al., 2014 |
| 55 | ATF | NP_015022 | Saccharomyces cerevisae | yeast | Rodriguez et al., 2014 |

4. In Vivo Production of Butanol in *S. cerevisiae*

A butanol producing *S. cerevisiae* (TYC-185) strain was established as described in Schadeweg, V. and E. Boles, 2016.

5. In Vivo Production of nBA by Feeding Substrate

We have established a pathway within *S. cerevisiae* that is able to create n-butylacrylate from feeding of propionate and n-butanol. The first step uses propionyl-CoA transferase (*M. elsdenii*) to convert propionate to propionyl-CoA. Then, the Acyl-CoA dehydrogenase (ACO) enzyme from *A. thaliana* to convert the propionyl-CoA to acryloyl-CoA. Further down the pathway, acryloyl-CoA and n-butanol become key intermediates, which are esterified by the activity of an alcohol acyltransferase (AAT) to the desired end product n-butylacrylate. We used TYC-072 modified strain of *S. cerevisiae* to introduce nBA biosynthetic pathway plasmids.

TYC-072 was transformed with a set of plasmids, pYP137 (Seq ID No. 67), pYP096 (Seq ID No. 65), and pYP083 (Seq ID No. 64) from which Aco, pct-Me, and cm-AAT2 are overexpressed, to yield *S. cerevisiae* strain TYC-166. TYC-166 was cultured in synthetic defined SD media (Bacto-Yeast nitrogen base without amino acids, 1.7 g; Glucose, 20 g; Dropout mix, 2 g/1 L) with G418 and without TRP and URA. As a negative control, an empty control vector instead of the Aco vector was introduced into TYC-072 with pct-Me and cm-AAT2 overexpression vectors to yield *S. cerevisiae* strain TYC-181. These strains were grown in SE-TRP-URA+G418 selective minimal media (glutamic acid, 1 g; Bacto-Yeast nitrogen base without amino acids and ammonium sulfate, 1.7 g; Dropoutmix, 2 g; glucose 20 g/1 L) at 30° C. (Table 3).

TABLE 3

Strains to produce n-butylacrylate in *S. cerevisiae*.

| Strain Name | Description of strain | plasmids | Selection markers |
|---|---|---|---|
| TYC-72 | MATa; ura3-52; trp1-289; leu2-3_112; his3 Δ1; MAL2-8C; SUC2 adh1::loxP adh3::loxP; adh4Δ::loxP, adh5Δ::loxP Δadh1,3,4,5 (all with loxP), Ethanol non-producer | none | Auxotrophic: Trp, Ura, Leu, His |
| TYC-166 | Prepared from TYC-072, Ethanol non-producer, overexpress Aco, pct-Me, and Cm-AAT2 | pYP083 (Cm-AAT2) pYP096 (pct-ME) pYP137 (ACO) | Dominant: G418 Auxotrophic: Trp, Ura |
| TYC-181 | Prepared from TYC-072, Ethanol non-producer, overexpress pct-Me, and Cm-AAT2 | pYP004 (empty) pYP083 (Cm-AAT2) pYP096 (pct-ME) | Dominant: G418 Auxotrophic: Trp, Ura |
| TYC-185 | n-Butanol producer. Ethanol non-producer, MATa; ura3-52; trp1-289; leu2 3_112; his3Δ1; MAL2-8C; SUC2; adh1::loxP; adh2Δ::LEU2; adh3::loxP; adh4Δ::loxP; adh5::loxP; adh6Δ::coaA, natNT2; sfa1Δ::adhE, A267T/E568K, hphNT1; gpd2::ERG10, hbd, crt, ter, adhE2, EutE, KanMX | none | Auxotrophic: Ura, Trp, His |

Strains were grown aerobically in test tubes from glycerol stocks in 10 mL of SE-TRP-URA+G418 minimal media overnight at 30° C. and 250 rpm. These cultures were then transferred into a 250 mL baffled glass shake flask and normalized to an OD600 of 0.2 for a 25 mL culture. 3.0 g/L Sodium Propionate and 0.5% butanol were fed to the cultures every 24 hours. An additional 2% of glucose was also fed after the first 24 hours and every 24 hours thereafter. Samples were taken at 3, 6, 9, 12, 24, 36 and 48 hour time points for HPLC and Solid Phase Micro Extraction (SPME) detection. The SPME method was used to detect esters, specifically Butylacrylate, and Butyl propionate.

6. In Vivo Production of nBA from Glucose

In order to demonstrate nBA production in microorganism from glucose as a carbon source, multiple pathways are introduced to generate substrates to the final esterification step, which is performed by AAT enzymes. The two major pathways to produce two key intermediates are heterologous biosynthetic pathways for butanol and acryloyl-CoA. Two S. cerevisiae production host as described in the examples 1 and 4 showed production of acryloyl-CoA and butanol in separate experiments. We use the S. cerevisiae strain (TYC-185), which can produce butanol by reverse beta-oxidation described in example 4 as a base strain to add an acryloyl-CoA pathway and alcohol acyl transferase (AAT). AAT and genes for the acryloyl-CoA pathway, short chain acyl-CoA oxidase (ACO), propionyl-CoA transferase (pct-Me), methylmalonyl-CoA mutase, methylmalonyl-CoA decarboxylase, are integrated into the chromosome of the base strain with functional promoters and terminators. In addition, other acryloyl-CoA production pathways are used separately and/or collectively. Some of example of other acryloyl-CoA pathways are the lactate route and the 3HP route. The lactate route is composed of a set of enzymes to convert pyruvate to lactate and from lactate to lactoyl-CoA and then to acryloyl-CoA. A 3HP route is composed of a set of enzymes to convert malonyl-CoA or beta-alanine to 3-oxopropanate, which is converted to 3-hydroxypropanoate (3HP) and further to 3-hydroxypropanoyl-CoA and then form acryloyl-CoA. Other routes from glucose to 3HP to acryloyl-CoA are tested. Optimization of the protein expression is achieved by testing various promoters, integration loci, copy-number of genes, episomal plasmid expression, and culture conditions. Once all the necessary genes are expressed in S. cerevisiae, glucose is converted to acryloyl-CoA and together with butanol then esterified by an AAT to form nBA and/or other ester compounds.

7. Production of Other Ester Compounds 7.1 In Vivo Production of Other Esters Various ester compound were produced in the engineered S. cerevisiae strains with expression of heterologous pathways for nBA formation. TYC-166 and TYC-181 strains, in which an AAT and pct gene were overexpressed, showed production of n-butylpropionate (nBP) as a by-product along with nBA production. Propionate was fed to the culture broth and transformed by the cells to propionyl-CoA due to the enzyme activity of pct-ME. The propionyl-CoA together with fed butanol were esterified by the AAT activity resulting in production of n-butyl propionate (nBP). Detailed experimental methods are described in example 5. nBP in the culture broth was detected by the methods described in Example 8. Additionally, in vivo production of butyllactate was demonstrated by expression of lactate dehydrogenase and AAT in yeast.

7.2 In Vitro Production of nBA and Other Esters by AATs

In addition to nBA, in vitro formation of other ester compounds, such as butyl propionate, butyl lactate, butyl acetate, and ethyl acetate, were confirmed by in vitro enzyme activity assays using the activity of the purified AAT enzymes, which form ester compounds from acyl-CoAs and alcohols. The methylotrophic yeast P. pastoris GapChap, which provides a chaperonin co-expression, was chosen as expression host for the evaluation of expression of candidate genes encoding putative AATs. Plasmid constructs with N-terminal 6x-his-tagged AATs were cloned with the strong methanol-inducible AOX promoter. The cultures of individual constructs were pooled, washed once with 100 mM sodium phosphate buffer pH 7.5 and re-suspended in 50 mM sodium phosphate buffer pH 8.0 containing complete plus EDTA free protease inhibitor (Roche), 300 mM NaCl, 10 mM imidazole. A Branson Sonifier 250 was used to generate a crude cell extract; 8×5 min pulses with 50% duty cycle and output level 7 were used to disrupt the cells in an appropriate vessel on ice. After centrifugation the supernatant was filtered before loading onto a HisTrap HF Ni-NTA column (1 ml, GE Healthcare) equilibrated with buffer A (300 mM NaCl, 50 mM sodium phosphate buffer pH 8.0, 10 mM imidazole). Buffer A was also used for loading and washing. A gradient was applied by switching from buffer A to buffer B (300 mM NaCl, 50 mM sodium phosphate buffer pH 8.0, 500 mM imidazole) within 10 column volumes (CV). Elution was prolonged by 5 additional CV of buffer B. Fractions of 1 ml were collected and separately analyzed by SDS-PAGE and activity measurements (GC/MS) for the identification of AAT protein. Up to 3 fractions were pooled and desalted by size exclusion chromatography (PD10, GE-Healthcare). Final preparations contained 100 mM sodium phosphate buffer pH 7.5 and were stored on ice. Purity was analyzed by SDS-PAGE and densitometric analysis of the corresponding protein band. Total protein amount was determined by Micro-BCA Assay (Thermo Fisher). The assay to determine the activity of AATs was set up as follows: 100 mM potassium phosphate buffer pH 7.5, 5 mM alcohol (e.g. butanol), 0.5 mM acyl-CoA, 1 mg/mL BSA, and 20 µl enzyme sample in a total volume of 100 µl in a 2 mL glass vial, which was sealed immediately after setup. Samples were set up in duplicate and incubated at room temperature (RT) for 0, 2, 4, 8 and 24 h respectively. Subsequently enzymes were inactivated by heat denaturation at 65° C. for 20 min. Afterward samples were analyzed by the methods described in Example 8. Various AATs showed esterase activities to various substrates to form butylacrylate, butyl propionate, butyl lactate, butyl acetate, and ethyl acetate. (Table. 4)

TABLE 4

Activities of AATs towards the formation of variable compounds.

| SEQ ID NO | Enzyme | butyl acrylate | butyl propionate | butyl lactate | ethyl acetate |
|---|---|---|---|---|---|
| 2 | Cm-AAT1 | o | o | o | x |
| 4 | Mp-AAT1 | o | o | o | o |
| 6 | VAAT | o | o | o | o |
| 8 | CM-AAT2 | o | o | o | o |
| 10 | Md-AAT2 | o | o | o | o |
| 12 | BEBT | o | o | x | o |
| 14 | CbBEAT | o | o | x | o |
| 16 | SAAT | x | o | o | o |

TABLE 4-continued

Activities of AATs towards the formation of variable compounds.

| SEQ ID NO | Enzyme | butyl acrylate | butyl propionate | butyl lactate | ethyl acetate |
|---|---|---|---|---|---|
| 18 | Fa-AAT2 | x | o | o | o |
| 20 | AeAT9 | x | o | o | o |
| 22 | Rh-AAT1 | x | o | x | o |
| 24 | CM-AAT4 | x | o | x | o |
| 26 | ACT | x | o | x | o |
| 28 | BanAAT | x | x | x | o | o: detected,
x: not detected

8. Detection of nBA from Culture Broth

Figure 4:
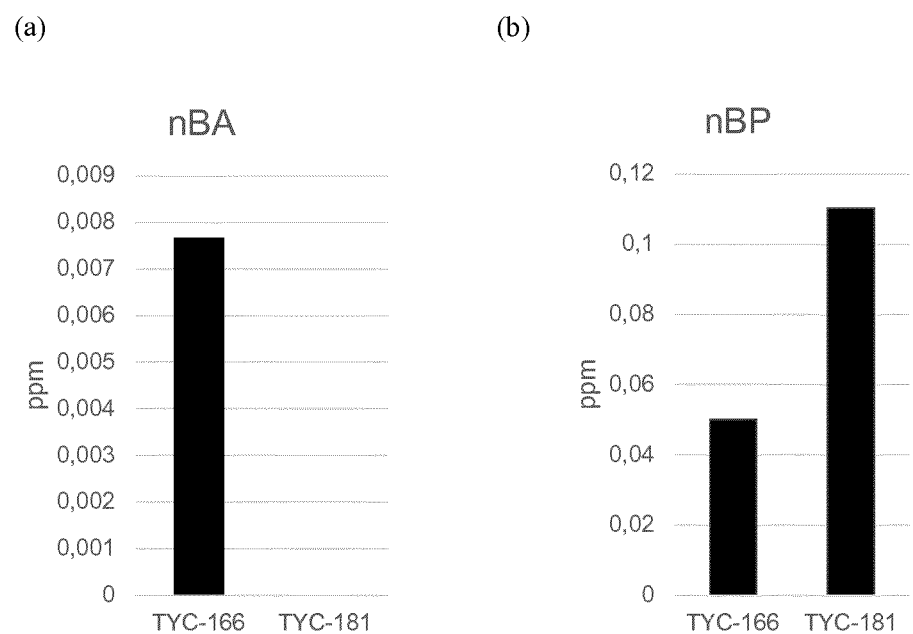
FIGS. 4A and 4B are graphs of nBA and nBP, respectively, production in *S. cerevisiae* by feeding propionate and butanol. TYC-166 is a test strain with ACO, Pct-Me, and Cm-AAT2 expressed. TYC-181 is a negative control strain with Pct-Me and Cm-AAT2 but without ACO expressed.

Solid phase micro extraction (SPME)/GC/MS was used to detect nBA and other ester compounds from the culture broth. SPME samples were prepared by adding 500 μL of filtered (0.22 μm) cultured media into the head space analysis vial. SPME was done with carboxen/polydimethylsiloxane fiber. Extraction was done at 40° C. for 15 min after samples were conditioned at 40° C. for 10 min. Desorption was carried out at injection port at 250° C., followed by GC separation (column DB-624) and MS detection (full scan mode). nBA was detected from the broth of TYC-166 culture. No nBA was detected from TYC-181, which was negative control experiment. Both strains produced n-butyl-propionate as a by-product formed by esterification of butanol and propionyl-CoA (FIG. 4).

We claim:

1. A method for fermentative production of n-butylacrylate (n-BA) comprising the steps of:
   i) providing a recombinant microorganism comprising a butanol producing pathway and an acryloyl-CoA producing pathway and expressing an alcohol acyl transferase (AAT) gene encoding an AAT enzyme having an n-BA forming activity;
   ii) culturing said microorganism under conditions that allow for the production of n-BA; and
   iii) recovering n-BA from a fermentation broth;
   wherein the AAT gene encoding an AAT enzyme having an n-BA forming activity is selected from the group consisting of:
   (I) a nucleic acid molecule comprising a sequence selected from the group consisting of SEQ ID NO: 1, 3, 5, 7, 9, 11 and 13;
   (II) a nucleic acid molecule having at least 95% identity to a nucleic acid molecule selected from the group consisting of SEQ ID NO: 1, 3, 5, 7, 9, 11 and 13;
   (III) a nucleic acid molecule hybridizing to the full complement of a nucleic acid molecule having a sequence selected from the group consisting of SEQ ID NO: 1, 5, 7, 9, 11 and 13;
   (IV) a nucleic acid molecule encoding a polypeptide selected from the group consisting of SEQ ID NO: 2, 6, 8, 10, 12, and 14; and
   (V) a nucleic acid molecule encoding a polypeptide having at least 95% identity to a polypeptide selected from the group consisting of SEQ ID NO: 2, 6, 8, 10, 12, and 14.

2. A process for fermentative production of n-BA comprising the steps of:
   I) growing in a fermenter a recombinant microorganism comprising a nucleic acid molecule encoding an AAT gene encoding an AAT enzyme having an n-butylacrylate (n-BA) forming activity, wherein the microorganism also comprises a butanol producing pathway and an acryloyl-CoA producing pathway, and wherein the microorganism has an introduced, increased, or enhanced n-butylacrylate forming activity and/or expression of said AAT enzyme;
   wherein the AAT gene encoding an AAT enzyme having an n-BA forming activity is selected from the group consisting of:
   (I) a nucleic acid molecule comprising a sequence selected from the group consisting of SEQ ID NO: 1, 3, 5, 7, 9, 11 and 13;
   (II) a nucleic acid molecule having at least 95% identity to a nucleic acid molecule selected from the group consisting of SEQ ID NO: 1, 3, 5, 7, 9, 11 and 13;
   (III) a nucleic acid molecule hybridizing to the full complement of a nucleic acid molecule having a sequence selected from the group consisting of SEQ ID NO: 1, 5, 7, 9, 11 and 13;
   (IV) a nucleic acid molecule encoding a polypeptide selected from the group consisting of SEQ ID NO: 2, 6, 8, 10, 12, and 14; and
   (V) a nucleic acid molecule encoding a polypeptide having at least 95% identity to a polypeptide selected from the group consisting of SEQ ID NO: 2, 6, 8, 10, 12, and 14; and II) recovering n-BA from a fermentation broth obtained in step I).

3. The method of claim 1, wherein the nucleic acid molecule hybridizing to the full complement of a nucleic acid molecule having the sequence of SEQ ID NO: 1, 5, 7, 9, 11 and 13 hybridizes under high stringency conditions of hybridization in 7% sodium dodecyl sulfate (SDS), 0.5 M $NaPO_4$, 1 mM EDTA at 50° C. with washing in 1×SSC, 0.1% SDS at 65° C.

4. The process of claim 2, wherein the nucleic acid molecule hybridizing to the full complement of a nucleic acid molecule having the sequence of SEQ ID NO: 1, 5, 7, 9, 11 and 13 hybridizes under high stringency conditions of hybridization in 7% sodium dodecyl sulfate (SDS), 0.5 M $NaPO_4$, 1 mM EDTA at 50° C. with washing in 1×SSC, 0.1% SDS at 65° C.

* * * * *